United States Patent
Kawata et al.

(10) Patent No.: US 9,406,889 B2
(45) Date of Patent: *Aug. 2, 2016

(54) PHENANTHRENE COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Yuko Kawata, Kanagawa (JP); Hiroshi Kadoma, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,337

(22) Filed: Feb. 26, 2015

(65) Prior Publication Data

US 2015/0171333 A1  Jun. 18, 2015

Related U.S. Application Data

(63) Continuation of application No. 13/282,686, filed on Oct. 27, 2011, now Pat. No. 8,968,888.

(30) Foreign Application Priority Data

Oct. 29, 2010 (JP) .................... 2010-243323

(51) Int. Cl.
  *H01L 51/00* (2006.01)
  *C07D 333/76* (2006.01)
  *H01L 51/50* (2006.01)

(52) U.S. Cl.
  CPC .......... *H01L 51/0052* (2013.01); *C07D 333/76* (2013.01); *H01L 51/0074* (2013.01); *H01L 51/508* (2013.01); *H01L 51/006* (2013.01); *H01L 51/0085* (2013.01); *H01L 51/5016* (2013.01)

(58) Field of Classification Search
  None
  See application file for complete search history.

(56) References Cited

U.S. PATENT DOCUMENTS 7,989,644 B2  8/2011  Tanabe et al.
7,989,802 B2  8/2011  Nagao et al.
(Continued)

FOREIGN PATENT DOCUMENTS

EP  1 748 045 A1  1/2007
EP  2 108 689 A2  10/2009
(Continued)

OTHER PUBLICATIONS

Baldo, M.A. et al., "Very High-Efficiency Green Organic Light-Emitting Devices Based on Electrophosphorescence," Applied Physics Letters, Jul. 5, 1999, vol. 75, No. 1, pp. 4-6.
(Continued)

*Primary Examiner* — J. L. Yang
(74) *Attorney, Agent, or Firm* — Husch Blackwell LLP

(57) ABSTRACT

A novel compound having high triplet excitation energy and a bipolar property is provided. Specifically, a phenanthrene compound represented by General Formula (G1) is provided where $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, and Z represents a sulfur atom or an oxygen atom. The use of the phenanthrene compound as a host material of a light-emitting layer in the presence of a phosphorescent dopant allows the formation of a light-emitting element with high current efficiency.

(G1)

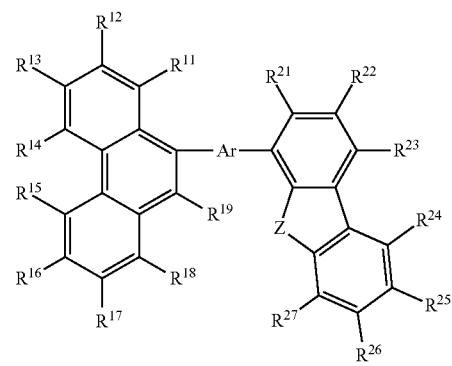

14 Claims, 22 Drawing Sheets

(56) References Cited

U.S. PATENT DOCUMENTS

| | | |
|---|---|---|
| 8,007,927 B2 | 8/2011 | Lin et al. |
| 8,221,905 B2 | 7/2012 | Lin et al. |
| 8,354,542 B2 | 1/2013 | Kawata et al. |
| 8,367,850 B2 | 2/2013 | Ma et al. |
| 8,546,584 B2 | 10/2013 | Kawata et al. |
| 8,563,740 B2 | 10/2013 | Kawata et al. |
| 8,580,402 B2 | 11/2013 | Lin et al. |
| 8,586,204 B2 | 11/2013 | Xia et al. |
| 8,642,782 B2 | 2/2014 | Suzuki et al. |
| 8,652,652 B2 | 2/2014 | Brooks et al. |
| 8,735,610 B2 | 5/2014 | Tanabe et al. |
| 8,822,708 B2 | 9/2014 | Ma et al. |
| 8,866,377 B2 | 10/2014 | Adamovich et al. |
| 8,940,412 B2 | 1/2015 | Takashima et al. |
| 8,945,724 B2 | 2/2015 | Yamamoto et al. |
| 8,946,984 B2 | 2/2015 | Tanabe et al. |
| 8,968,888 B2 * | 3/2015 | Kawata et al. ............... 428/690 |
| 2002/0025419 A1 | 2/2002 | Lee et al. |
| 2003/0127967 A1 | 7/2003 | Tsutsui et al. |
| 2007/0141387 A1 * | 6/2007 | Nakano ............... C09K 11/06 428/690 |
| 2007/0247063 A1 | 10/2007 | Murase et al. |
| 2008/0152950 A1 | 6/2008 | Je et al. |
| 2008/0314965 A1 | 12/2008 | Roberts et al. |
| 2008/0315754 A1 | 12/2008 | Kawamura et al. |
| 2009/0102366 A1 * | 4/2009 | Ushikubo et al. ............... 313/504 |
| 2009/0153034 A1 | 6/2009 | Lin et al. |
| 2010/0045170 A1 | 2/2010 | Lee et al. |
| 2011/0114928 A1 | 5/2011 | Suzuki et al. |
| 2011/0248246 A1 | 10/2011 | Ogita et al. |
| 2011/0285276 A1 | 11/2011 | Kadoma et al. |
| 2012/0061651 A1 | 3/2012 | Osaka et al. |
| 2012/0061714 A1 | 3/2012 | Osaka et al. |
| 2012/0074390 A1 | 3/2012 | Seo et al. |
| 2012/0080667 A1 | 4/2012 | Nowatari et al. |
| 2012/0091887 A1 | 4/2012 | Osaka et al. |
| 2012/0104369 A1 | 5/2012 | Kawata et al. |
| 2012/0104373 A1 | 5/2012 | Inoue et al. |
| 2013/0320312 A1 | 12/2013 | Watanabe et al. |
| 2014/0008643 A1 | 1/2014 | Lin et al. |
| 2014/0042413 A1 | 2/2014 | Xia et al. |
| 2014/0046073 A1 | 2/2014 | Kawata et al. |
| 2014/0103327 A1 | 4/2014 | Brooks et al. |
| 2014/0326977 A1 | 11/2014 | Ma et al. |
| 2015/0001524 A1 | 1/2015 | Brooks et al. |

FOREIGN PATENT DOCUMENTS

| | | |
|---|---|---|
| EP | 2 128 217 A1 | 12/2009 |
| EP | 2 163 550 A1 | 3/2010 |
| EP | 2 236 501 A1 | 10/2010 |
| EP | 2 330 102 A1 | 6/2011 |
| EP | 2 372 803 A1 | 10/2011 |
| EP | 2 511 254 A2 | 10/2012 |
| EP | 2 713 415 A1 | 4/2014 |
| JP | 2002-038141 A | 2/2002 |
| JP | 2005-314239 A | 11/2005 |
| JP | 2007-063501 A | 3/2007 |
| JP | 2007-077094 A | 3/2007 |
| JP | 2007-238500 A | 9/2007 |
| JP | 2008-545729 | 12/2008 |
| JP | 2009-249378 A | 10/2009 |
| JP | 2010-034548 A | 2/2010 |
| JP | 2012-031322 A | 2/2012 |
| WO | WO 2005/113531 A1 | 12/2005 |
| WO | WO 2006/128800 A1 | 12/2006 |
| WO | WO 2008/108256 A1 | 9/2008 |
| WO | WO 2008/143229 A1 | 11/2008 |
| WO | WO 2009/021107 A1 | 2/2009 |
| WO | WO 2009/021126 A2 | 2/2009 |
| WO | WO 2009/030981 A2 | 3/2009 |
| WO | WO 2009/084543 A1 | 7/2009 |
| WO | WO 2009/085344 A2 | 7/2009 |
| WO | WO 2009/086028 A2 | 7/2009 |
| WO | WO 2010/074087 A1 | 7/2010 |

OTHER PUBLICATIONS

European Search Report re Application No. EP 10190684.0, dated Mar. 24, 2011.

* cited by examiner

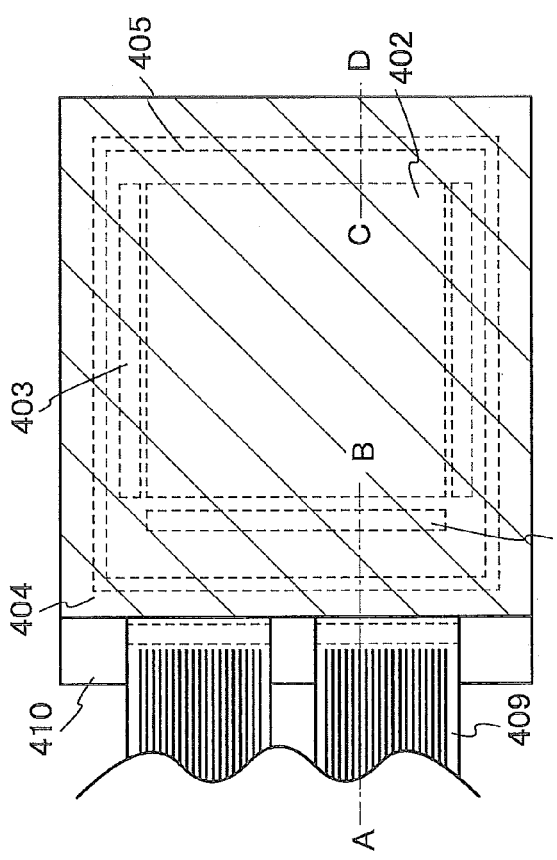
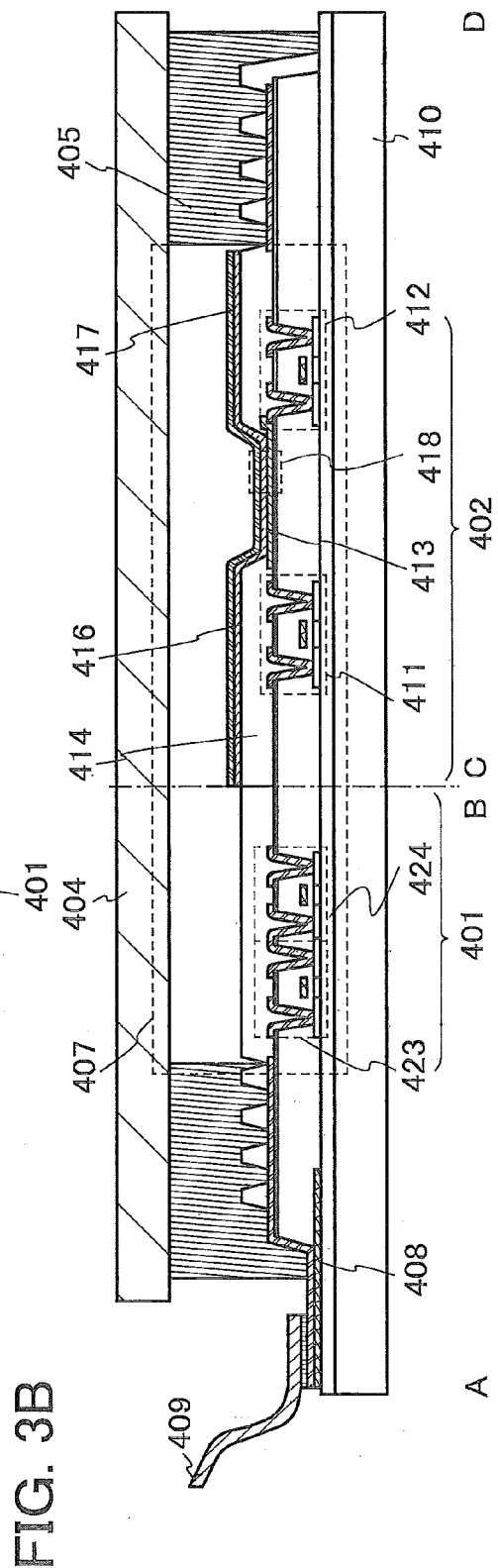
FIG. 3A
FIG. 3B

US 9,406,889 B2

PHENANTHRENE COMPOUND, LIGHT-EMITTING ELEMENT, LIGHT-EMITTING DEVICE, ELECTRONIC DEVICE, AND LIGHTING DEVICE

This application is a continuation of copending U.S. application Ser. No. 13/282,686, filed on Oct. 27, 2011 which is incorporated herein by reference.

BACKGROUND OF THE INVENTION

1. Field of the Invention

The present invention relates to a phenanthrene compound and a light-emitting element including the phenanthrene compound. The present invention also relates to a light-emitting device, an electronic device, and a lighting device each including the light-emitting element.

2. Description of the Related Art

In recent years, research and development of light-emitting elements using electroluminescence (EL) have been actively conducted. In a basic structure of such a light-emitting element, a layer containing a light-emitting substance is interposed between a pair of electrodes. By voltage application to this element, light emission can be obtained from the light-emitting substance.

Such a light-emitting element is of self-luminous type, and thus has advantages over a liquid crystal display in that visibility of pixels is high, backlight is not needed, and so on. Therefore, such a light-emitting element is regarded as being suitable as a flat panel display element. Besides, such a light-emitting element has advantages in that it can be manufactured to be thin and lightweight, and has very fast response speed.

Further, since such a light-emitting element can be formed to have a film shape, plane light emission can be easily obtained. Therefore, a large-area element capable of the plane light emission can be formed. This is a feature that is difficult to obtain with point light sources typified by an incandescent lamp and an LED or linear light sources typified by a fluorescent lamp. Therefore, the light-emitting element is very effective for use as a surface light source applicable to a lighting device and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, these carriers (i.e., electrons and holes) are recombined, whereby the light-emitting organic compound is excited. The light-emitting organic compound returns to the ground state from the excited state, thereby emitting light. Note that the excited state of an organic compound can be a singlet excited state and a triplet excited state, and luminescence from the singlet excited state (S*) is referred to as fluorescence, and luminescence from the triplet excited state (T*) is referred to as phosphorescence. The statistical generation ratio thereof in a light-emitting element is considered to be S*:T*=1:3.

At room temperature, a compound that is capable of converting a singlet excited state to luminescence (hereinafter, referred to as a fluorescent compound) generally exhibits only luminescence from the singlet excited state (fluorescence) and does not luminesce from the triplet excited state (phosphorescence). Therefore, the internal quantum efficiency (the ratio of generated photons to injected carriers) in a light-emitting element using a fluorescent compound is assumed to have a theoretical limit of 25% on the basis of S*:T*=1:3.

On the other hand, when a compound in which a triplet excited state is converted into luminescence (hereinafter, such a compound is referred to as a "phosphorescent compound") is used, internal quantum efficiency can be theoretically 75% to 100%. In other words, emission efficiency can be 3 times to 4 times as much as that of the fluorescence compound. For these reasons, a light-emitting element using a phosphorescent compound has been actively developed in recent years in order to achieve a highly efficient light-emitting element (e.g., see Non-Patent Document 1).

When a light-emitting layer of a light-emitting element is formed using the above phosphorescent compound, the light-emitting layer is formed so that the phosphorescent compound is dispersed throughout a matrix formed of another material in many cases, for suppression of the concentration quenching of the phosphorescent compound and the quenching due to triplet-triplet annihilation. In this case, the material used for forming the matrix is referred to as a host material, and the material dispersed throughout the matrix is referred to as a guest material.

When a phosphorescent compound is used for a guest material, a host material is required to have higher triplet excitation energy (a difference in energy between the ground state and the triplet excited state) than the phosphorescent compound. It is known that CBP, which is used as the host material in Non-Patent Document 1, has higher triplet excitation energy than a phosphorescent compound which emits light of green to red and is widely used as a host material for the phosphorescent compound.

However, although CBP has high triplet excitation energy, it has insufficient ability to receive holes or electrons, which results in a problem of an increase in driving voltage. Therefore, a substance which has high triplet excitation energy and also can easily accept and transport both holes and electrons (i.e., a bipolar substance) is needed as a host material for a phosphorescent compound.

Furthermore, since singlet excitation energy (an energy difference between a ground state and a singlet excited state) is higher than triplet excitation energy, a substance that has high triplet excitation energy also has high singlet excitation energy. Therefore, a substance which has high triplet excitation energy and a bipolar property as described above is also effective as a host material in a light-emitting element using a fluorescent compound as a light-emitting substance.

REFERENCE

[Non-Patent Document 1] M. A. Baldo et al., (Jul. 5, 1999), *Applied Physics Letters*, vol. 75, No. 1, pp. 4-6.

SUMMARY OF THE INVENTION

In view of the above, an object of one embodiment of the present invention is to provide a novel compound having high excitation energy, particularly a novel compound having high triplet excitation energy. In addition, an object of one embodiment of the present invention is to provide a novel compound having a bipolar property.

One embodiment of the present invention is a phenanthrene compound which has a bipolar property and in which a phenanthryl group having an electron-transport property and a dibenzothiophenyl group or a dibenzofuranyl group having a hole-transport property are bonded to each other through an arylene group. Specifically, one embodiment of the present invention is a phenanthrene compound represented by the general formulae below.

One embodiment of the present invention is a phenanthrene compound represented by General Formula (G1).

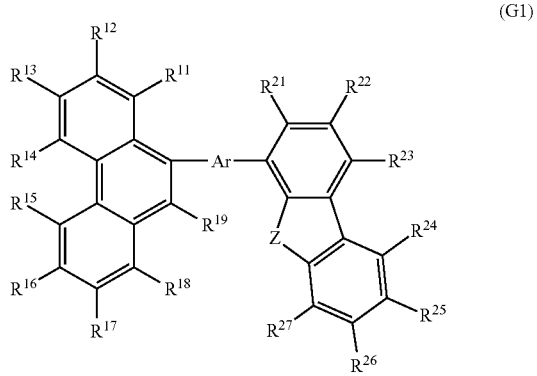

(G1)

Note that in General Formula (G1), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Ar represents a substituted or unsubstituted arylene group having 6 to 13 carbon atoms. Z represents a sulfur atom or an oxygen atom.

In General Formula (G1), Ar is preferably a substituted or unsubstituted biphenyldiyl group, more preferably a substituted or unsubstituted phenylene group.

One embodiment of the present invention is a phenanthrene compound represented by General Formula (G2).

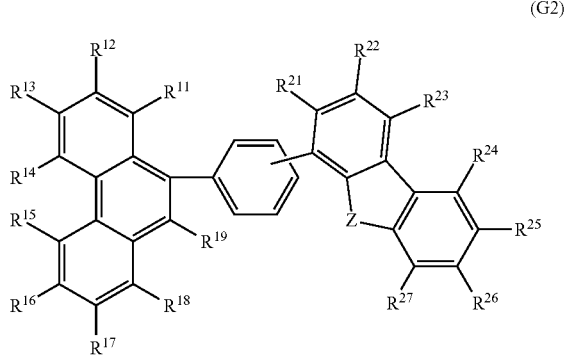

(G2)

Note that in General Formula (G2), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Z represents a sulfur atom or an oxygen atom.

One embodiment of the present invention is a light-emitting element including the phenanthrene compound. In the light-emitting element, the phenanthrene compound is preferably contained in a light-emitting layer; more preferably, the phenanthrene compound and a phosphorescent substance are contained in a light-emitting layer.

One embodiment of the present invention is a light-emitting device including the light-emitting element.

One embodiment of the present invention is an electronic device or a lighting device including the light-emitting device.

Note that the light-emitting device in this specification includes, in its category, an image display device, a light-emitting device, and a light source. In addition, the light-emitting device includes, in its category, all of a module in which a connector such as a flexible printed circuit (FPC), a tape automated bonding (TAB) tape, or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel phenanthrene compound can be provided. The phenanthrene compound has a bipolar property and is useful as a material of a light-emitting element. Moreover, the phenanthrene compound has high triplet excitation energy, and thus is useful as a host material for a phosphorescent compound.

BRIEF DESCRIPTION OF THE DRAWINGS

FIGS. 3A and 3B illustrate a light-emitting device of one embodiment of the present invention.

DETAILED DESCRIPTION OF THE INVENTION

Figure 1A:
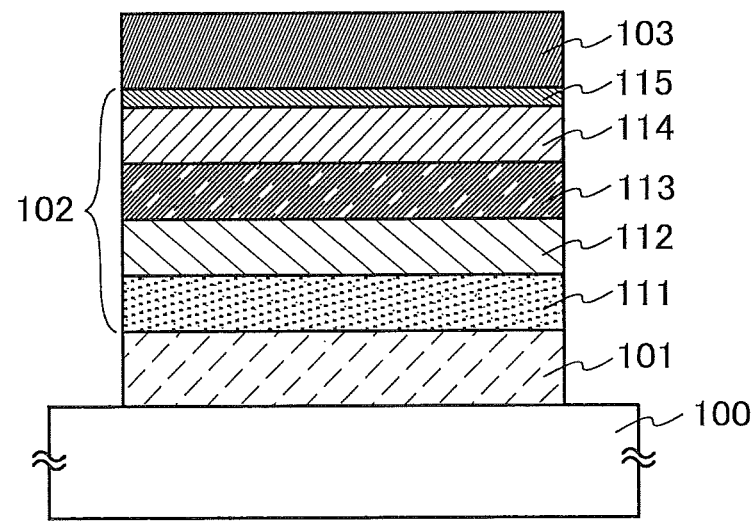
FIGS. 1A and 1B each illustrate a light-emitting element of one embodiment of the present invention.

Hereinafter, embodiments and examples will be described in detail with reference to the accompanying drawings. Note that the present invention is not limited to the following description and it will be easily understood by those skilled in the art that various changes and modifications can be made without departing from the spirit and scope of the present invention. Therefore, the present invention should not be construed as being limited to the following description of the embodiments and examples.

Embodiment 1

In this embodiment, a phenanthrene compound according to one embodiment of the present invention will be described.

The phenanthrene compound according to one embodiment of the present invention is a phenanthrene compound represented by General Formula (G1).

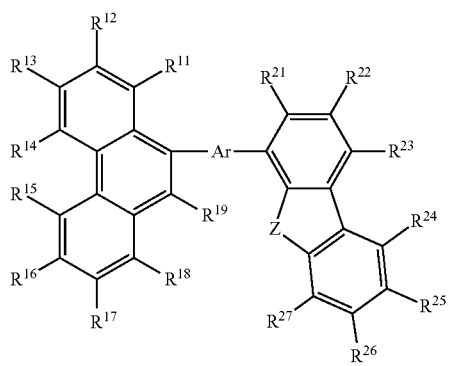

(G1)

Note that in General Formula (G1), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Ar represents a substituted or unsubstituted arylene group having 6 to 13 carbon atoms. Z represents a sulfur atom or an oxygen atom.

The phenanthrene compound represented by General Formula (G1) is a compound having a bipolar property which includes a phenanthryl group having an electron-transport property and a dibenzothiophenyl group or a dibenzofuranyl group having a hole-transport property in the molecule. Further, an arylene group represented by Ar is interposed between the phenanthryl group and the dibenzothiophenyl group or the dibenzofuranyl group, whereby conjugation is not highly expanded from the phenanthryl group to the dibenzothiophenyl group or the dibenzofuranyl group; accordingly, the band gap is considered to be increased. Ar is preferably an arylene group with narrow conjugation, such as a substituted or unsubstituted phenylene group or a substituted or unsubstituted biphenyldiyl group, in order to prevent Ar itself from causing expansion of conjugation of the compound; more preferably, Ar is a substituted or unsubstituted phenylene group.

In General Formula (G1), $R^{11}$ to $R^{19}$ and $R^{21}$ to $R^{27}$ separately represent any one of hydrogen, an alkyl group having 1 to 4 carbon atoms, and an aryl group having 6 to 13 carbon atoms. In the case where $R^{11}$ to $R^{19}$ and $R^{21}$ to $R^{27}$ are each an aryl group having 6 to 13 carbon atoms, a substituent may be incorporated to the aryl group. As examples of the substituent in that case, an alkyl group having 1 to 4 carbon atoms, a phenyl group, a naphthyl group, a fluorenyl group, and the like can be given. Note that in the case where the aryl group has two substituents, these two substituents may be bonded to each other to form a ring and the ring may be a spiro ring.

As specific examples of the structures of $R^{11}$ to $R^{19}$ and $R^{21}$ to $R^{27}$, Structural Formulae (R-1) to (R-23) and the like can be given. Note that Structural Formulae (R-16) to (R-23) are specific examples of the structures in the case where at least one of $R^{11}$ to $R^{19}$ and $R^{21}$ to $R^{27}$ is an aryl group having 6 to 13 carbon atoms and has a substituent. Further, Structural Formula (R-20) is a specific example in the case where the two substituents on the aryl group are bonded to each other to form a spiro ring system.

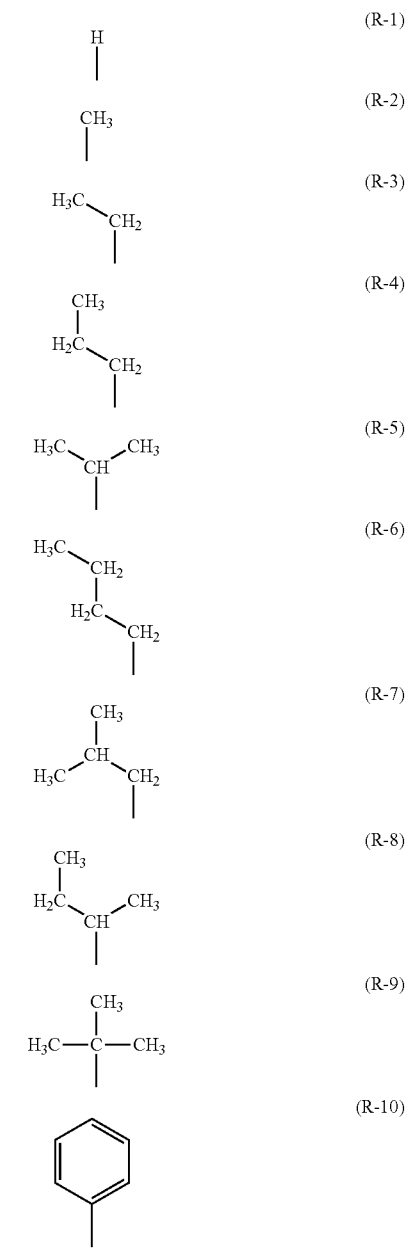

(R-11) 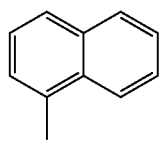

(R-12) 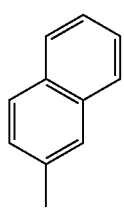

(R-13) 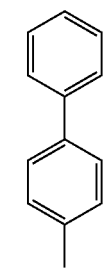

(R-14) 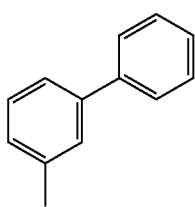

(R-15) 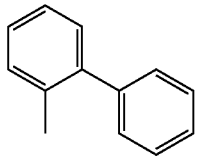

(R-16) 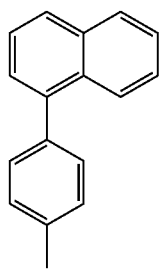

(R-17) 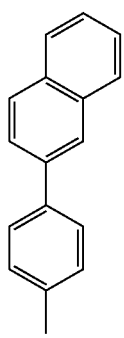

(R-18) 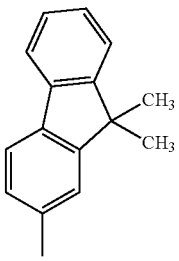

(R-19) 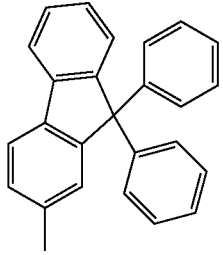

(R-20) 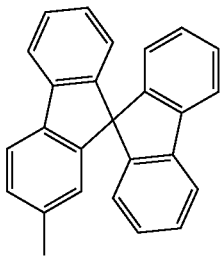

(R-21) 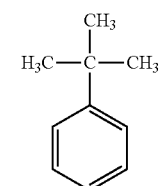

(R-22) 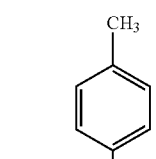

(R-23) 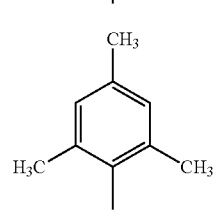

In General Formula (G1), Ar represents an arylene group having 6 to 13 carbon atoms and may have a substituent. In the case where Ar has a substituent, an alkyl group having 1 to 4 carbon atoms, a phenyl group, a naphthyl group, a fluorenyl group, and the like can be given as examples of the substituent. Note that in the case where Ar has two substituents, the substituents may be bonded to each other to form a ring and the ring may be a spiro ring.

As specific examples of the structure of Ar, Structural Formulae (Ar-1) to (Ar-15) and the like can be given. Note that Structural Formulae (Ar-12) to (Ar-15) are specific examples of the structures in the case where Ar has a substituent. Further, Structural Formula (Ar-15) is a specific example in the case where the substituents are bonded to each other to form a spiro ring system.
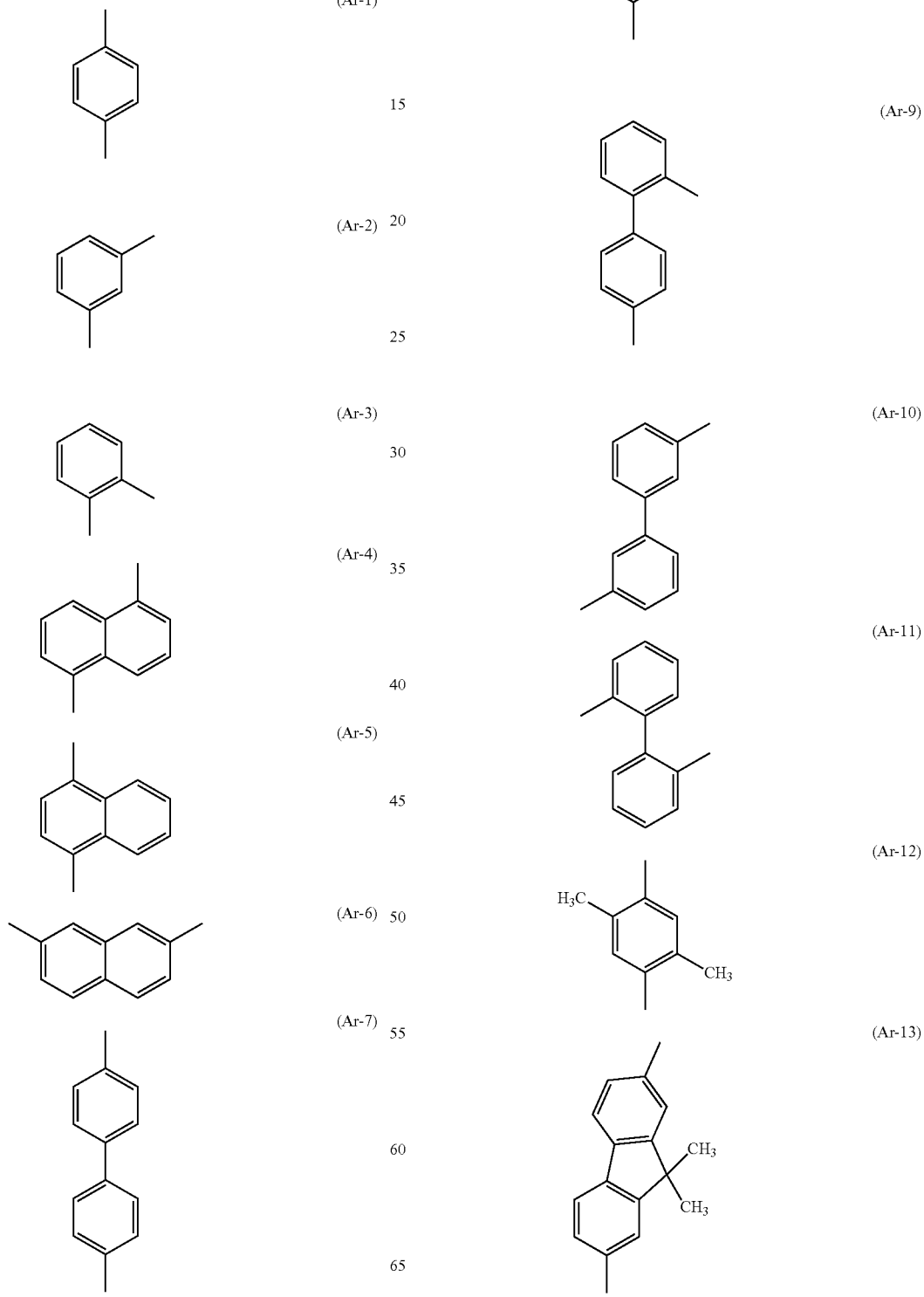

(Ar-14)

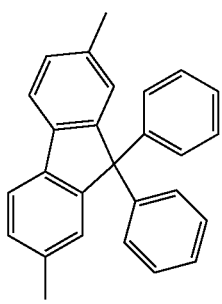

(Ar-15)

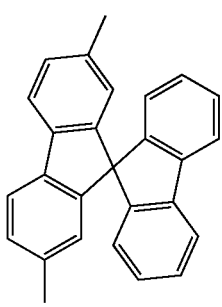

It is more preferable that Ar in the phenanthrene compound represented by General Formula (G1) be a phenylene group in terms of easiness of synthesis and because of its high triplet excitation energy. Therefore, it is more preferable that the phenanthrene compound according to one embodiment of the present invention be a phenanthrene compound represented by General Formula (G2).

(G2)

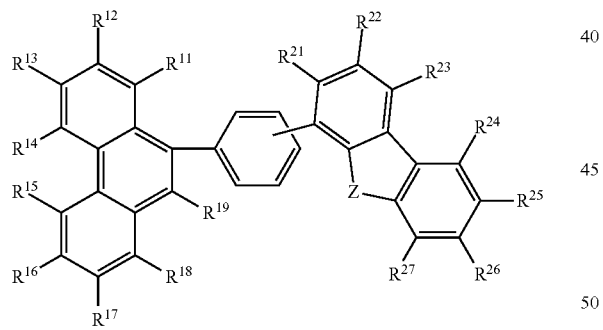

Note that in General Formula (G2), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Z represents a sulfur atom or an oxygen atom.

As specific examples of the structures of $R^{11}$ to $R^{19}$ and $R^{21}$ to $R^{27}$ in General Formula (G2), Structural Formulae (R-1) to (R-23) and the like can be given.

As specific examples of the phenanthrene compound represented by General Formula (G1), phenanthrene compounds represented by Structural Formulae (100) to (171) and Structural Formulae (200) to (271) can be given. However, the present invention is not limited to these.

(100)

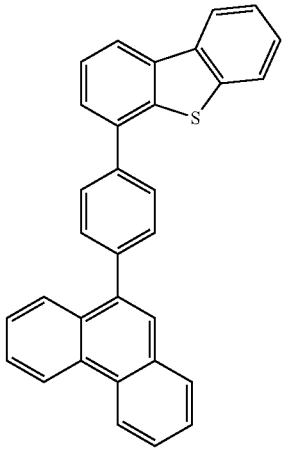

(101)

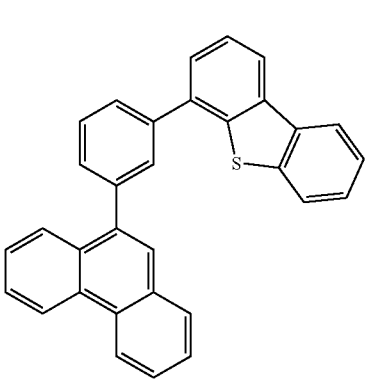

(102)

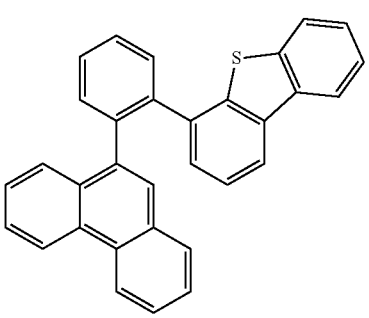

(103)

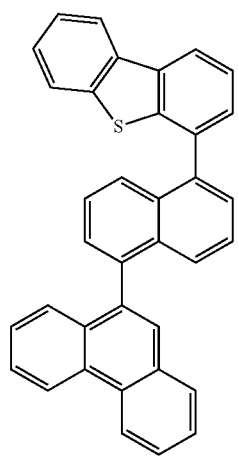

(104)
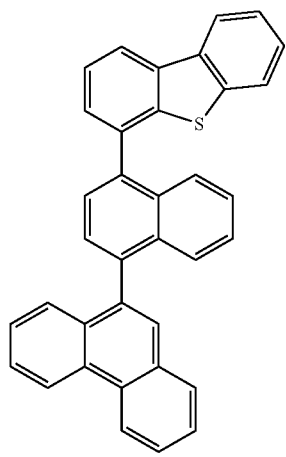
(105)
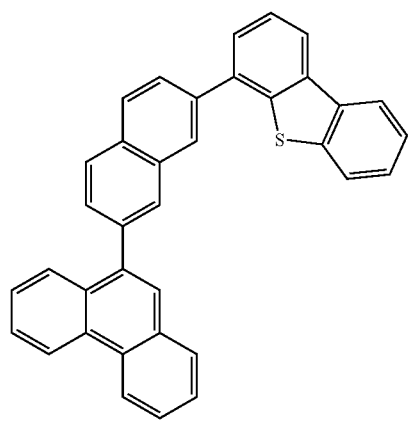
(106)
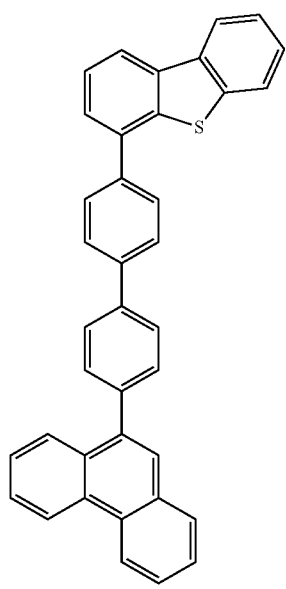
(107)
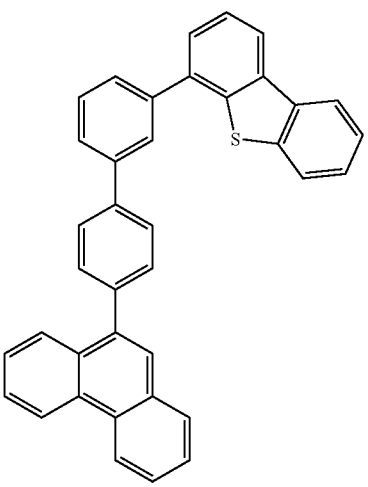
(108)
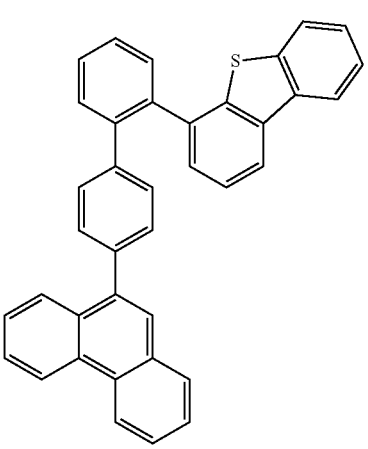
(109)

(110)
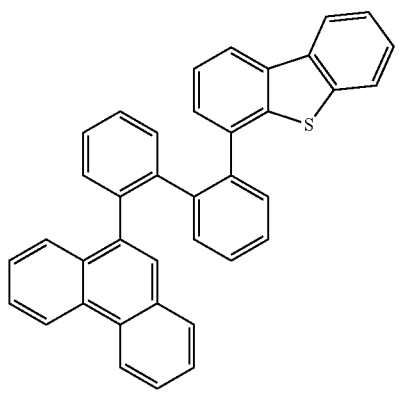
(111)
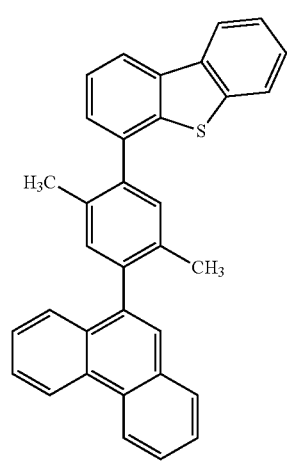
(112)
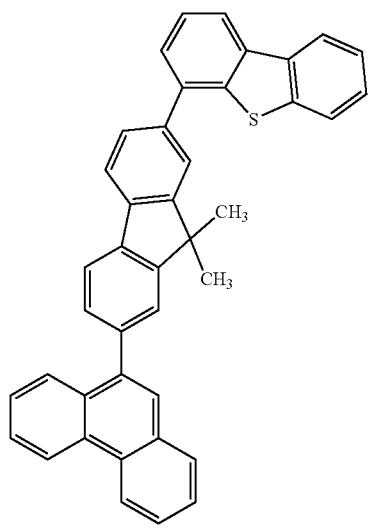
(113)
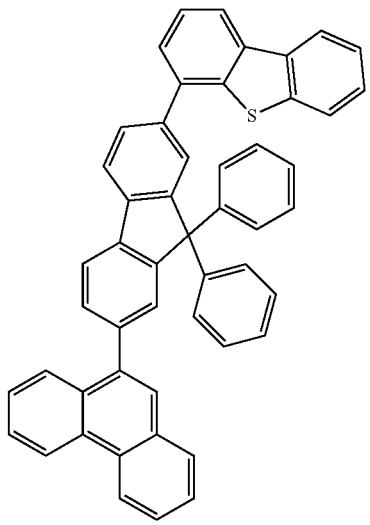
(114)
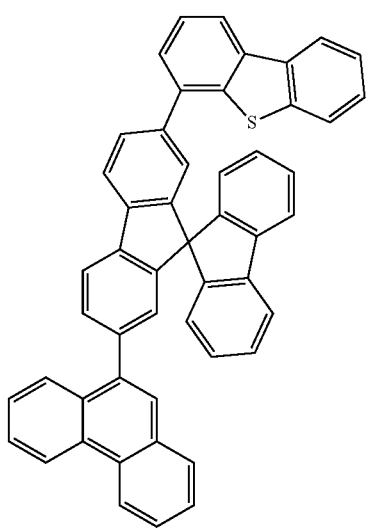
(115)
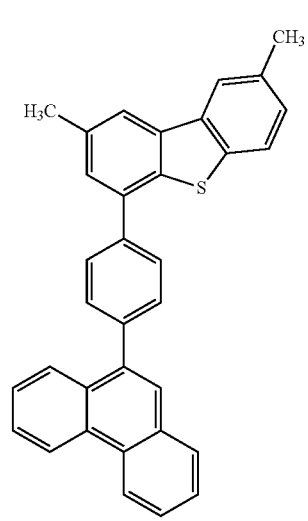

(116)
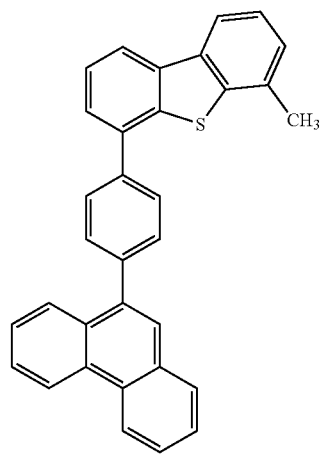
(117)
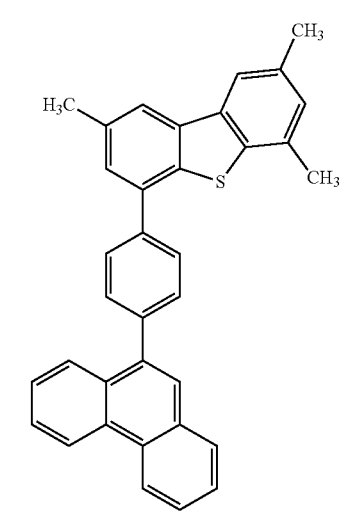
(118)
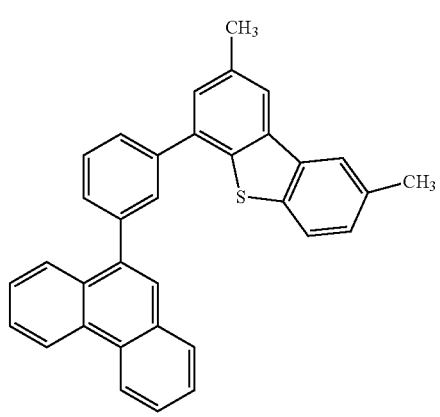
(119)
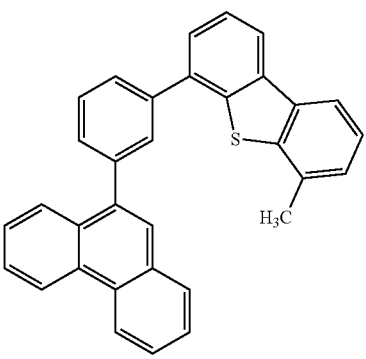
(120)
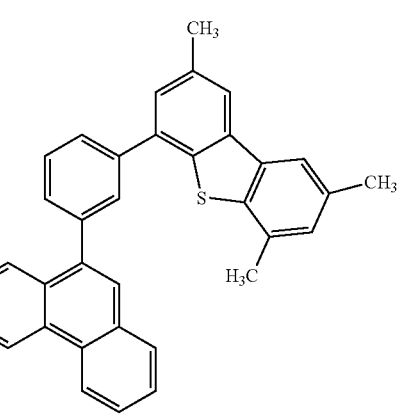
(121)
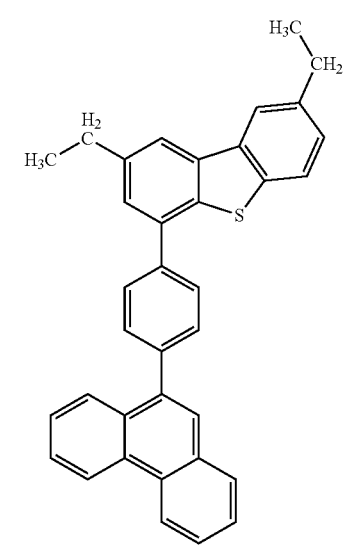

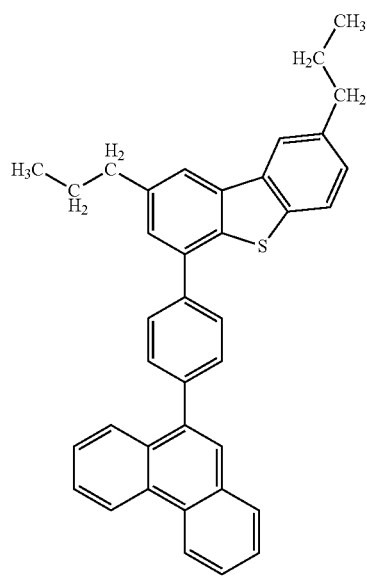
(122)
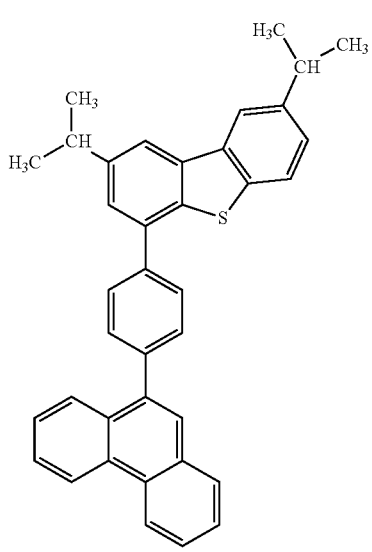
(123)
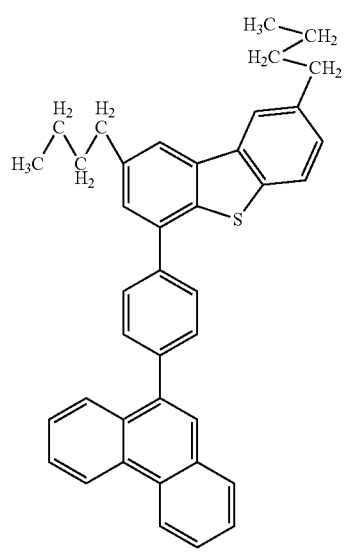
(124)
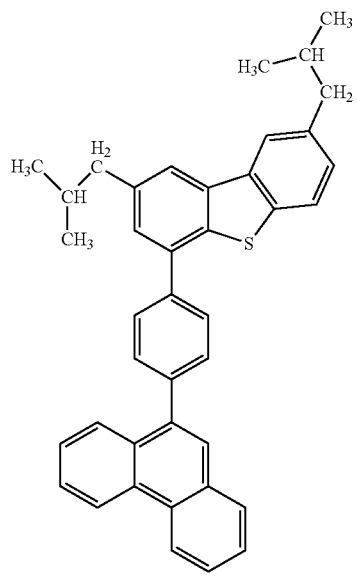
(125)
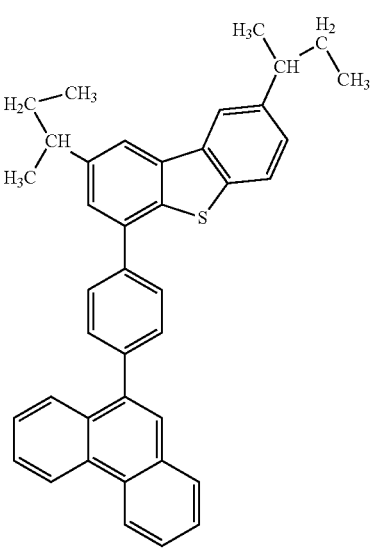
(126)
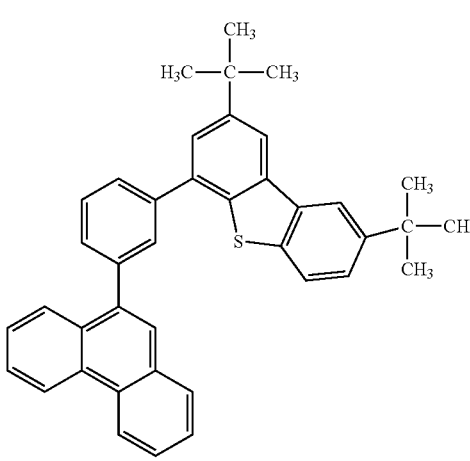
(127)

-continued
(128)
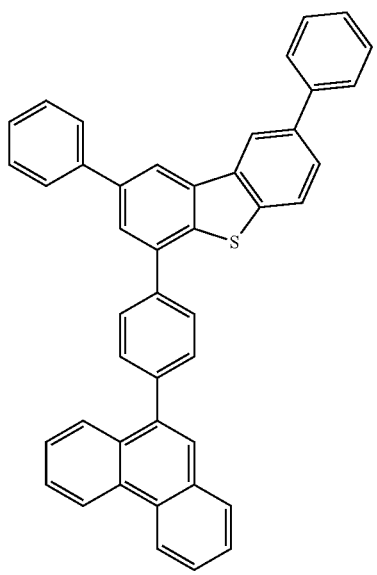
(129)
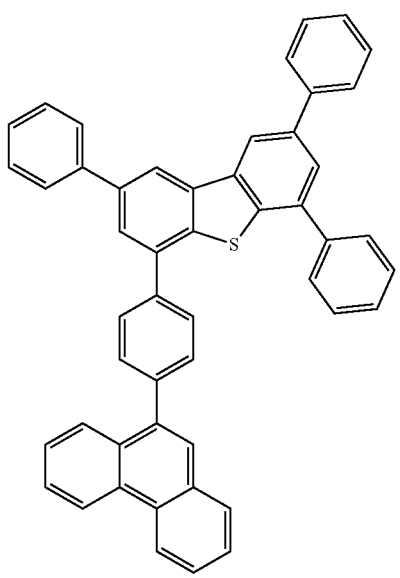
(130)
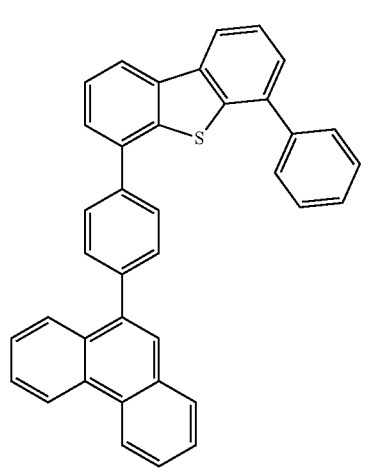
(131)
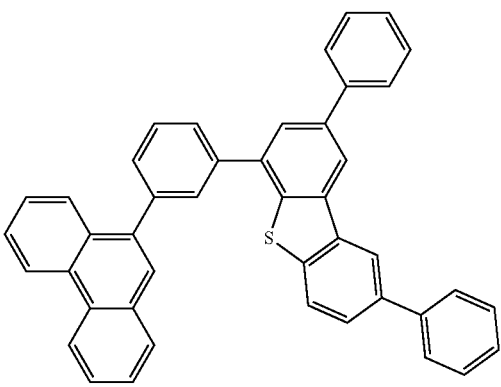
(132)
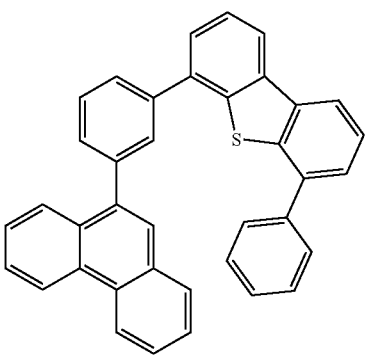
(133)
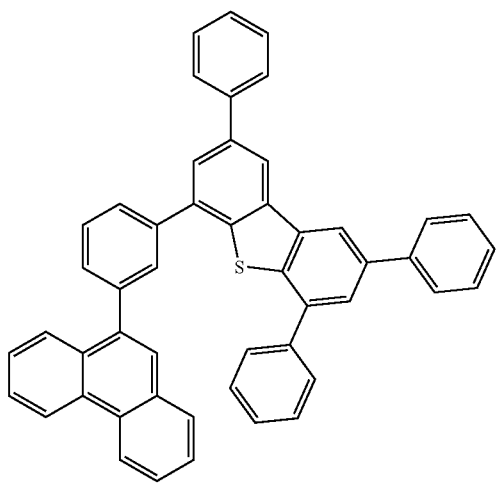

(134)
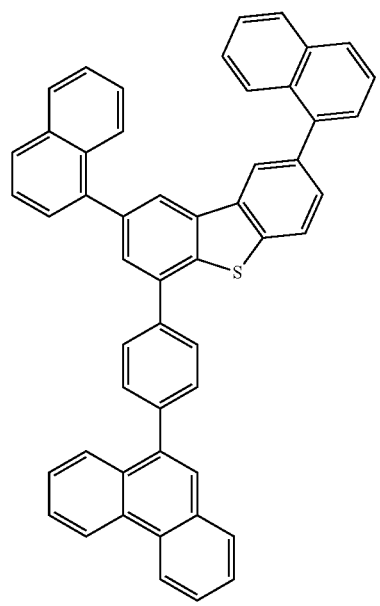
(136)
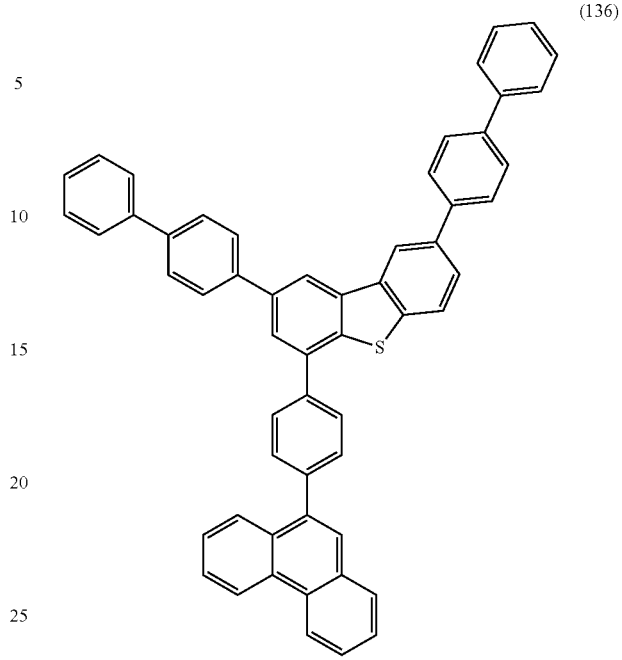
(135)
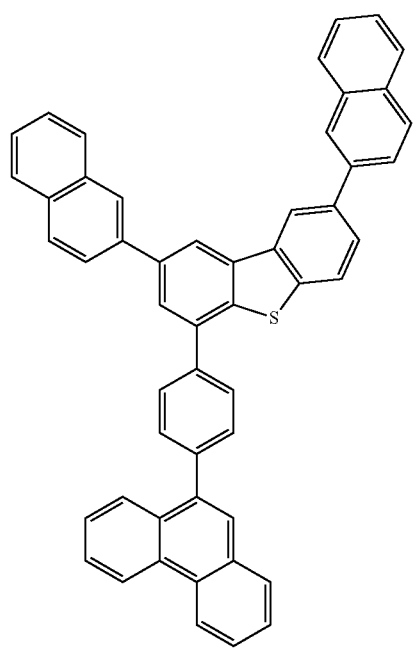
(137)
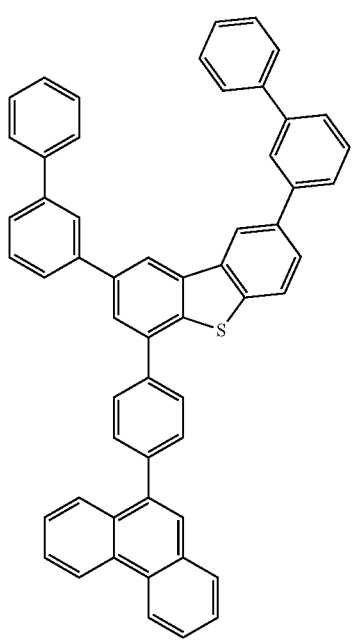

(138)
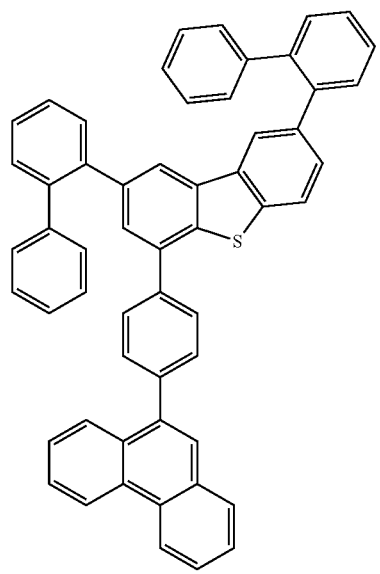
(139)
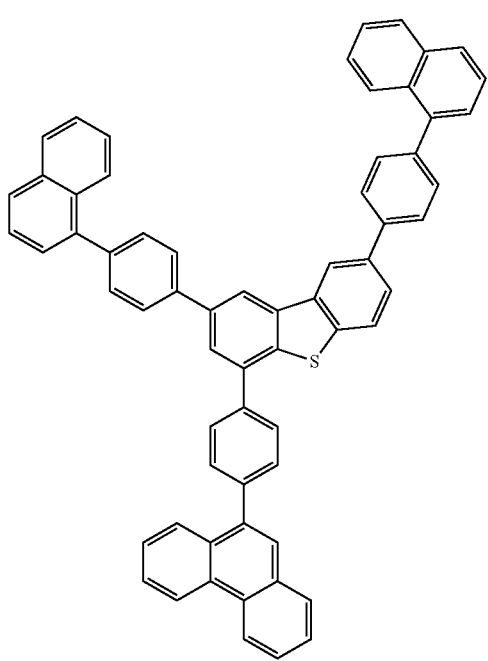
(140)
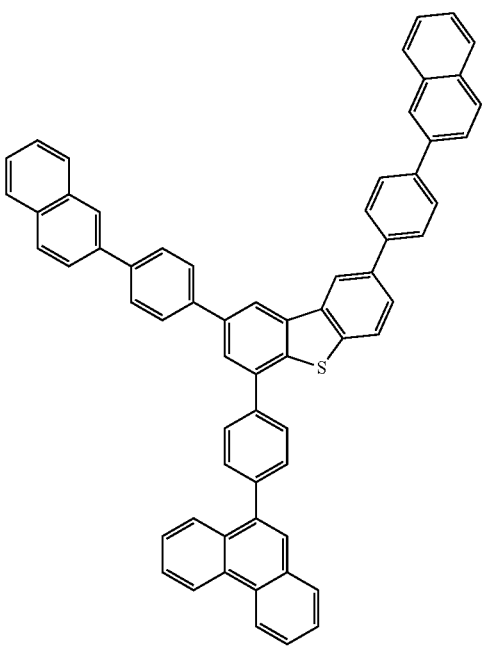
(141)
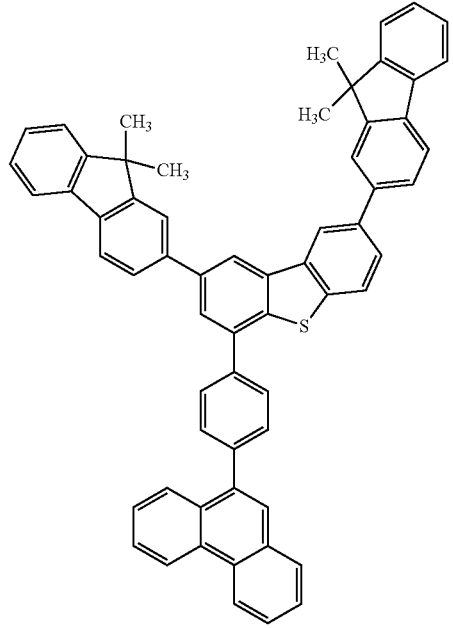

(142) 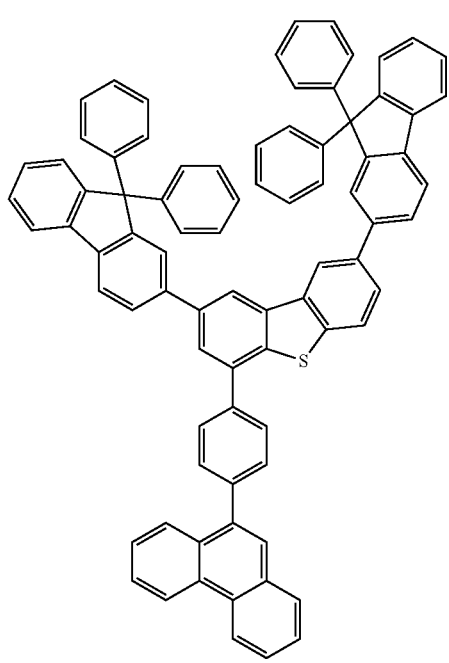
(143) 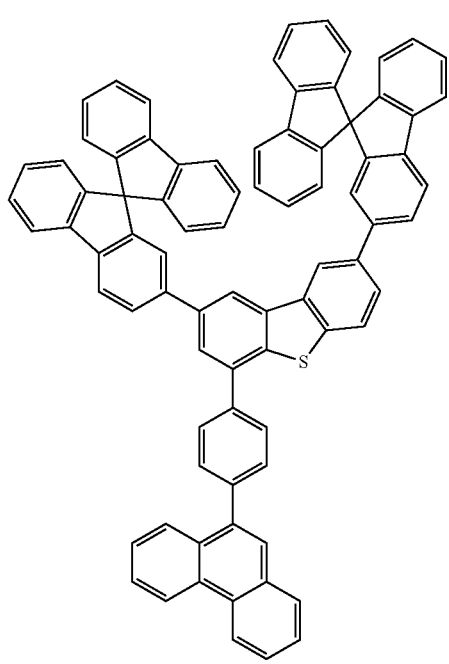
(144) 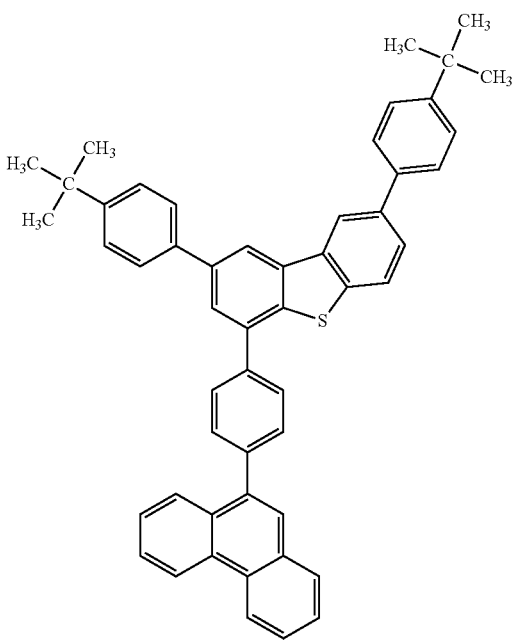
(145) 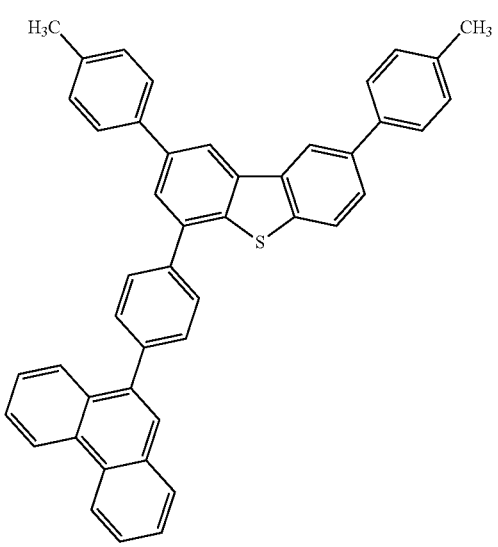

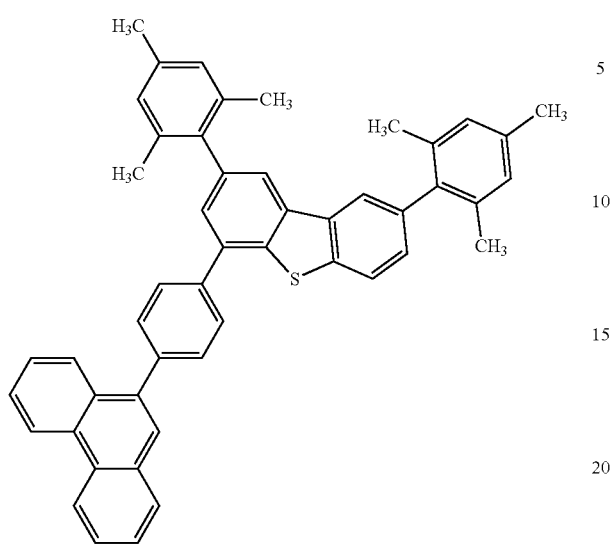
(146)
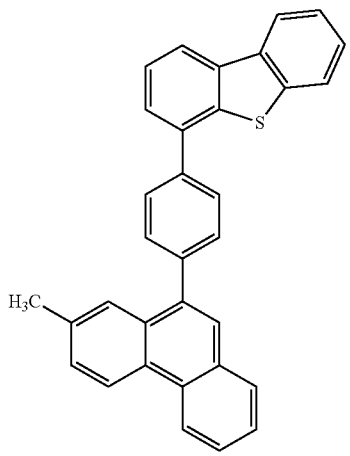
(149)
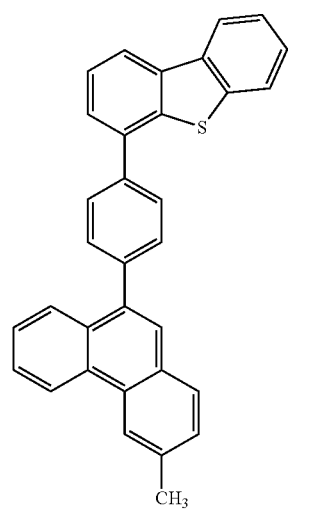
(147)
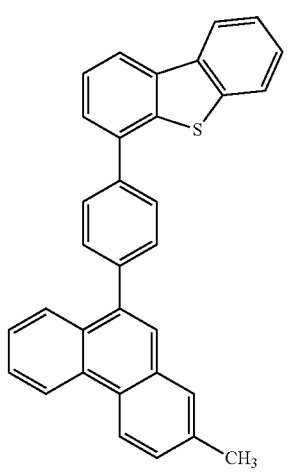
(150)
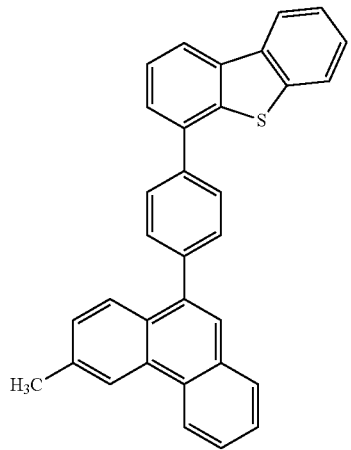
(148)
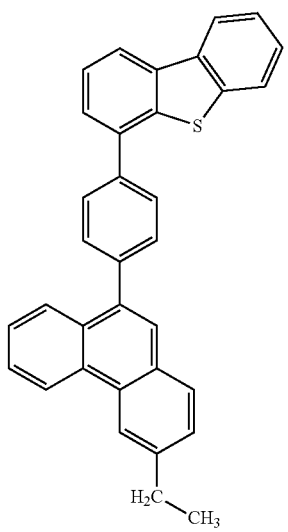
(151)

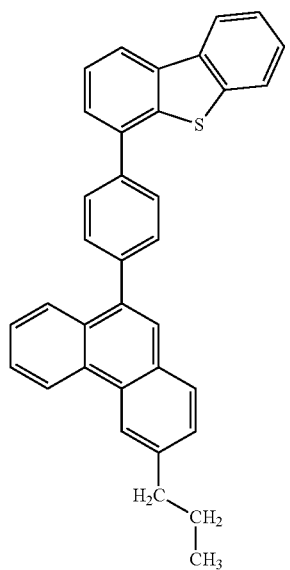
(152)
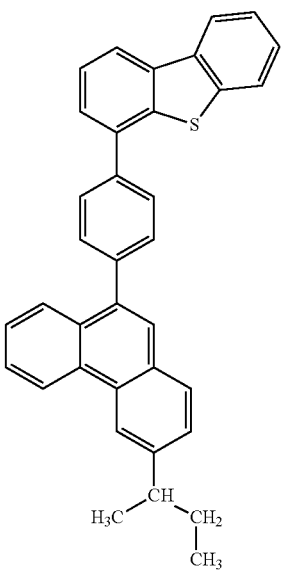
(155)
(153)
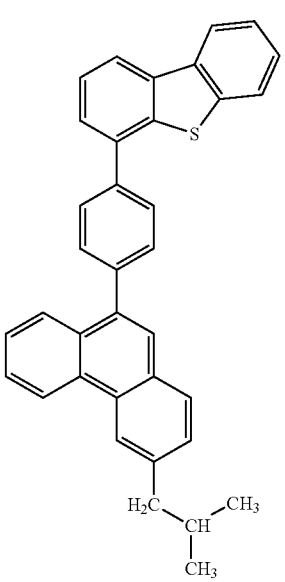
(156)
(154)
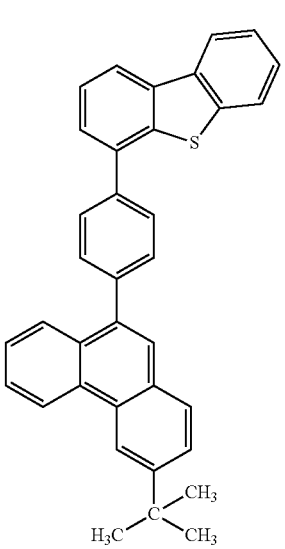
(157)

(158)
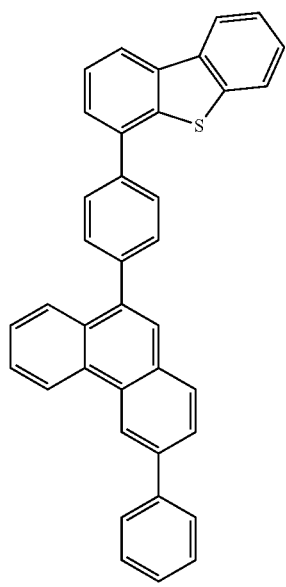
(160)
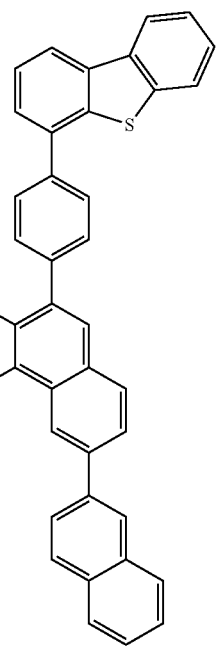
(159)
(161)
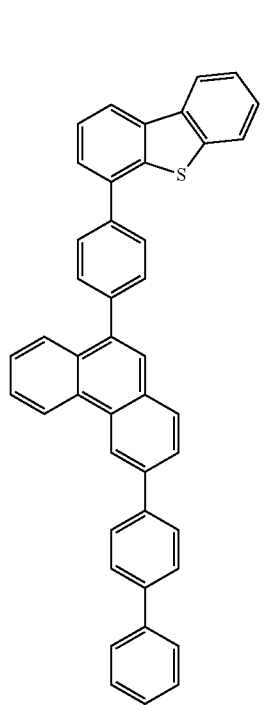

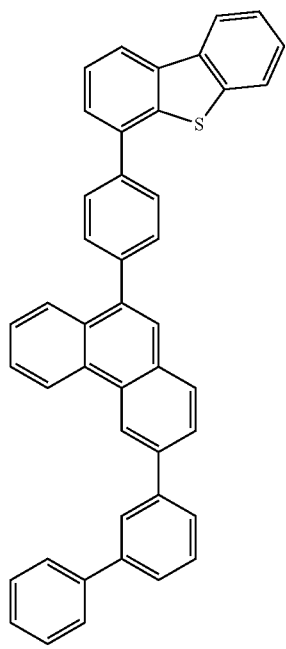
(162)
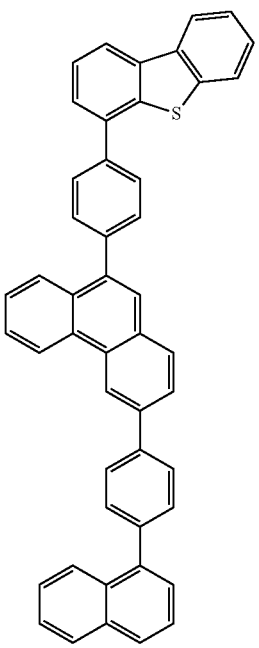
(164)
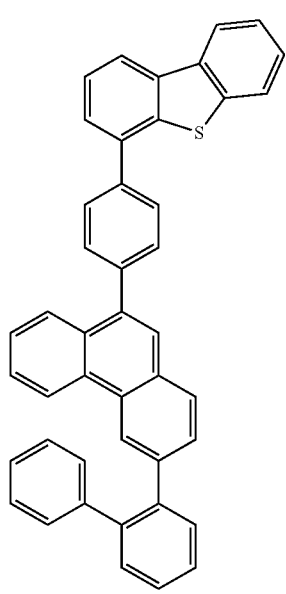
(163)
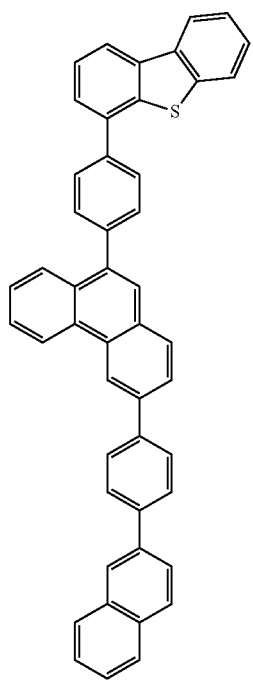
(165)

(166)
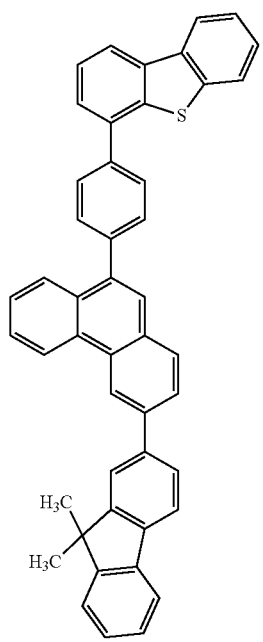
(167)
(168)
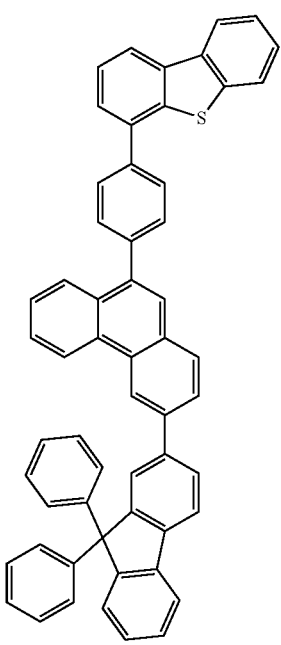
(169)
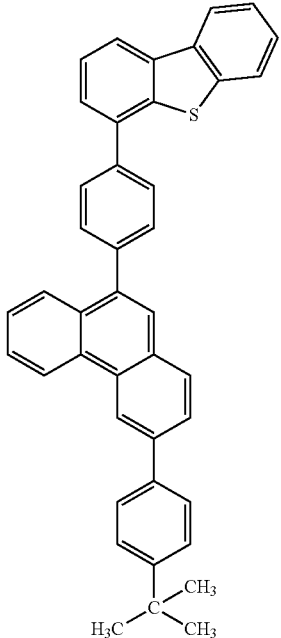

-continued
(170)
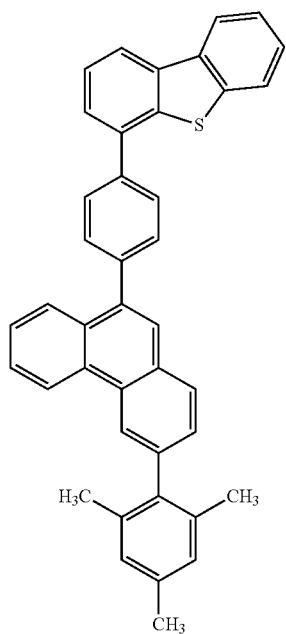
(171)
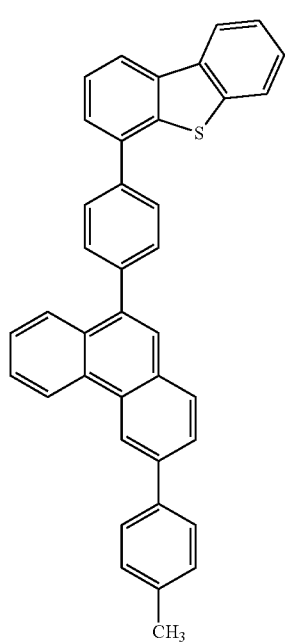
-continued
(200)
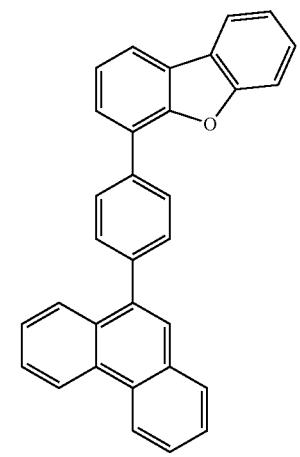
(201)
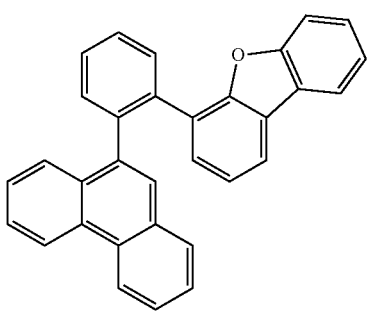
(202)
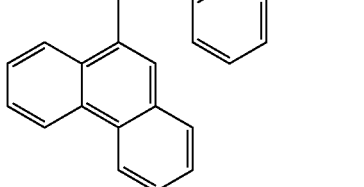
(203)
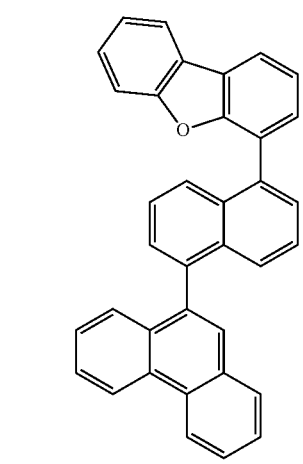

(204)
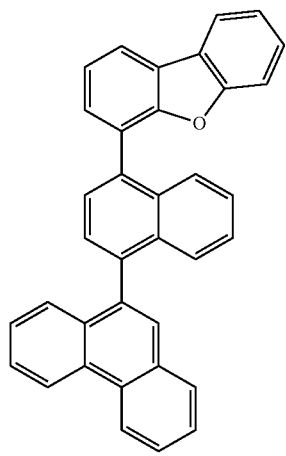
(205)
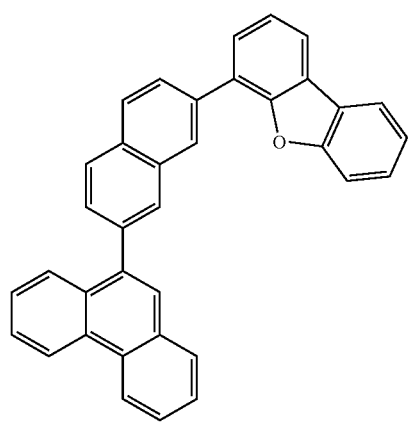
(206)
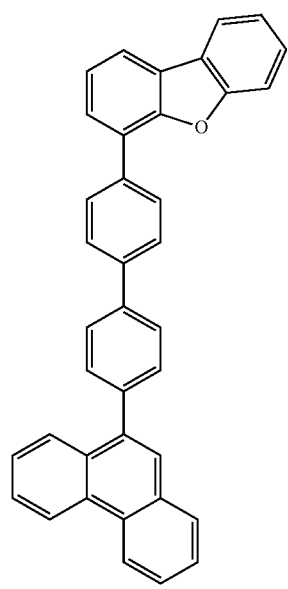
(207)
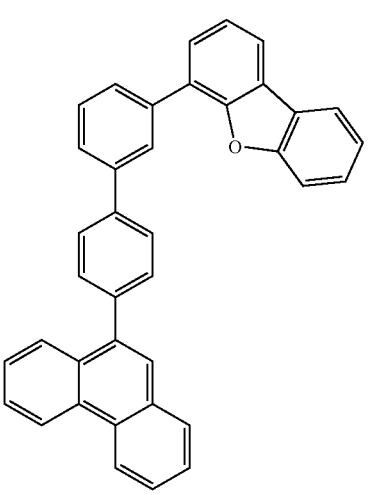
(208)
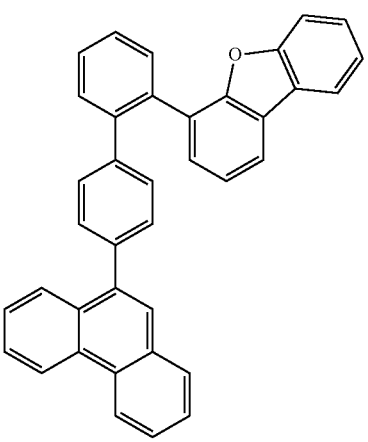
(209)
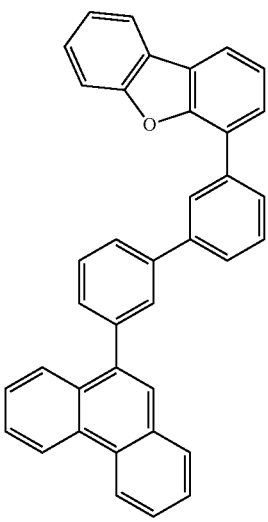

(210)
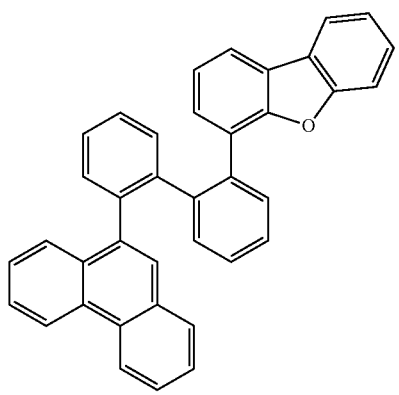
(211)
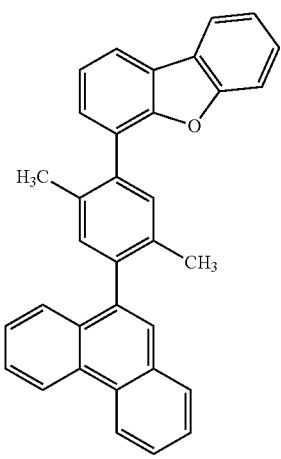
(212)
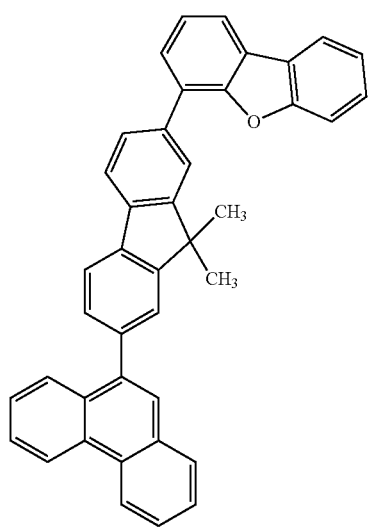
(213)
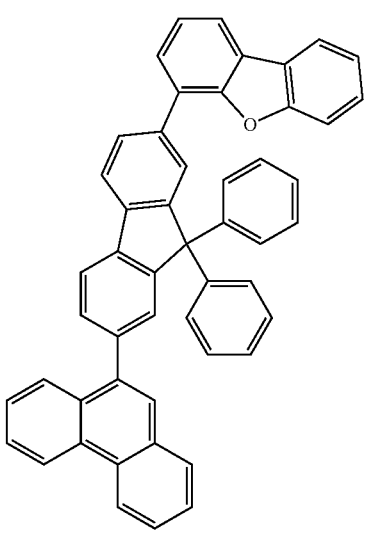
(214)
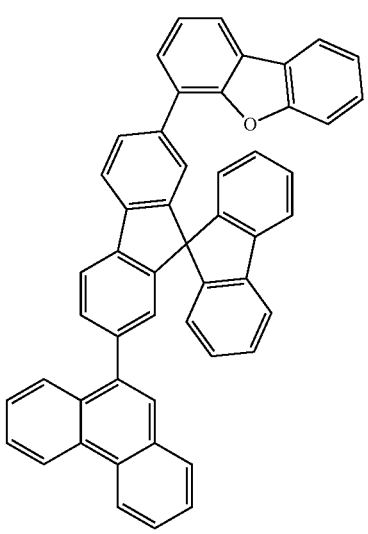
(215)
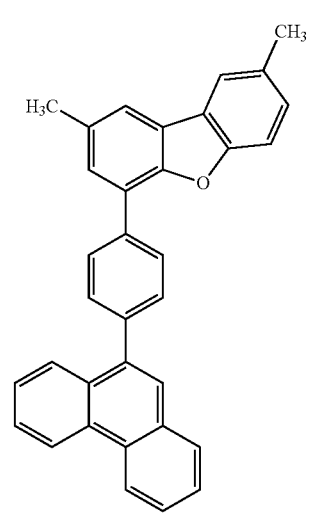

(216)
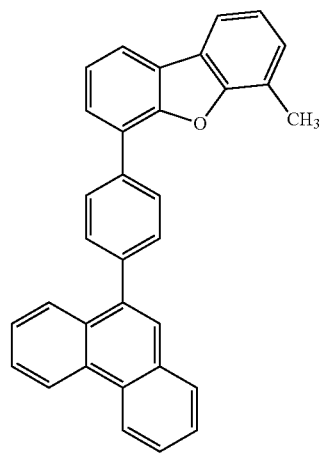
(217)
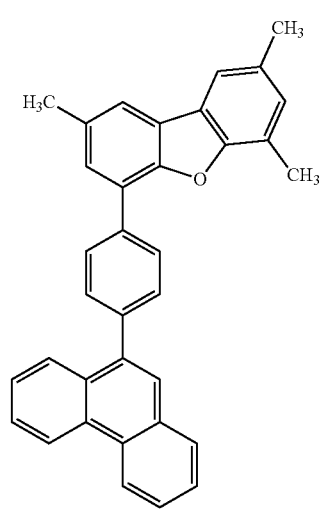
(218)
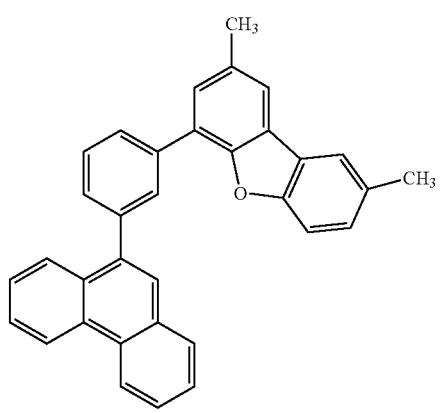
(219)
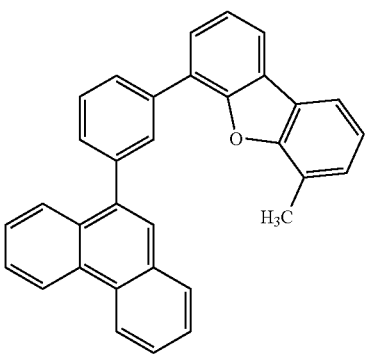
(220)
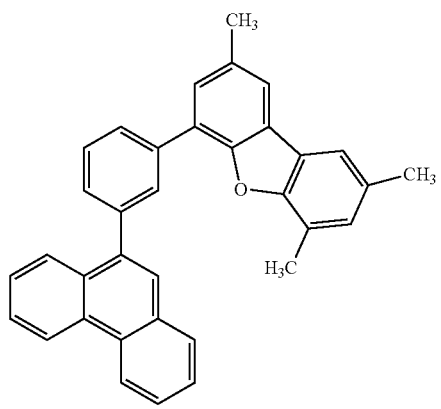
(221)
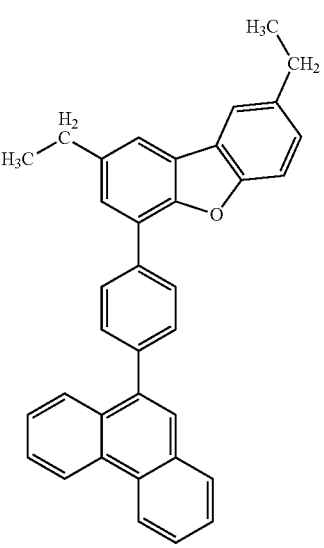

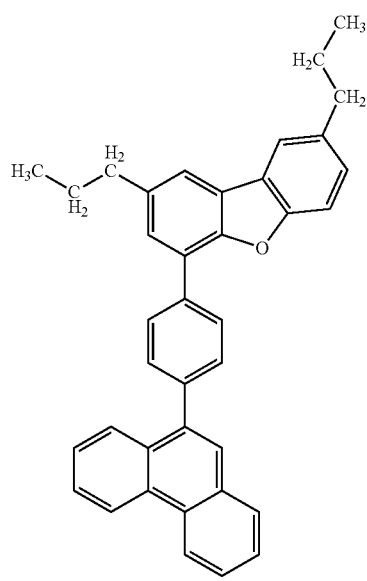
(222)
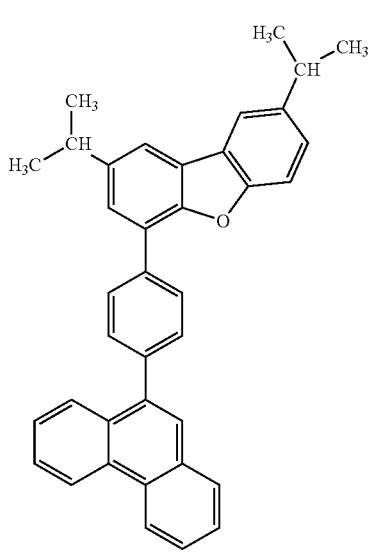
(223)
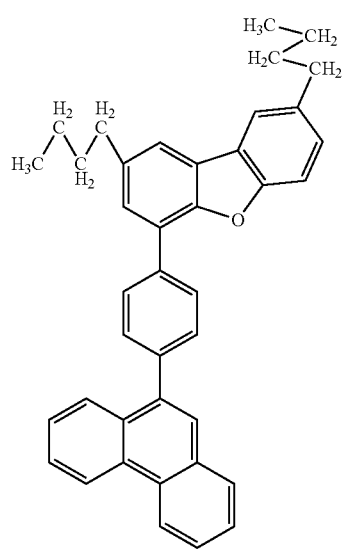
(224)
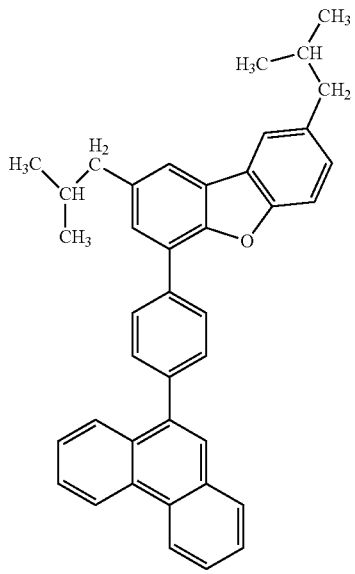
(225)
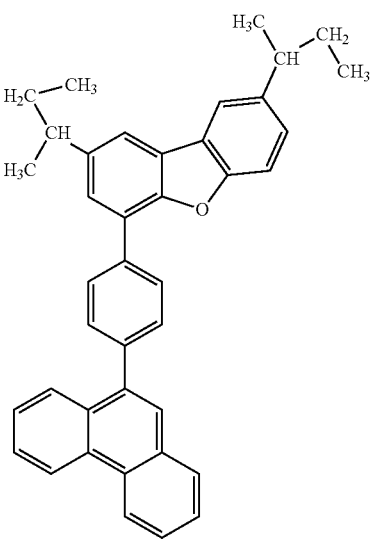
(226)
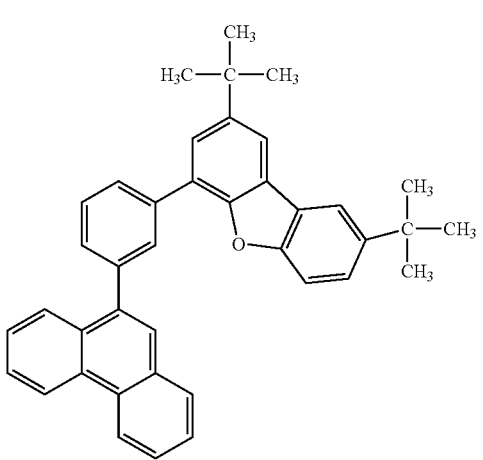
(227)

(228)
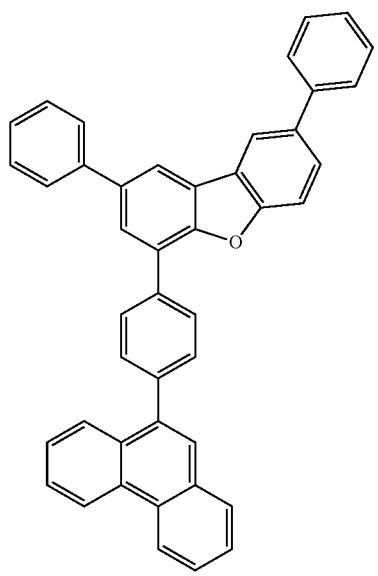
(229)
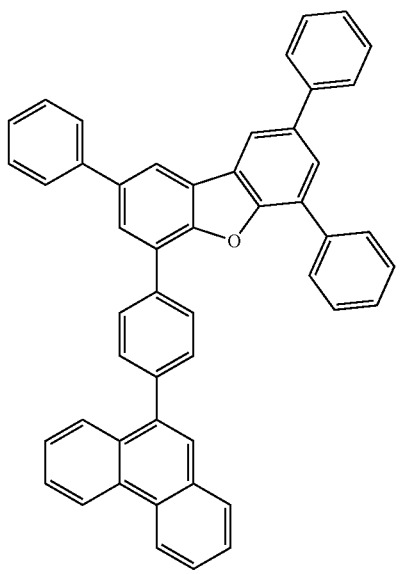
(230)
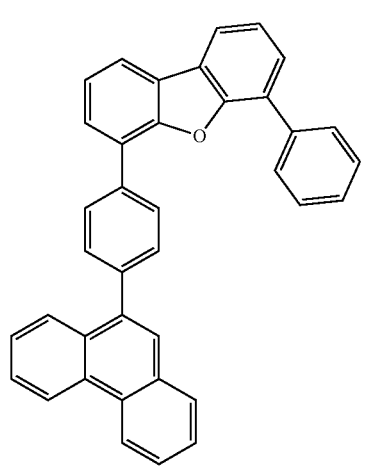
(231)
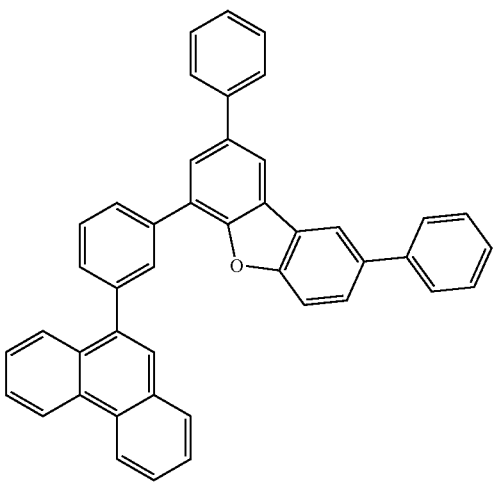
(232)
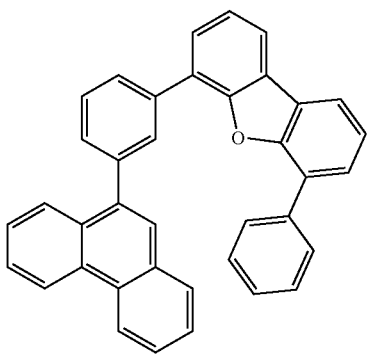
(233)
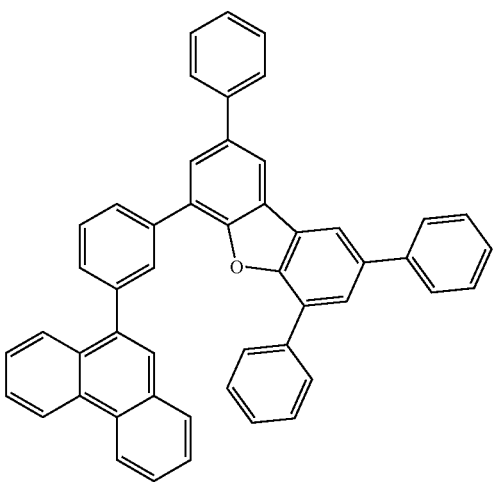

(234)
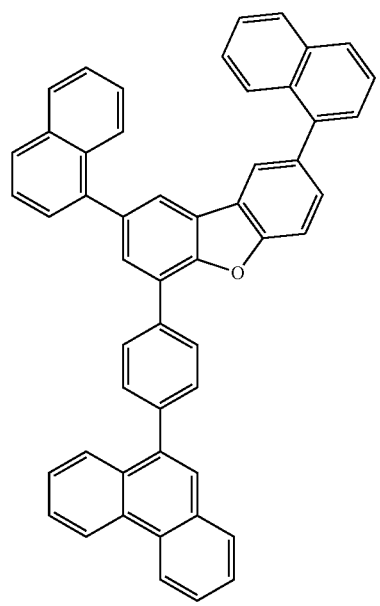
(236)
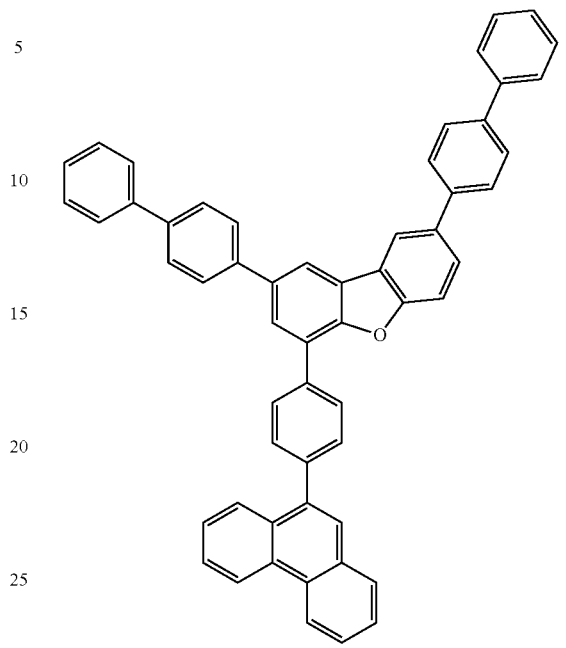
(235)
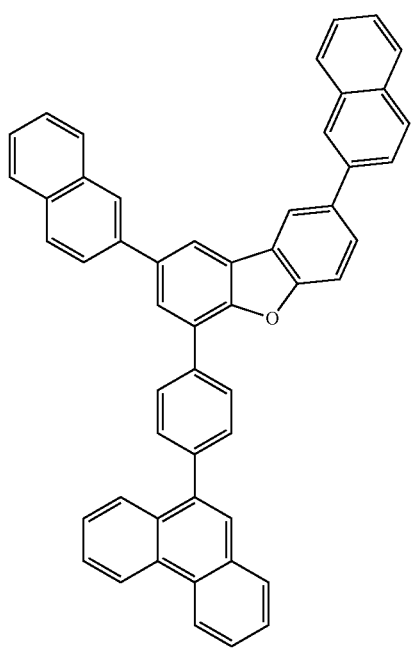
(237)
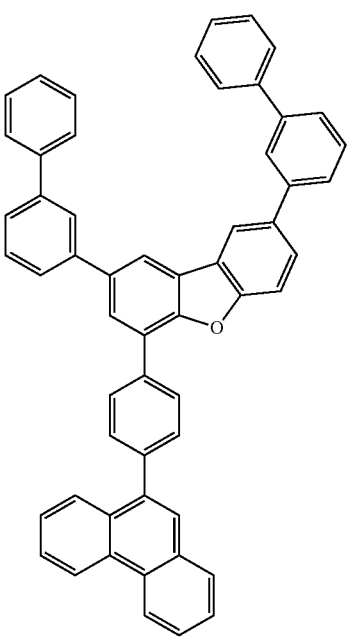

(238)
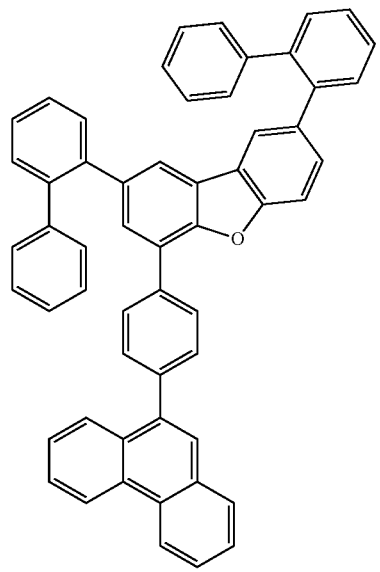
(240)
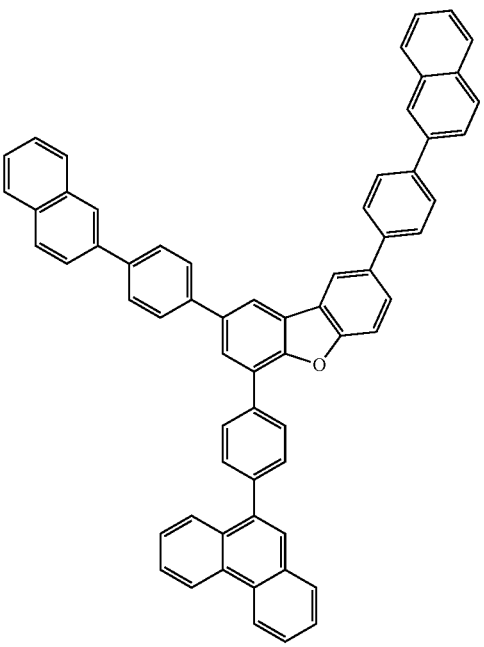
(239)
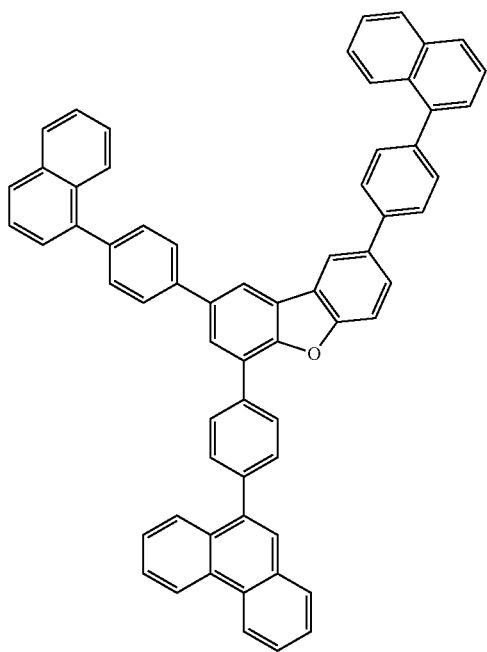
(241)
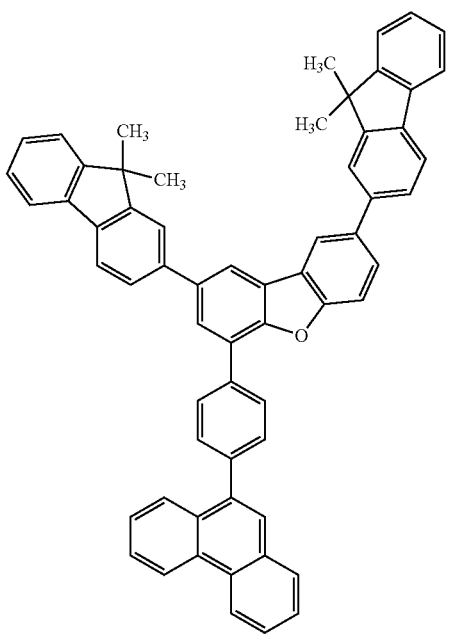

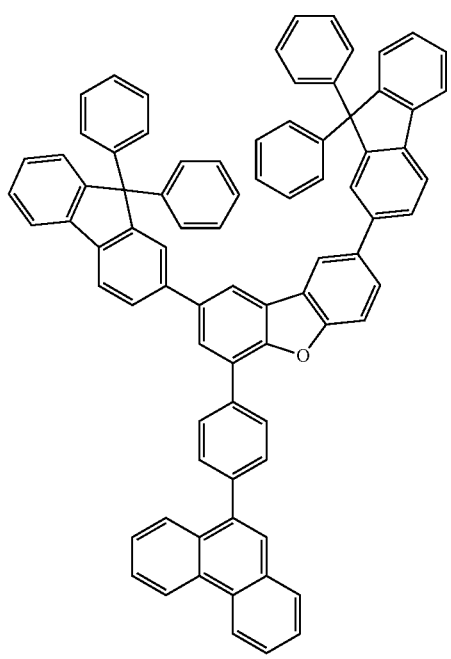
(242)
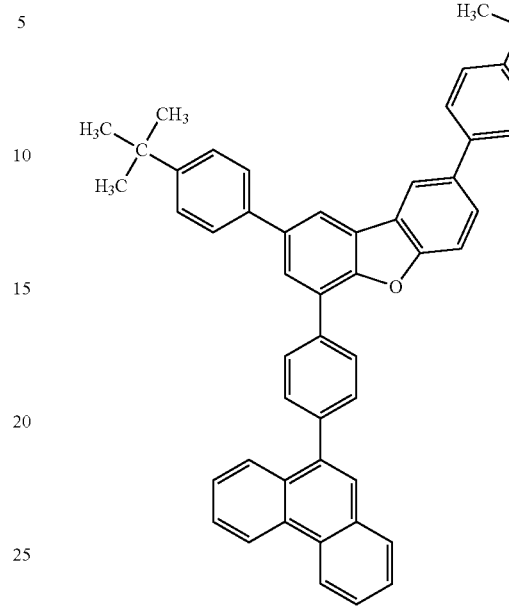
(244)
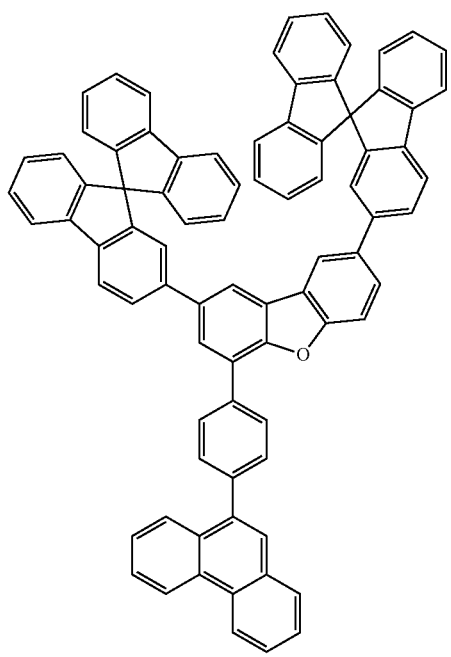
(243)
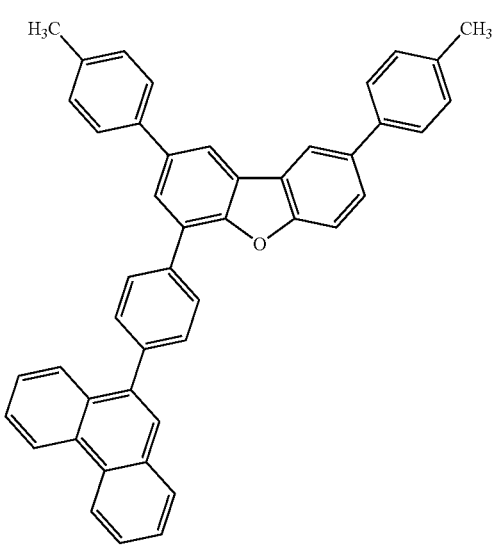
(245)

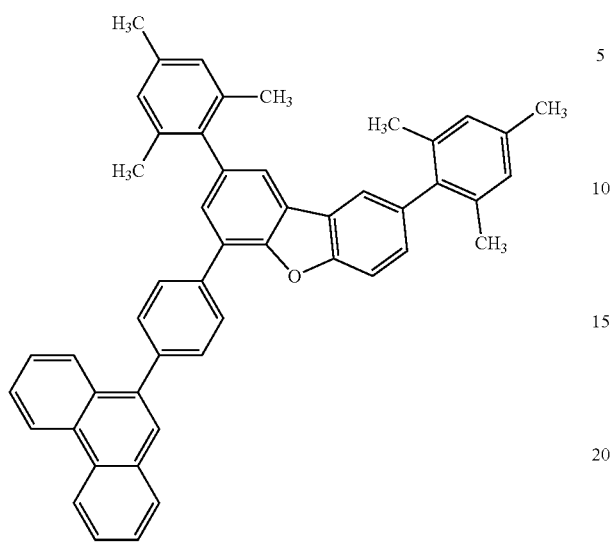
(246)
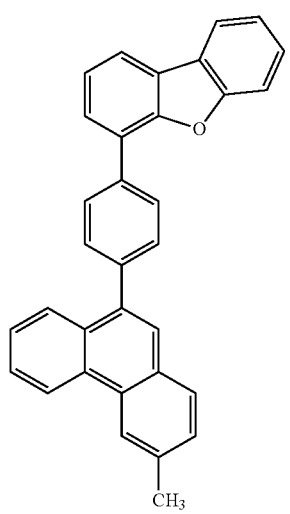
(247)
(248)
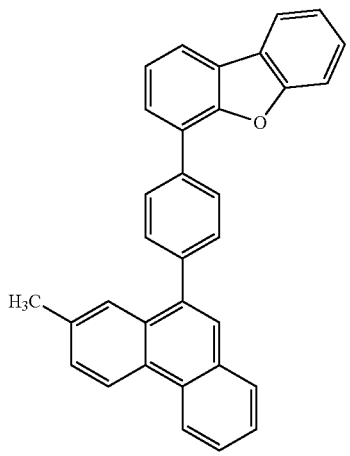
(249)
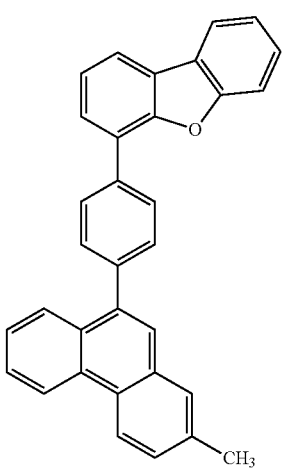
(250)
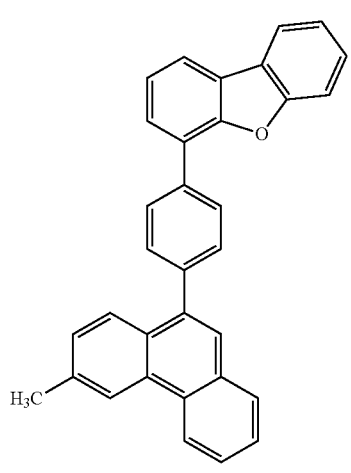
(251)

(252) 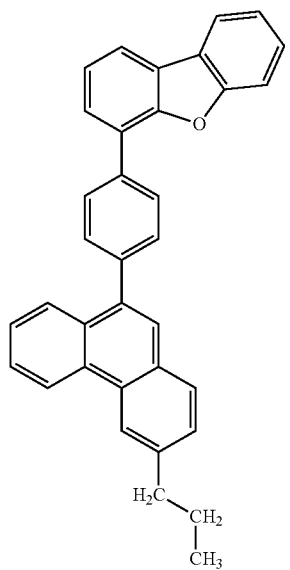
(253) 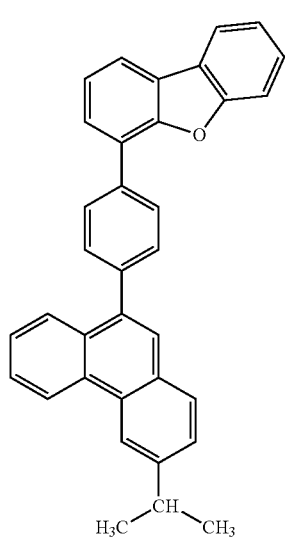
(254) 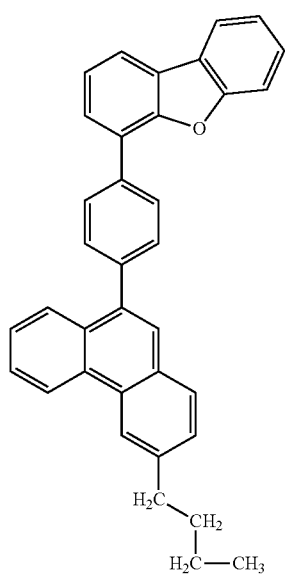
(255) 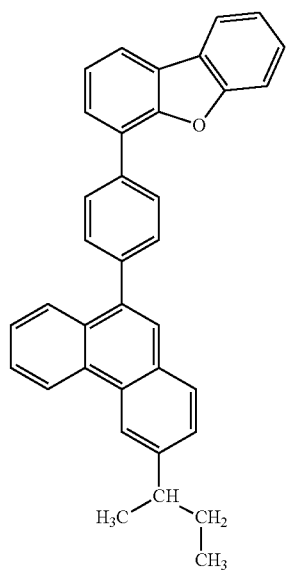
(256) 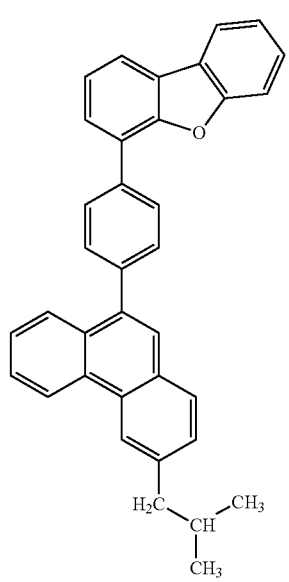
(257) 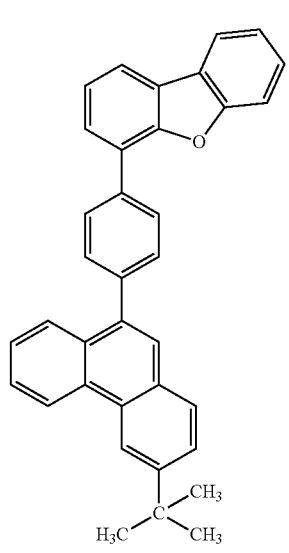

(258)
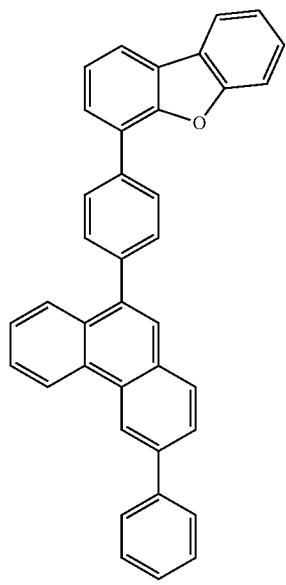
(259)
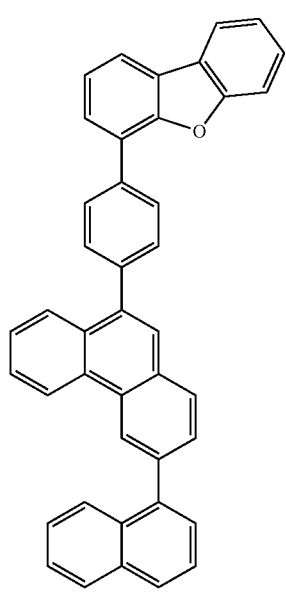
(260)
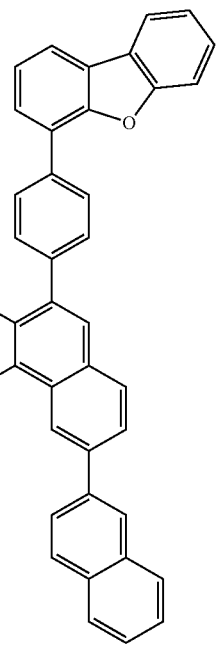
(261)
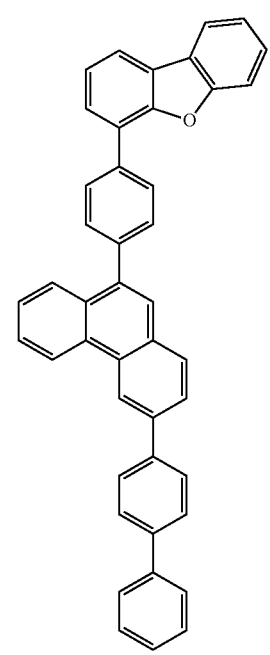

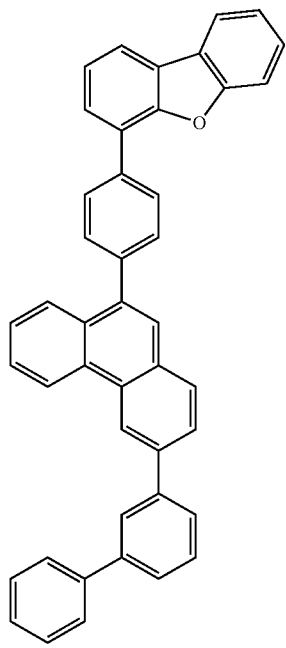
(262)
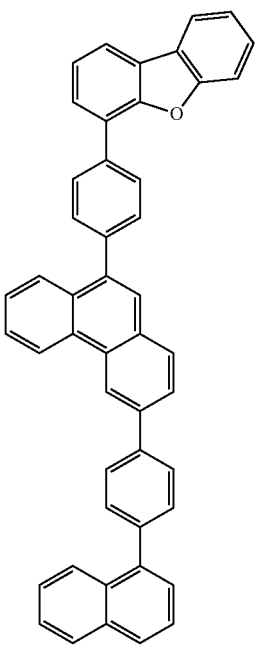
(264)
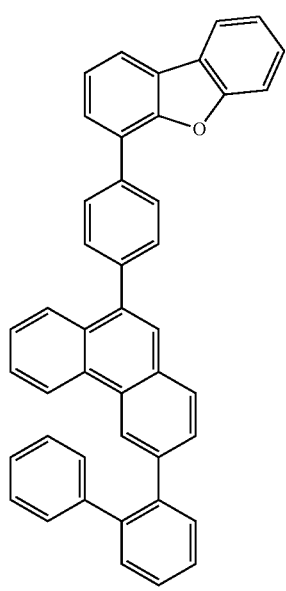
(263)
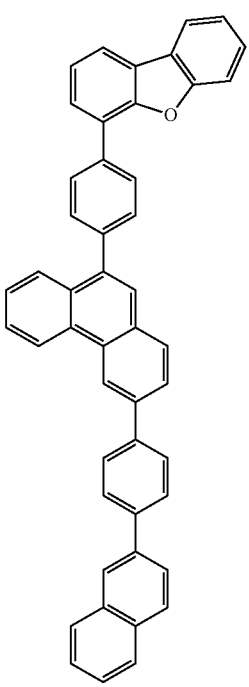
(265)

(266)
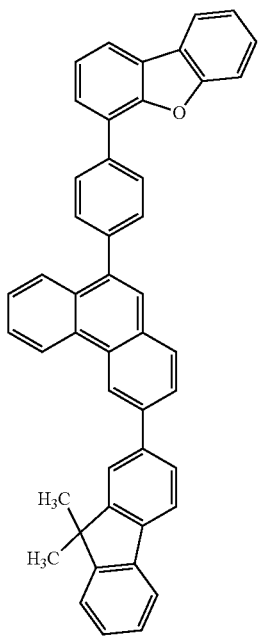
(267)
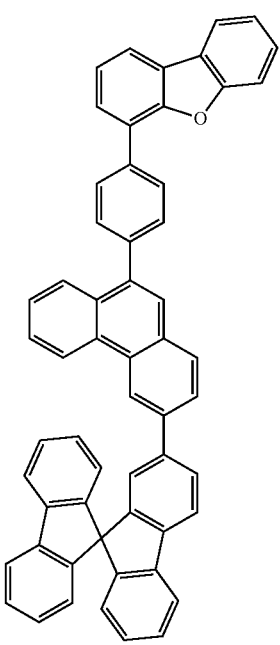
(268)
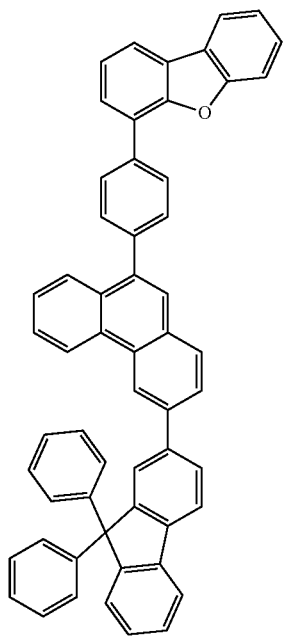
(269)
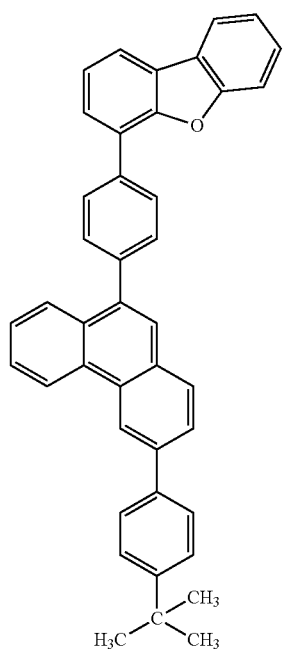

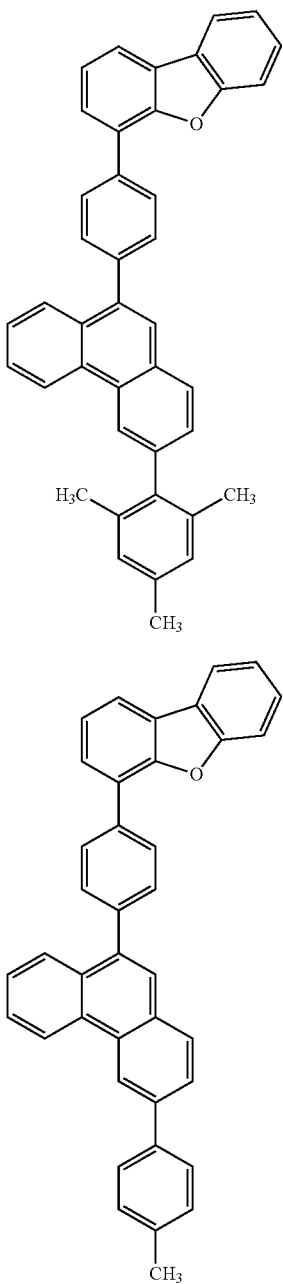

(270)

(271)

A variety of reactions can be used for a synthesis method of the phenanthrene compound of this embodiment. For example, the phenanthrene compound can be synthesized by a synthesis reaction in Synthesis Method 1 or Synthesis Method 2.

<Synthesis Method 1>

As shown in Synthesis Scheme (A-1), a halide of a phenanthrene derivative (Compound 1) is coupled with an organoboron compound of a dibenzofuran derivative or a dibenzothiophene derivative (Compound 2) or with boronic acid of a dibenzofuran derivative or a dibenzothiophene derivative (Compound 2) by the Suzuki-Miyaura Reaction, whereby the phenanthrene compound represented by General Formula (G1) can be obtained.

Note that in Synthesis Scheme (A-1), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Ar represents a substituted or unsubstituted arylene group having 6 to 13 carbon atoms. Z represents a sulfur atom or an oxygen atom. Further, $R^{50}$ and $R^{51}$ separately represent either hydrogen or an alkyl group having 1 to 6 carbon atoms, and $R^{50}$ and $R^{51}$ may be bonded to each other to form a ring. X represents a halogen, preferably bromine or iodine.

Examples of a palladium catalyst that can be used in Synthesis Scheme (A-1) include palladium(II) acetate, tetrakis(triphenylphosphine)palladium(0), bis(triphenylphosphine)palladium(II) dichloride, and the like. Examples of a ligand of the palladium catalyst that can be used in Synthesis Scheme (A-1) include tri(ortho-tolyl)phosphine, triphenylphosphine, tricyclohexylphosphine, and the like.

Examples of a base that can be used in Synthesis Scheme (A-1) include an organic base such as sodium tert-butoxide, an inorganic base such as potassium carbonate or sodium carbonate, and the like. Examples of a solvent that can be used in Synthesis Scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. Note that a mixed solvent of toluene and water; a mixed solvent of toluene, ethanol, and water; or a mixed solvent of water and ether such as ethylene glycol dimethyl ether is more preferable.

As a coupling reaction shown in Synthesis Scheme (A-1), the Suzuki-Miyaura Reaction using the organoboron compound or boronic acid represented by Compound 2 may be replaced with a cross coupling reaction using an organoaluminum compound, an organozirconium compound, an organozinc compound, an organotin compound, or the like. Further, a triflate group or the like may be used other than halogen in the coupling reaction.

Further, the phenanthrene compound represented by General Formula (G1) may be synthesized in such a manner that an organoboron compound of a phenanthrene derivative or boronic acid of a phenanthrene derivative, which is used instead of Compound 1, is coupled with a halide of a dibenzofuran derivative or a dibenzothiophene derivative or with a dibenzofuran derivative or a dibenzothiophene derivative having a triflate group as a substituent, which is used instead of Compound 2, in the Suzuki-Miyaura Reaction shown in Synthesis Scheme (A-1).

<Synthesis Method 2>

As shown in Synthesis Scheme (B-1), a halide of a phenanthrene derivative (Compound 3) is coupled with an organoboron compound of a dibenzofuran derivative or a dibenzothiophene derivative (Compound 4) or with boronic acid of a dibenzofuran derivative or a dibenzothiophene derivative (Compound 4) by the Suzuki-Miyaura Reaction, whereby the phenanthrene compound represented by General Formula (G1) can be obtained.

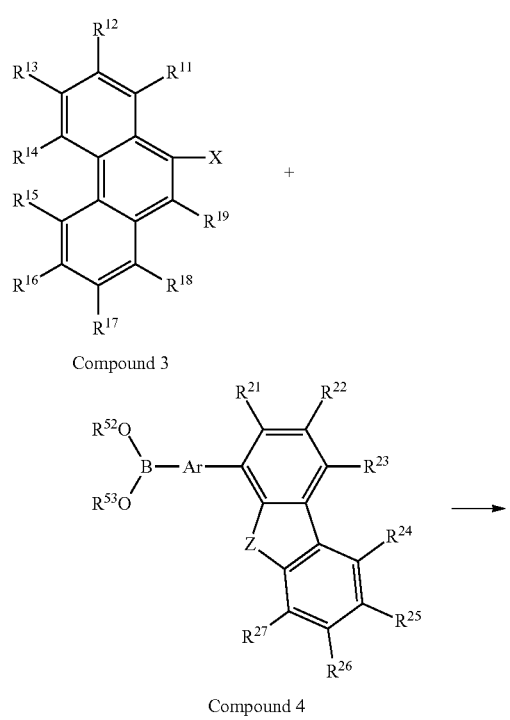

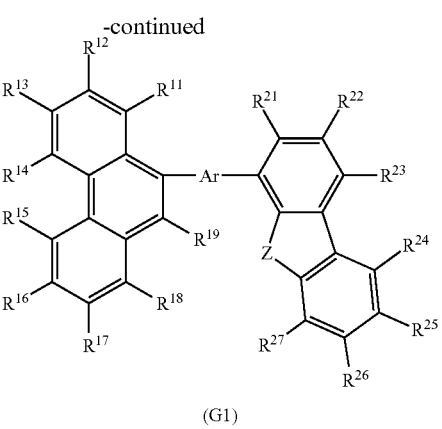

Note that in Synthesis Scheme (B-1), $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms. Ar represents a substituted or unsubstituted arylene group having 6 to 13 carbon atoms. Z represents a sulfur atom or an oxygen atom. $R^{52}$ and $R^{53}$ separately represent either hydrogen or an alkyl group having 1 to 6 carbon atoms, and $R^{52}$ and $R^{53}$ may be bonded to each other to form a ring. X represents a halogen, preferably bromine or iodine.

Examples of a palladium catalyst that can be used in Synthesis Scheme (B-1) include palladium(II) acetate, tetrakis (triphenylphosphine)palladium(0), bis(triphenylphosphine) palladium(II) dichloride, and the like. Examples of a ligand of the palladium catalyst that can be used in Synthesis Scheme (B-1) include tri(ortho-tolyl)phosphine, triphenylphosphine, tricyclohexylphosphine, and the like.

Examples of a base that can be used in Synthesis Scheme (B-1) include an organic base such as sodium tert-butoxide, an inorganic base such as potassium carbonate or sodium carbonate, and the like. Examples of a solvent that can be used in Synthesis Scheme (B-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. Note that a mixed solvent of toluene and water; a mixed solvent of toluene, ethanol, and water; or a mixed solvent of water and ether such as ethylene glycol dimethyl ether is more preferable.

As a coupling reaction shown in Synthesis Scheme (B-1), the Suzuki-Miyaura Reaction using the organoboron compound or boronic acid represented by Compound 4 may be replaced with a cross coupling reaction using an organoaluminum compound, an organozirconium compound, an organozinc compound, an organotin compound, or the like. Further, a triflate group or the like may be used other than halogen in the coupling reaction.

Further, the phenanthrene compound represented by General Formula (G1) may be synthesized in such a manner that an organoboron compound of a phenanthrene derivative or boronic acid of a phenanthrene derivative, which is used instead of Compound 3, is coupled with a halide of a dibenzofuran derivative or a dibenzothiophene derivative or with dibenzofuran derivative or a dibenzothiophene derivative having a triflate group as a substituent, which is used instead of Compound 4, in the Suzuki-Miyaura Reaction shown in Synthesis Scheme (B-1).

Thus, the phenanthrene compound of this embodiment can be synthesized.

The phenanthrene compound of this embodiment has a bipolar property, and thus can be suitably used as a material of a hole-transport layer or an electron-transport layer of a light-emitting element. Further, a composite material in which the phenanthrene compound of this embodiment (an electron donor) and an electron acceptor are mixed can be used for a hole-injection layer of a light-emitting element. Note that the electron acceptor or the electron donor is at least capable of donating and accepting electrons with the assistance of an electric field.

The phenanthrene compound of this embodiment is also suitable as a host material in a light-emitting layer of a light-emitting element. In other words, when a light-emitting substance (hereinafter, also referred to as a "dopant") having a narrower band gap than the phenanthrene compound of this embodiment is added to a layer formed of the phenanthrene compound, light can be emitted from the dopant. At this time, even if a fluorescent dopant which emits light with a relatively short wavelength such as blue light is used, light can be emitted efficiently from the dopant because the phenanthrene compound of this embodiment has a wide band gap. In other words, the phenanthrene compound of this embodiment can be used as a host material for a compound which emits fluorescence in the visible region. In the case where a dopant is a phosphorescent compound, a substance which has a higher T1 level than the dopant is preferably used as a host material. The phenanthrene compound of this embodiment has a high T1 level, and thus can be used as a host material for a compound which emits phosphorescence in the visible region with a wavelength longer than that of at least green light.

This embodiment can be implemented in appropriate combination with any of the other embodiments and examples.

Embodiment 2

In this embodiment, a light-emitting element including the phenanthrene compound described in Embodiment 1 as one embodiment of the present invention will be described with reference to FIGS. 1A and 1B.

In the light-emitting element of this embodiment, an EL layer including at least a light-emitting layer is interposed between a pair of electrodes. The EL layer may have a plurality of layers in addition to the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. The plurality of layers may include, for example, a hole-injection layer, a hole-transport layer, an electron-transport layer, an electron-injection layer, and the like.

In the light-emitting element of this embodiment illustrated in FIG. 1A, an EL layer 102 is provided between a pair of electrodes, a first electrode 101 and a second electrode 103. The EL layer 102 includes a hole-injection layer 111, a hole-transport layer 112, a light-emitting layer 113, an electron-transport layer 114, and an electron-injection layer 115. Note that in the light-emitting element described in this embodiment, the first electrode 101 provided over a substrate 100 functions as an anode and the second electrode 103 functions as a cathode.

A substrate 100 is used as a support of the light-emitting element. For example, glass, quartz, plastic, or the like can be used for the substrate 100. A flexible substrate may be used. A flexible substrate is a substrate that can be bent (is flexible); examples of the flexible substrate include a plastic substrate made of a polycarbonate, a polyarylate, or a polyethersulfone, and the like. A film made of polypropylene, a polyester, poly(vinyl fluoride), poly(vinyl chloride), or the like, an inorganic film formed by evaporation, or the like can be used. Note that materials other than these can be used as long as they can function as a support of the light-emitting element.

For the first electrode 101, a metal, an alloy, an electrically conductive compound, a mixture thereof, or the like which has a high work function (specifically, a work function of 4.0 eV or more) is preferably used. Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like are given. Although films of these conductive metal oxides are usually formed by sputtering, a sol-gel method or the like may be used. For example, indium zinc oxide (IZO) can be formed by a sputtering method using a target in which zinc oxide is added to indium oxide at 1 wt % to 20 wt %. Indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Other examples include gold, platinum, nickel, tungsten, chromium, molybdenum, iron, cobalt, copper, palladium, nitrides of metal materials (e.g., titanium nitride), and the like.

Note that, in the EL layer 102, when a layer in contact with the first electrode 101 is formed using a composite material in which an organic compound and an electron acceptor (acceptor) which are described later are mixed, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., Al—Si), graphene, or the like can be used.

In the EL layer 102 formed over the first electrode 101, at least the light-emitting layer 113 contains the phenanthrene compound of one embodiment of the present invention. The phenanthrene compound of one embodiment of the present invention is a material having a bipolar property, and thus can also be used as a material of a carrier-transport layer (e.g., the hole-transport layer or the electron-transport layer) in the EL layer 102. For part of the EL layer 102, a known substance can be used, and either a low molecular compound or a high molecular compound can be used. Note that the substance used for forming the EL layer 102 may have not only a structure formed of only an organic compound but also a structure partly including an inorganic compound.

The hole-injection layer 111 is a layer that contains a substance having a high hole-injection property. As the substance having a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

The following aromatic amine compounds which are low molecular organic compounds can be used: 4,4',4"-tris(N,N-diphenylamino)triphenylamine (abbreviation: TDATA), 4,4', 4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'- bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), or the like.

High molecular compounds (such as an oligomer, a dendrimer, or a polymer) can be used. As examples of the high molecular compound, the following are given: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: Poly-TPD). A high molecular compound to which an acid is added, such as poly(3,4-ethylenedioxythiophene)/poly(styrenesulfonic acid) (PEDOT/PSS), or polyaniline/poly(styrenesulfonic acid) (PAni/PSS), can also be used.

A composite material in which an organic compound and an electron acceptor (acceptor) are mixed may be used for the hole-injection layer 111. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound for the composite material, any of a variety of compounds such as aromatic amine compounds, carbazole derivatives, aromatic hydrocarbons, and high molecular compounds (e.g., oligomer, dendrimer, and polymer) can be used. The organic compound used for the composite material is preferably an organic compound having a high hole-transport property. Specifically, a substance having a hole mobility of $10^{-6}$ cm$^2$/Vs or higher is preferably used. Note that any other substances may also be used as long as the hole-transport property thereof is higher than the electron-transport property thereof. The organic compounds that can be used for the composite material will be specifically given below.

The phenanthrene compound of one embodiment of the present invention is an organic compound having a high hole-transport property, and thus can be favorably used for the composite material. Besides, examples of the organic compound that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD) 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As examples of the electron acceptor used for the composite material, organic compounds such as 7,7,8,8-tetracyano-2,3,5,6-tetrafluoroquinodimethane (abbreviation: F$_4$-TCNQ) and chloranil; and transition metal oxides can be given. Oxides of metals belonging to Groups 4 to 8 in the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is particularly preferable because it is stable in the air, has a low hygroscopic property, and is easily handled.

Note that the composite material may be formed using the above-described electron acceptor and the above high molecular compound such as PVK, PVTPA, PTPDMA, or Poly-TPD and may be used for the hole-injection layer 111.

The hole-transport layer 112 is a layer that contains a substance having a high hole-transport property. Examples of the substance having a high hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like. The substances given here are mainly ones that have a hole mobility of $10^{-6}$ cm$^2$/V·s or higher. Note that any other substances may also be used as long as the hole-transport property thereof is higher than the electron-transport property thereof. The phenanthrene compound described in Embodiment 1 can also be used. Note that the layer containing a substance having a high hole-transport property is not limited to a single layer and may be a stack of two or more layers containing any of the above substances.

A high molecular compound such as poly(N-vinylcarbazole) (PVK) or poly(4-vinyltriphenylamine) (PVTPA) can also be used for the hole-transport layer 112.

The light-emitting layer 113 is a layer that contains the phenanthrene compound of one embodiment of the present invention (host material) and a light-emitting substance (guest material) dispersed in the phenanthrene compound. For example, a fluorescent compound which emits fluorescence or a phosphorescent compound which emits phosphorescence can be used as the light-emitting substance. Note that it is preferable that a substance which has a lower lowest unoccupied molecular orbital level (LUMO level) and a higher highest occupied molecular orbital level (HOMO level) than the phenanthrene compound of one embodiment of the present invention be used as the light-emitting substance.

The phenanthrene compound of one embodiment of the present invention has a wide band gap (the S1 level is high), and thus can be used favorably as a host material in the light-emitting layer 113. In the case where a light-emitting substance is a phosphorescent compound, a substance which has a higher T1 level than the light-emitting substance is preferably used as a host material for the light-emitting substance. The phenanthrene compound of one embodiment of the present invention has a high T1 level, and thus can also be used favorably as a host material for a phosphorescent substance.

As the fluorescent compound that can be used for the light-emitting layer 113, a material for blue light emission, a material for green light emission, a material for yellow light emission, and a material for red light emission are given. As examples of the material for blue light emission, the following are given: N,N'-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. As examples of the material for green light emission, the following are given: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As examples of the material for yellow light emission, rubrene, 5,12-bis(1,1'-biphenyl-4-yl)-6,11-diphenyltetracene (abbreviation: BPT), and the like are given. As examples of the material for red light emission, N,N,N',N'-tetrakis(4-methylphenyl)tetracene-5,11-diamine (abbreviation: p-mPhTD), 7,14-diphenyl-N,N,N,N-tetrakis(4-methylphenyl)acenaphtho[1,2-a]fluoranthene-3,10-diamine (abbreviation: p-mPhAFD), and the like are given.

As the phosphorescent compound that can be used for the light-emitting layer 113, a material for green light emission, a material for yellow light emission, a material for orange light emission, and a material for red light emission are given. As examples of the material for green light emission, the following are given: tris(2-phenylpyridinato-N,C$^{2'}$)iridium(III) (abbreviation: Ir(ppy)$_3$), bis[2-phenylpyridinato-N,C$^{2'}$]iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), tris(benzo[h]quinolinato)iridium(III) (abbreviation: Ir(bzq)$_3$), and the like. As examples of the material for yellow light emission, the following are given: bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)) (acetylacetonato)bis[2,3-bis(4-fluorophenyl)-5-methylpyrazinato]iridium(III) (abbreviation: Ir(Fdppr-Me)$_2$(acac)), (acetylacetonato)bis{2-(4-methoxyphenyl)-3,5-dimethylpyrazinato}iridium(III) (abbreviation: Ir(dmmoppr)$_2$(acac)), and the like. As examples of the material for orange light emission, the following are given: tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: Ir(mppr-iPr)$_2$(acac)), and the like. As examples of the material for red light emission, organometallic complexes such as bis[2-(2'-benzo[4,5-α]thienyl)pyridinato-N,C$^{3'}$)iridium(III) acetylacetonate (abbreviation: [Ir(btp)$_2$(acac)]), bis(1-phenylisoquinolinato-N,C$^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), (dipivaloylmethanato)bis(2,3,5-triphenylpyrazinato)iridium(III) (abbreviation: [Ir(tppr)$_2$(dpm)]), and (2,3,7,8,12,13,17,18-octaethyl-21H,23H-porphyrin)platinum(II) (abbreviation: PtOEP). In addition, rare-earth metal complexes, such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)), exhibit light emission from rare-earth metal ions (electron transition between different multiplicities), and thus can be used as phosphorescent compounds.

A high molecular compound can be used as the light-emitting substance. Specifically, a material for blue light emission, a material for green light emission, and a material for orange to red light emission are given. As examples of the material for blue light emission, the following are given: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. As examples of the material for green light emission, the following are given: poly(p-phenylenvinylene) (abbreviation: PPV), poly[(9,9-dihexylfluorene-2,7-diyl)-alt-co-(benzo[2,1,3]thiadiazol-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], and the like. As examples of the material for orange to red light emission, the following are given: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenylamino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

Plural kinds of materials can be used as the host material in the light-emitting layer 113. For example, in order to suppress crystallization, a substance such as rubrene which suppresses crystallization may be further added to the phenanthrene compound of one embodiment of the present invention. In addition, NPB, Alq, or the like may be further added in order to efficiently transfer energy to the guest material.

With a structure in which a guest material is dispersed in a host material, crystallization of the light-emitting layer 113 can be suppressed. In addition, concentration quenching due to an increase in the concentration of the guest material can be prevented.

Note that the light-emitting layer 113 may have a structure in which two or more layers are stacked. In that case, at least one of the layers may contain the phenanthrene compound of one embodiment of the present invention. Note that in the case where the light-emitting layer 113 has a structure in which two or more layers are stacked, the stacked layers may emit light of the same color or different colors. Further, a layer containing a fluorescent compound as a light-emitting substance and a layer containing a phosphorescent compound as a light-emitting substance can be stacked.

The electron-transport layer 114 is a layer that contains a substance having a high electron-transport property. Examples of the substance having a high electron-transport property include a metal complex having a quinoline skeleton or a benzoquinoline skeleton, such as tris(8-quinolinolato) aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq). A metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can also be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones that have an electron mobility of $10^{-6}$ cm$^2$/V·s or higher. The phenanthrene compound described in Embodiment 1 can also be used. Note that the electron-transport layer is not limited to a single layer and may be a stack of two or more layers containing any of the above substances.

The electron-injection layer 115 is a layer that contains a substance having a high electron-injection property. For the electron-injection layer 115, an alkali metal, an alkaline earth metal, or a compound thereof, such as lithium, cesium, calcium, lithium fluoride, cesium fluoride, calcium fluoride, or lithium oxide, can be used. A rare earth metal compound such as erbium fluoride can also be used. The substances given above for forming the electron-transport layer 114 can also be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the above-described materials for forming the electron-transport layer 114 (e.g., a metal complex or a heteroaromatic compound) can be used, for example. As the electron donor, a substance exhibiting an electron-donating property to the organic compound may be used. Specifically, it is preferable to use an alkali metal, an alkaline-earth metal, or a rare earth metal, such as lithium, cesium, magnesium, calcium, erbium, or ytterbium. In addition, it is preferable to use an alkali metal oxide or an alkaline-earth metal oxide, such as lithium oxide, calcium oxide, or barium oxide. Lewis base such as magnesium oxide can also be used. An organic compound such as tetrathiafulvalene (abbreviation: TTF) can also be used.

Note that the hole-injection layer 111, the hole-transport layer 112, the light-emitting layer 113, the electron-transport layer 114, and the electron-injection layer 115 which are described above can each be formed by a method such as an evaporation method (e.g., a vacuum evaporation method), an ink-jet method, or a coating method.

When the second electrode 103 functions as a cathode, it can be formed using a metal, an alloy, an electrically-conductive compound, a mixture thereof, or the like having a low work function (preferably, a work function of 3.8 eV or less). Specifically, any of the following can be used: aluminum or silver; an element belonging to Group 1 or Group 2 of the periodic table, that is, an alkali metal such as lithium or cesium or an alkaline earth metal such as magnesium, calcium, or strontium; an alloy of the above metals (e.g., Mg—Ag or Al—Li); a rare earth metal such as europium or ytterbium; an alloy of the above metals; or the like.

Note that, in the case where in the EL layer 102, a layer formed in contact with the second electrode 103 is formed using a composite material in which the organic compound and the electron donor, which are described above, are mixed, a variety of conductive materials such as aluminum, silver, ITO, indium tin oxide containing silicon or silicon oxide, and graphene can be used regardless of the work function.

Note that the second electrode 103 can be formed by a vacuum evaporation method or a sputtering method. In the case of using a silver paste or the like, a coating method, an inkjet method, or the like can be used.

In the above light-emitting element, current flows due to a potential difference applied between the first electrode 101 and the second electrode 103 and holes and electrons recombine in the EL layer 102, whereby light is emitted. Then, this emitted light is extracted through one or both of the first electrode 101 and the second electrode 103. Therefore, one or both of the first electrode 101 and the second electrode 103 is/are an electrode having a property of transmitting visible light.

Note that the structure of the layer provided between the first electrode 101 and the second electrode 103 is not limited to the above structure. A structure other than the above may also be employed as long as a light-emitting region in which holes and electrons recombine is provided in a portion away from the first electrode 101 and the second electrode 103 in order to prevent quenching due to proximity of the light-emitting region to a metal.

In other words, a stacked structure of the layer is not particularly limited, and a layer formed of a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer.

Figure 1B:
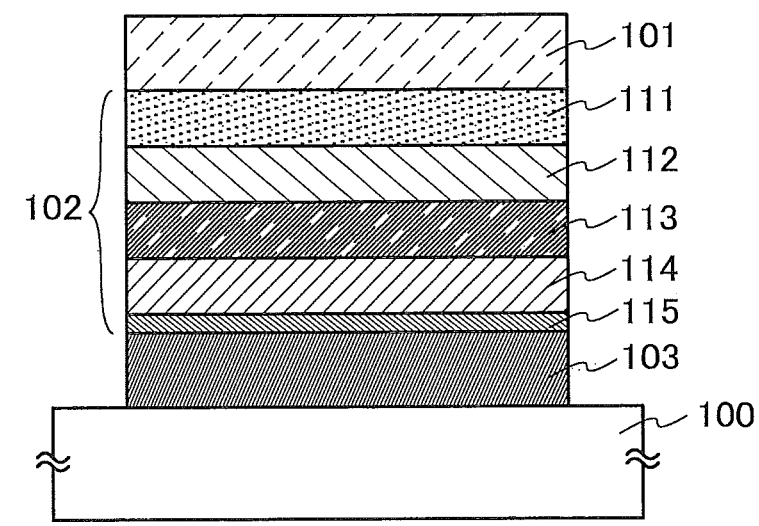

In a light-emitting element illustrated in FIG. 1B, the EL layer 102 is provided between the first electrode 101 and the second electrode 103 over the substrate 100. The EL layer 102 includes a hole-injection layer 111, a hole-transport layer 112, the light-emitting layer 113, an electron-transport layer 114, and an electron-injection layer 115. The light-emitting element in FIG. 1B includes: the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

A specific manufacturing method of a light-emitting element will be described below.

The light-emitting element of this embodiment has a structure in which an EL layer is interposed between a pair of electrodes. The electrode (the first electrode or the second electrode) and the EL layer may be formed by a wet process such as a droplet discharging method (an ink-jet method), a spin coating method, or a printing method, or by a dry process such as a vacuum evaporation method, a CVD method, or a sputtering method. The use of a wet process enables formation at atmospheric pressure with a simple device and by a simple process, which gives effects of simplifying the process and improving productivity. In contrast, a dry process does not need dissolution of a material and enables use of a material that has low solubility in a solution, which expands the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas functional layers such as the electron-transport layer, the first electrode, and the like which are stacked over the light-emitting layer may be formed by a dry process. Further alternatively, the second electrode and the functional layers may be formed by a dry process before the formation of the light-emitting layer whereas the light-emitting layer, the functional layers stacked thereover, and the first electrode may be formed by a wet process. Needless to say, this embodiment is not limited to this, and the light-emitting element can be formed by appropriate selection from a wet method and a dry method depending on a material to be used, film thickness that is necessary, and the interface state.

In the above manner, the light-emitting element can be manufactured using the phenanthrene compound of one embodiment of the present invention.

Note that by use of a light-emitting element described in this embodiment, a passive matrix light-emitting device or an active matrix light-emitting device in which driving of the light-emitting element is controlled by a transistor can be manufactured.

This embodiment can be implemented in appropriate combination with any of the other embodiments.

Embodiment 3

In this embodiment, a mode of a light-emitting element having a structure in which a plurality of light-emitting units are stacked (such a light-emitting element is hereinafter referred to as a stacked-type element) will be described with reference to FIGS. 2A and 2B. This light-emitting element is a light-emitting element including a plurality of light-emitting units between a first electrode and a second electrode.

Figure 2A:
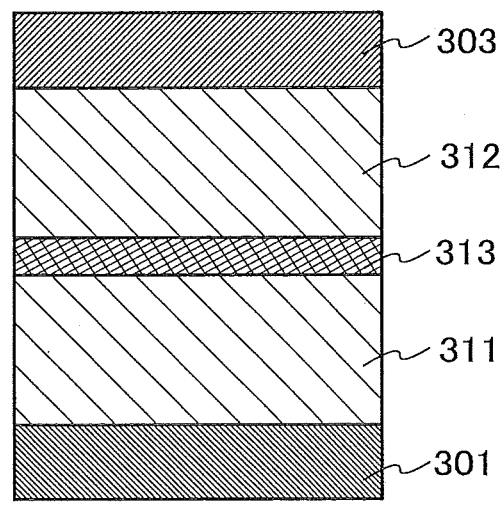
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. Note that as the materials for the first electrode 301 and the second electrode 303, those described in Embodiment 2 can be used. The first light-emitting unit 311 and the second light-emitting unit 312 may have the same or different structures. The first light-emitting unit 311 and the second light-emitting unit 312 may have the structure same as that of the light-emitting layer 113 in Embodiment 2, or either of the units may have a structure different from that of the light-emitting layer 113 in Embodiment 2.

Further, a charge generation layer 313 is provided between the first light-emitting unit 311 and the second light-emitting unit 312. The charge generation layer 313 has a function of injecting electrons into one light-emitting unit and injecting holes into the other light-emitting unit when voltage is applied between the first electrode 301 and the second electrode 303. In this embodiment, when voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has a property of transmitting visible light in terms of light extraction efficiency. Further, the charge generation layer 313 functions even when it has lower conductivity than the first electrode 301 or the second electrode 303.

The charge generation layer 313 may have either a structure including an organic compound having a high hole-transport property and an electron acceptor or a structure including an organic compound having a high electron-transport property and an electron donor. Alternatively, both of these structures may be stacked. Note that the electron acceptor and the electron donor are at least capable of donating and accepting electrons with the assistance of an electric field.

In the case of a structure in which an electron acceptor is added to an organic compound having a high hole-transport property, as the organic compound having a high hole-transport property, the phenanthrene compound of one embodiment of the present invention can be used. Other examples of the organic compound having a high hole-transport property include aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like.

As examples of the electron acceptor, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is particularly preferable because it is stable in the air, has a low hygroscopic property, and is easily handled.

In contrast, in the case of a structure in which an electron donor is added to an organic compound having a high electron-transport property, as the organic compound having a high electron-transport property, a metal complex having a quinoline skeleton or a benzoquinoline skeleton, such as Alq, Almq$_3$, BeBq$_2$, or BAlq, or the like can be used, for example. A metal complex having an oxazole-based ligand or a thiazole-based ligand, such as Zn(BOX)$_2$ or Zn(BTZ)$_2$ can also be used. Other than the metal complexes, PBD, OXD-7, TAZ, BPhen, BCP, or the like can be used. The phenanthrene compound of one embodiment of the present invention may also be used.

As the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that the charge generation layer 313 is formed using any of the above materials, whereby an unnecessary increase in driving voltage caused when the EL layers are stacked can be suppressed.

Figure 2B:
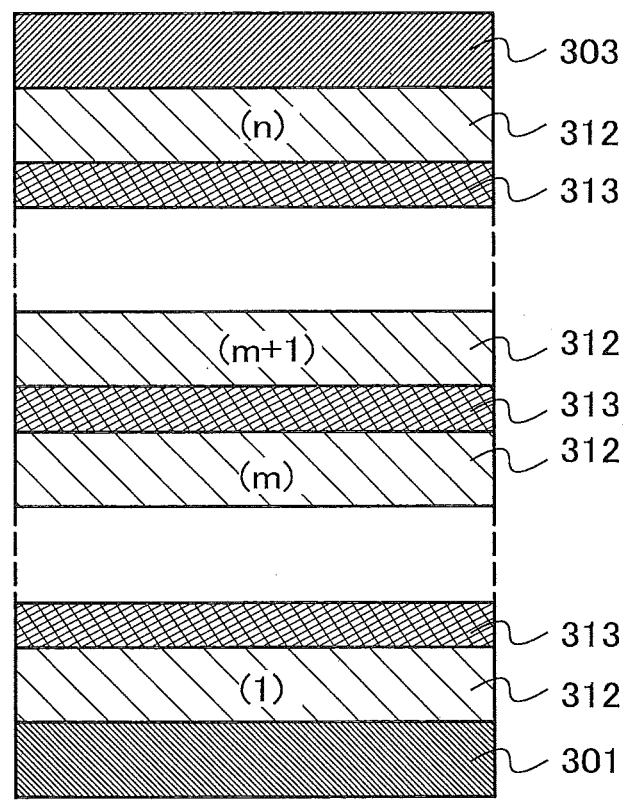

In this embodiment, the light-emitting element having two light-emitting units is described, and one embodiment of the present invention can be similarly applied to a light-emitting element having a stack of three or more light-emitting units as illustrated in FIG. 2B. For example, in a stacked structure of n layers (n is a natural number greater than or equal to 2), the charge generation layer 313 is interposed between an m-th light-emitting unit and an (m+1)-th light-emitting unit (m is a natural number less than or equal to (n−1)). A plurality of light-emitting units which are partitioned by a charge generation layer are arranged between a pair of electrodes as in the light-emitting element according to this embodiment, whereby it is possible to obtain an element having long lifetime which can emit light with a high luminance while current density is kept low.

Further, the light-emitting units emit light having different colors from each other, thereby obtaining light emission of a desired color in the whole light-emitting element. For example, in the light-emitting element having two light-emitting units, when an emission color of the first light-emitting unit and an emission color of the second light-emitting unit are made to be complementary colors, it is possible to obtain a light-emitting element which emits white light as a whole light-emitting element. Note that "complementary colors" refer to colors that can produce an achromatic color when mixed. Examples of the pair of the complementary colors include blue and yellow, blue-green and red, and the like. In the case of a light-emitting element having three light-emitting units in which, for example, a first light-emitting unit emits red light, a second light-emitting unit emits green light, and a third light-emitting unit emits blue light, the whole light-emitting element can emit white light.

Note that this embodiment can be freely combined with any of the other embodiments and examples.

Embodiment 4

In this embodiment, a light-emitting device that is one embodiment of the present invention will be described with reference to FIGS. 3A and 3B. FIG. 3A is a top view illustrating a light-emitting device. FIG. 3B is a cross-sectional view taken along lines A-B and C-D in FIG. 3A.

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure will be described with reference to FIG. 3B. The driver circuit portion and the pixel portion are formed over an element substrate 410. Here, the source driver circuit 401 which is the driver circuit portion and one pixel in the pixel portion 402 are illustrated.

Note that as the source side driver circuit 401, a CMOS circuit, which is a combination of an n-channel TFT 423 and a p-channel TFT 424, is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive acrylic resin film.

In order to improve the coverage, the insulator 414 is provided such that either an upper end portion or a lower end portion of the insulator 414 has a curved surface with a curvature. For example, when positive type photosensitive acrylic resin is used as a material for the insulator 414, the insulator 414 preferably has a curved surface with a curvature radius (0.2 µm to 3 µm) only as the upper end. The insulator 414 can be formed using either a negative type resin which becomes insoluble in an etchant by light irradiation or a positive type resin which becomes soluble in an etchant by light irradiation.

An EL layer 416 and a second electrode 417 are formed over the first electrode 413. Each of the first electrode 413, the EL layer 416, and the second electrode 417 can be formed using any of the materials described in Embodiment 2. Note that the EL layer 416 includes at least a light-emitting layer that contains the phenanthrene compound described in Embodiment 1. The first electrode 413 functions as an anode and the second electrode 417 functions as a cathode in this embodiment.

The sealing substrate 404 is attached to the element substrate 410 with the sealant 405, whereby a light-emitting element 418 is provided in the space 407 enclosed by the element substrate 410, the sealing substrate 404, and the sealant 405. Note that the space 407 may be filled with filler such as an inert gas (e.g., nitrogen or argon) or with the sealant 405.

Note that an epoxy-based resin is preferably used as the sealant 405. As a material for the sealing substrate 404, a glass substrate, a quartz substrate, or a plastic substrate including fiberglass-reinforced plastics (FRP), poly(vinyl fluoride) (PVF), a polyester, an acrylic resin, or the like can be used. It is desirable that materials for the sealing substrate 404, the sealant 405, and the element substrate 410 transmit as little moisture or oxygen as possible.

In the above manner, the active matrix light-emitting device including the light-emitting element of one embodiment of the present invention can be obtained.

Figure 4A:
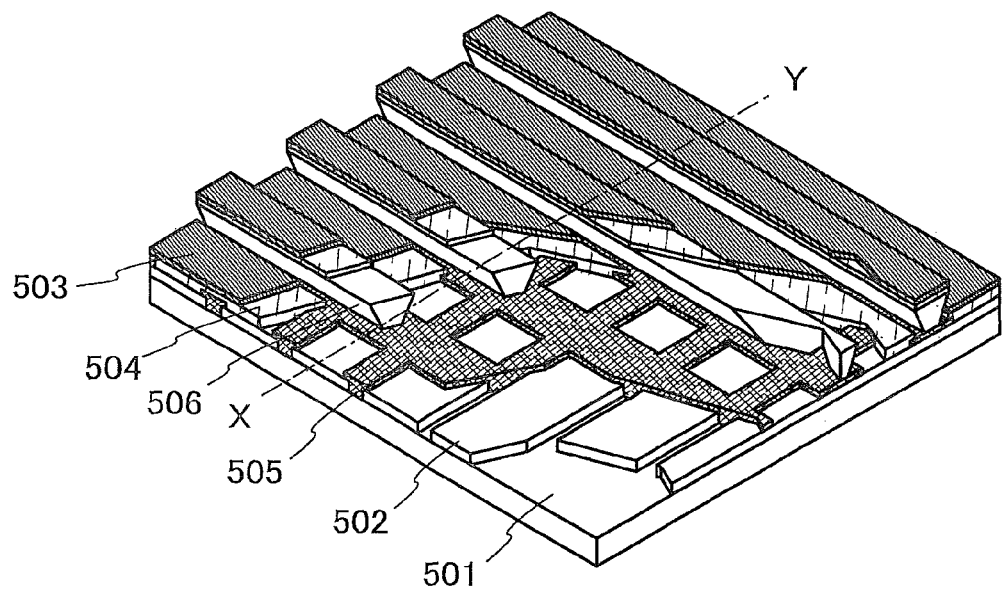
FIGS. 4A and 4B illustrate a light-emitting device of one embodiment of the present invention.
Figure 4B:
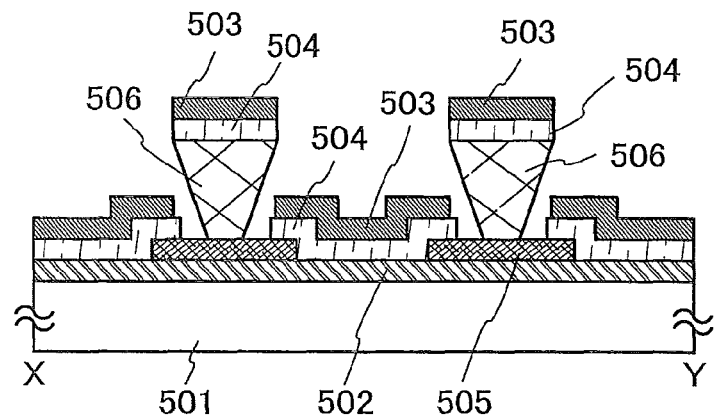

Further, the light-emitting element of the present invention can be used for a passive matrix light-emitting device instead of the above active matrix light-emitting device. FIGS. 4A and 4B illustrate a perspective view and a cross-sectional view of a passive matrix light-emitting device including the light-emitting element of one embodiment of the present invention. FIG. 4A is a perspective view of the light-emitting device. FIG. 4B is a cross-sectional view taken along line X-Y in FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the base (side facing in a direction parallel to the plane direction of the insulating layer 505 and being in contact with the insulating layer 505) is shorter than the upper side (side facing in the direction parallel to the plane direction of the insulating layer 505 and not being in contact with the insulating layer 505. The partition layer 506 is provided in such a manner, whereby a defect of a light-emitting element due to static electricity or the like can be prevented.

In the above manner, the passive matrix light-emitting device including the light-emitting element of one embodiment of the present invention can be obtained.

The light-emitting devices described in this embodiment (the active matrix light-emitting device and the passive matrix light-emitting device) are both formed using the light-emitting element of one embodiment of the present invention.

Note that this embodiment can be freely combined with any of the other embodiments and examples.

Embodiment 5

In this embodiment, examples of a variety of electronic devices and lighting devices which are completed by using a light-emitting device that is one embodiment of the present invention will be described with reference to FIGS. 5A to 5E, FIG. 6, and FIG. 7.

Examples of the electronic device to which the light-emitting device is applied include television devices (also referred to as TV or television receivers), monitors for computers and the like, cameras such as digital cameras and digital video cameras, digital photo frames, cellular phones (also referred to as portable telephone devices), portable game machines, portable information terminals, audio reproducing devices, large game machines such as pin-ball machines, and the like. FIGS. 5A to 5E illustrate specific examples of these electronic devices and a lighting device.

Figure 5A:
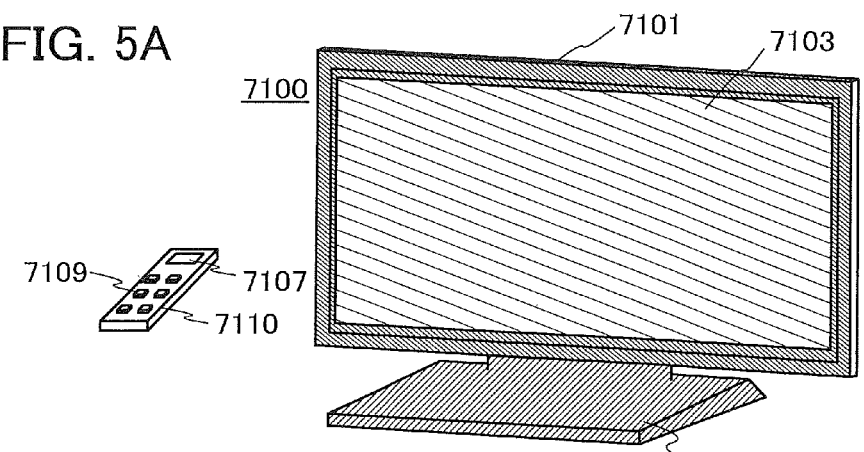
FIGS. 5A to 5E illustrate electronic devices and a lighting device of one embodiment of the present invention.

FIG. 5A illustrates an example of a television device. In the television device 7100, a display portion 7103 is incorporated in a housing 7101. The display portion 7103 is capable of displaying images, and the light-emitting device of one embodiment of the present invention can be used for the display portion 7103. Here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a sender to a receiver) or two-way (between a sender and a receiver, between receivers, or the like) data communication can be performed.

Figure 5B:
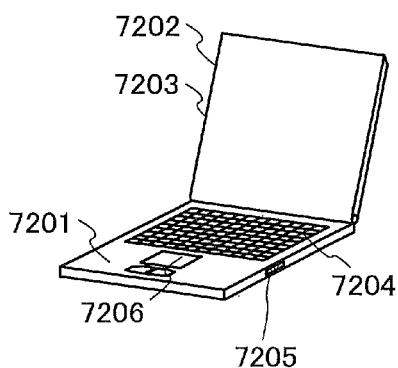

FIG. 5B illustrates a computer, which includes a main body 7201, a housing 7202, a display portion 7203, a keyboard 7204, an external connecting port 7205, a pointing device 7206, and the like. Note that this computer is manufactured by using the light-emitting device of one embodiment of the present invention for the display portion 7203.

Figure 5C:
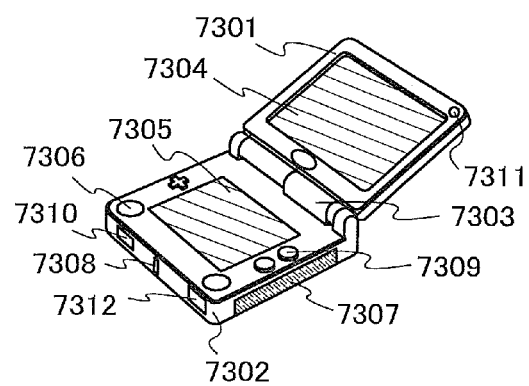

FIG. 5C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, smell, or infrared rays), or a microphone 7312), and the like. Needless to say, the structure of the portable game machine is not limited to the above as long as the light-emitting device of one embodiment of the present invention is used for at least either the display portion 7304 or the display portion 7305, or both, and can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
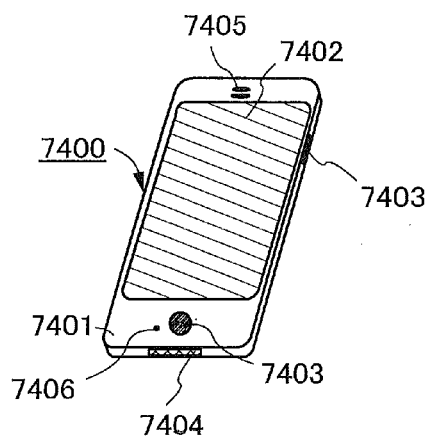

FIG. 5D illustrates an example of a mobile phone. The mobile phone 7400 is provided with a display portion 7402 incorporated in a housing 7401, operation buttons 7403, an external connection port 7404, a speaker 7405, a microphone 7406, and the like. Note that the mobile phone 7400 is manufactured by using the light-emitting device of one embodiment of the present invention for the display portion 7402.

When the display portion 7402 of the mobile phone 7400 illustrated in FIG. 5D is touched with a finger or the like, data can be input into the mobile phone 7400. Further, operations such as making a call and composing an e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touch on the display portion 7402 or operation with the operation buttons 7403 of the housing 7401. Alternatively, the screen modes can be switched depending on the kind of image displayed on the display portion 7402. For example, when a signal of an image displayed on the display portion is a signal of moving image data, the screen mode is switched to the display mode; when the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be switched from the input mode to the display mode.

The display portion 7402 can also function as an image sensor. For example, an image of a palm print, a fingerprint, or the like is taken by touch on the display portion 7402 with the palm or the finger, whereby personal authentication can be performed. Moreover, when a backlight or a sensing light source which emits near-infrared light is provided in the display portion, an image of finger veins, palm veins, or the like can be taken.

Figure 5E:
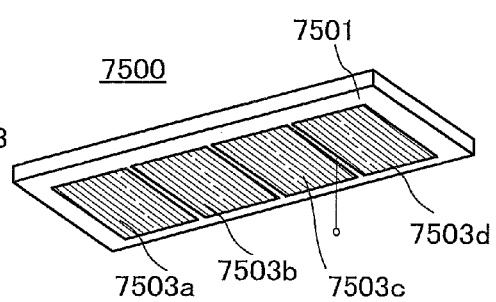

FIG. 5E illustrates an example of a lighting device. In a lighting device 7500, light-emitting devices 7503a to 7503d of one embodiment of the present invention are incorporated in a housing 7501 as light sources. The lighting device 7500 can be attached to a ceiling, a wall, or the like.

The light-emitting device of one embodiment of the present invention includes a light-emitting element in a thin film form. Thus, when the light-emitting device is attached to a base with a curved surface, the light-emitting device with a curved surface can be obtained. In addition, when the light-emitting device is located in a housing with a curved surface, an electronic device or a lighting device with a curved surface can be obtained.

Figure 6:
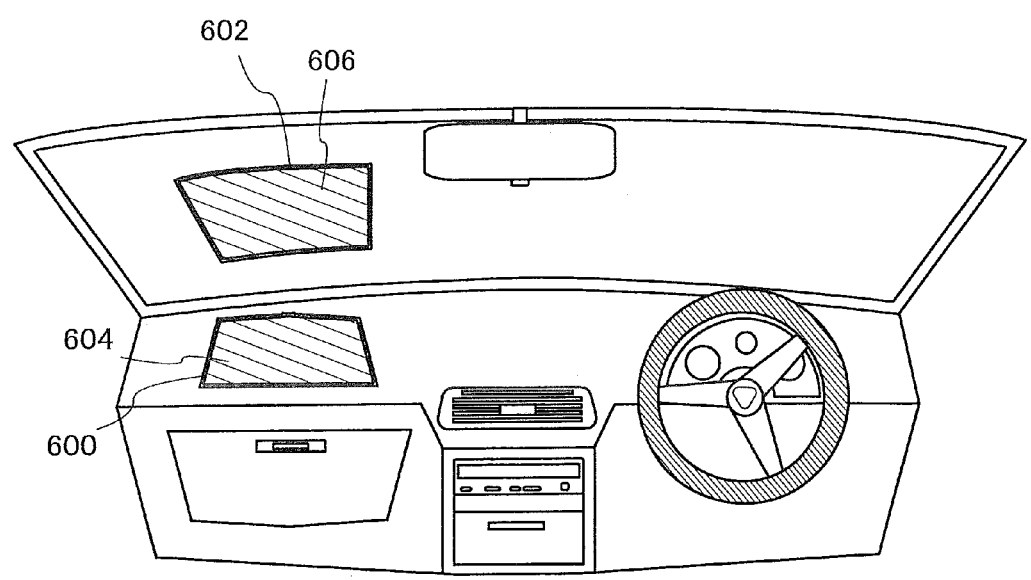
FIG. 6 illustrates an electronic device of one embodiment of the present invention.

FIG. 6 illustrates a driver's seat and the periphery thereof inside a vehicle. FIG. 6 illustrates an example in which a display device 600 is set on a dashboard and a display device 602 is set on a windshield. In the display device 600 illustrated in FIG. 6, a display portion 604 is incorporated in a housing with a curved surface and can display images. In the display device 600, the light-emitting device of one embodiment of the present invention can be used in the display portion 604.

In the display device 602 illustrated in FIG. 6, a display portion 606 is incorporated in a housing with a curved surface and the light-emitting device of one embodiment of the present invention can be used in the display portion 606. A pair of electrodes and a support of a light-emitting element which are included in the light-emitting device of one embodiment of the present invention are formed using a light-transmitting material, whereby light can be extracted through both a top surface and a bottom surface of the light-emitting device. Thus, the light-emitting device is used in the display portion 606, whereby a user can see the outside from the display portion 606 through the windshield. Similarly, a user can also see an image displayed on the display portion 606 from the outside through the windshield.

Note that the display device 600 or the display device 602 illustrated in FIG. 6 can also be used as a lighting device.

Figure 7:
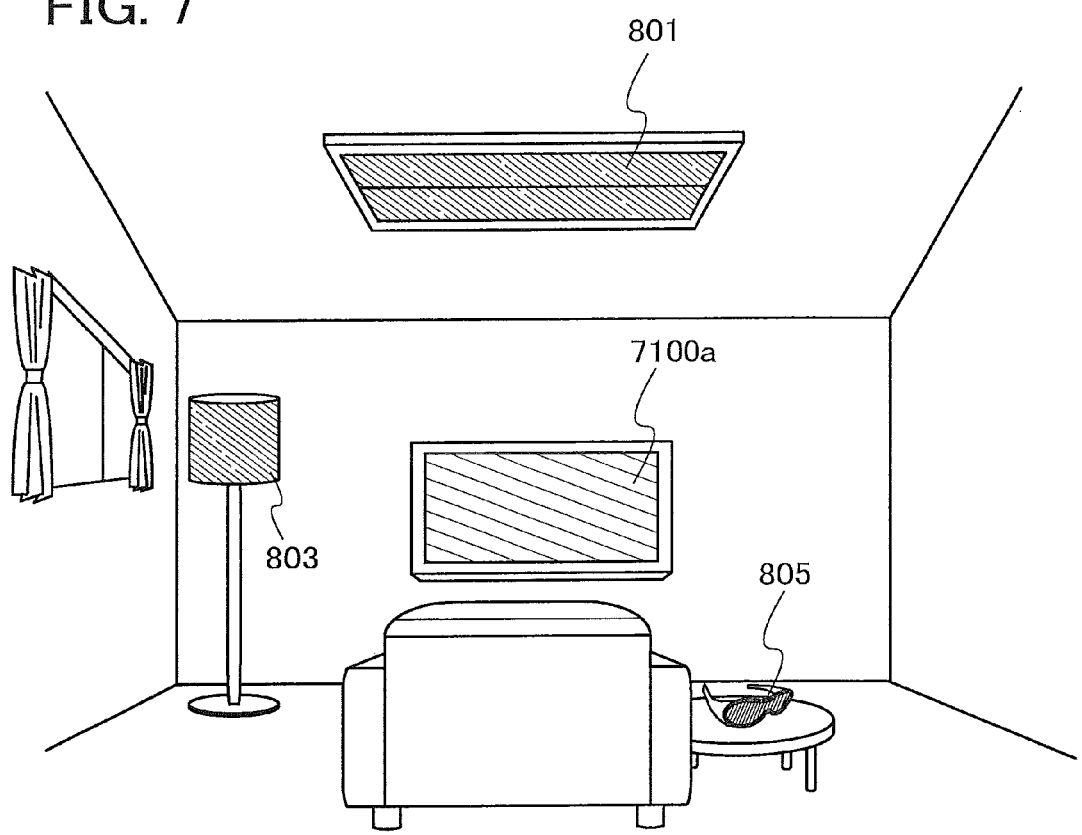
FIG. 7 illustrates an electronic device and lighting devices of one embodiment of the present invention.

FIG. 7 illustrates an example in which the light-emitting device is used as an indoor lighting device 801. Since the area of the light-emitting device can be increased, the light-emitting device can be used as a lighting device with a large area. In addition, a lighting device 803 in which a light-emitting region has a curved surface can also be obtained with the use of a housing with a curved surface. A light-emitting element included in the lighting device described in this embodiment is in a thin film form, which allows the housing to be designed more freely. Therefore, the lighting device can be elaborately designed in a variety of ways.

A television device 7100a that is a television device one example of which is illustrated in FIG. 5A can be set in a room provided with the lighting device to which one embodiment of the present invention is applied. The television device 7100a may have a three-dimensional display function as well as a normal two-dimensional display function. In FIG. 7, a three-dimensional image can be watched with glasses 805 for watching three-dimensional images.

As described above, the electronic devices and the lighting devices can be obtained by application of the light-emitting device. The light-emitting device has a remarkably wide application range, and thus can be applied to electronic devices and lighting devices in a variety of fields.

Note that the structure described in this embodiment can be combined with any of the structures described in Embodiments 1 to 4 as appropriate.

EXAMPLE 1

In this example, an example of synthesizing 4-[4-(9-phenanthryl)phenyl]dibenzothiophene (abbreviation: DBT-PPn-II) represented by Structural Formula (100) in Embodiment 1 will be described.

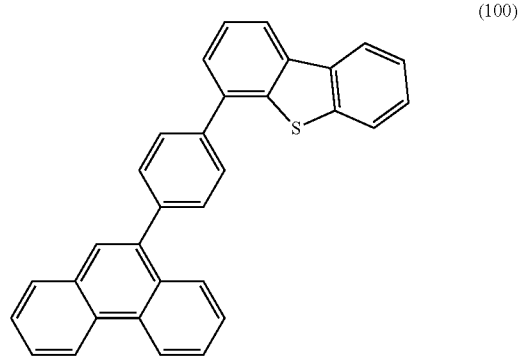 [SMILES: c1ccc2c(c1)cc(-c1ccc(-c3cccc4c3sc3ccccc34)cc1)c1ccccc12]

(100)

In a 50-mL three-neck flask were put 1.2 g (3.6 mmol) of 9-(4-bromophenyl)phenanthrene, 0.8 g (3.5 mmol) of dibenzothiophene-4-boronic acid, and 53 mg (0.2 mmol) of tris(2-methylphenyl)phosphine. The air in the flask was replaced with nitrogen. To this mixture were added 3.5 mL of a 2.0 M aqueous potassium carbonate solution, 13 mL of toluene, and 4.0 mL of ethanol. The mixture was degassed by being stirred under reduced pressure. Then, 8.0 mg (36 µmol) of palladium (II) acetate was added to this mixture, and the mixture was stirred at 80° C. for 7 hours under a nitrogen stream. After a certain period of time, the aqueous layer of the obtained mixture was extracted with toluene.

The obtained extract solution combined with the organic layer was washed with saturated saline, followed by drying with magnesium sulfate. This mixture was separated by gravity filtration, and the filtrate was concentrated to give an oily substance. This oily substance was purified by silica gel column chromatography. The silica gel column chromatography was conducted using a developing solvent of hexane and toluene (hexane:toluene=20:1). The obtained fractions were concentrated to give an oily substance. To this oily substance was added a mixed solvent of toluene and hexane to allow precipitation of a crystal, giving 0.8 g of white powder that was the substance to be produced, in a yield of 53%.

By a train sublimation method, 0.8 g of the obtained white powder was purified. In the purification, the white powder was heated at 240° C. under a pressure of 2.4 Pa with a flow rate of argon gas of 5 mL/min. After the purification, 0.7 g of white powder was obtained in a yield of 88%. The synthesis scheme of the above is shown in (E1) below.

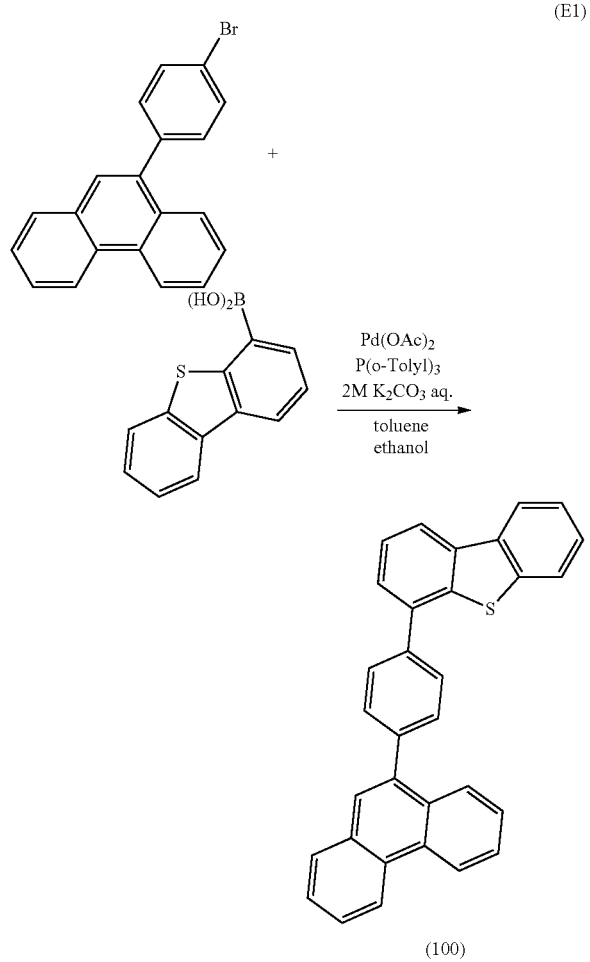

A nuclear magnetic resonance (NMR) method identified this compound as 4-[4-(9-phenanthryl)phenyl]dibenzothiophene (abbreviation: DBTPPn-II) that was the substance to be produced.

$^1$H NMR data of the obtained compound is as follows: $^1$H NMR (CDCl$_3$, 300 MHz): δ (ppm)=7.46-7.53 (m, 2H), 7.58-7.73 (m, 8H), 7.80 (s, 1H), 7.87-7.96 (m, 4H), 8.07 (d, J=8.1 Hz, 1H), 8.18-8.24 (m, 2H), 8.76 (d, J=8.1 Hz, 1H), 8.82 (d, J=7.8 Hz, 1H).

Figure 8A:
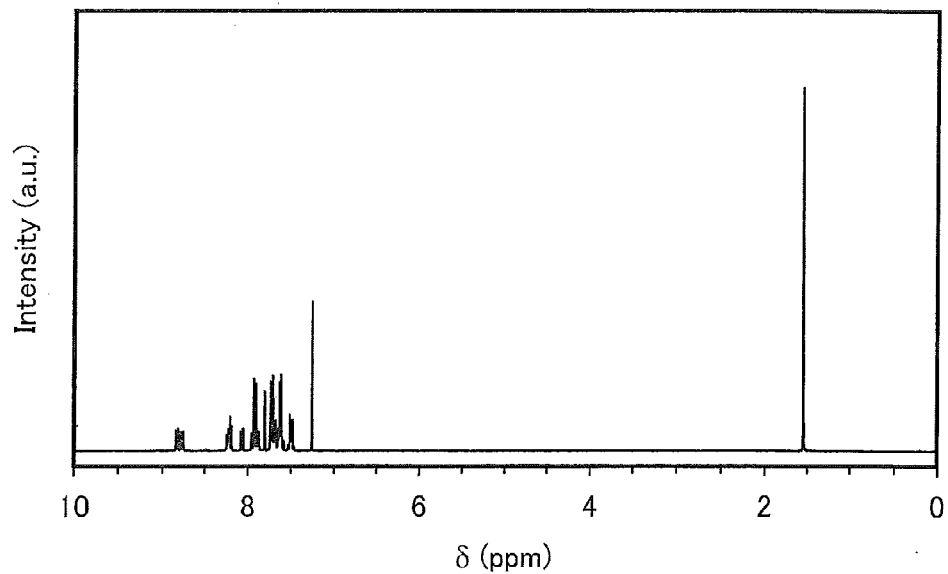
FIGS. 8A and 8B are NMR charts of DBTPPn-II.
Figure 8B:
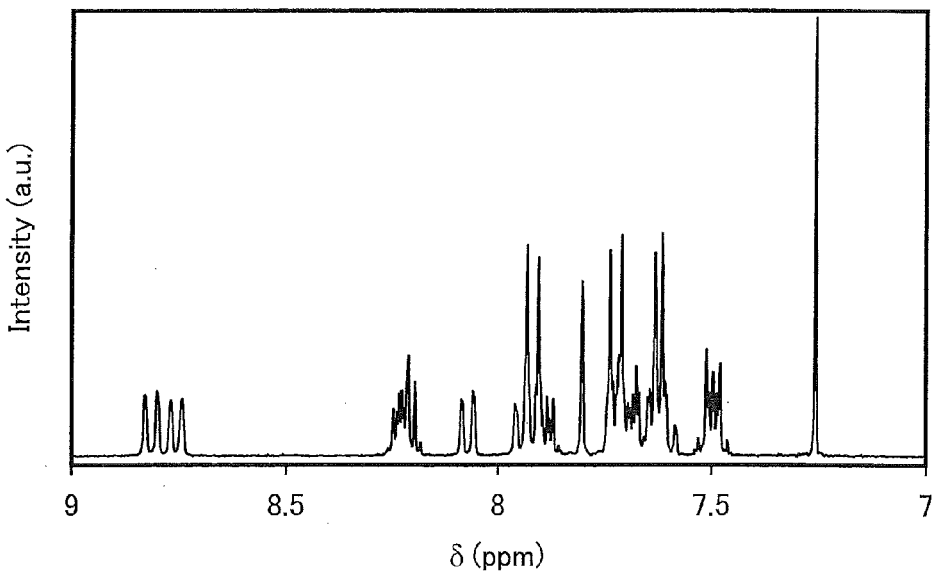

FIGS. 8A and 8B are $^1$H NMR charts. Note that FIG. 8B is a chart showing an enlarged part of FIG. 8A in the range of 7.0 ppm to 9.0 ppm.

Figure 9A:
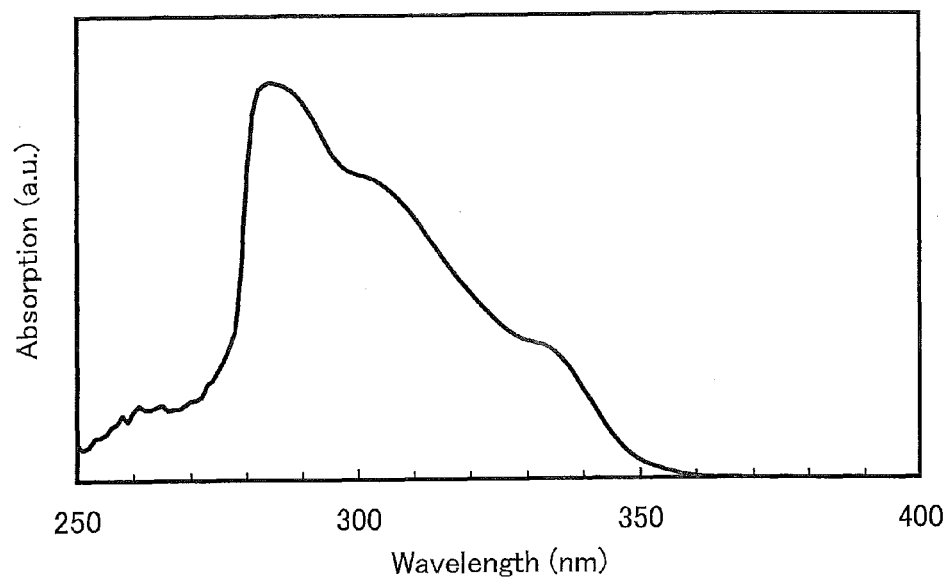
FIGS. 9A and 9B show an absorption spectrum and an emission spectrum of a toluene solution of DBTPPn-II.
Figure 9B:
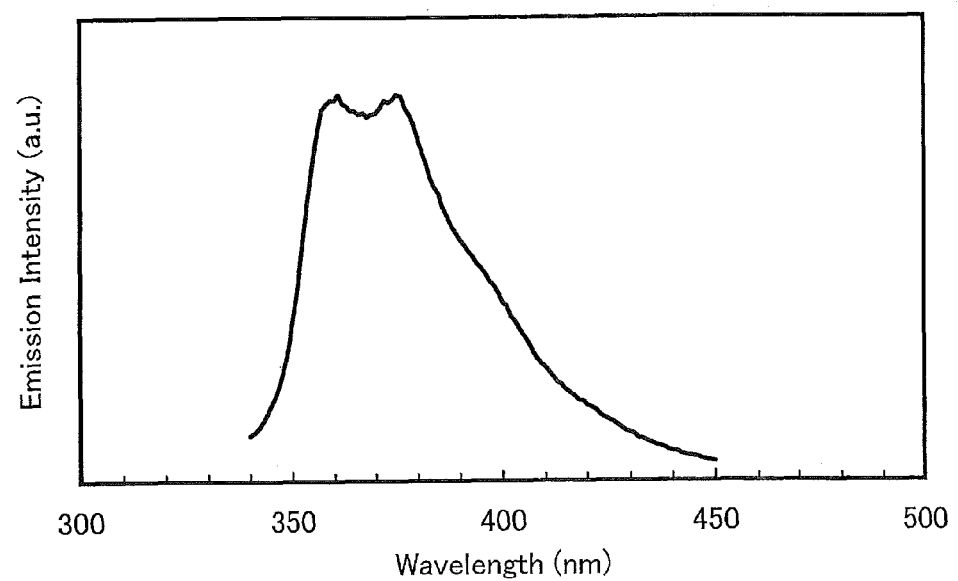
Figure 10A:
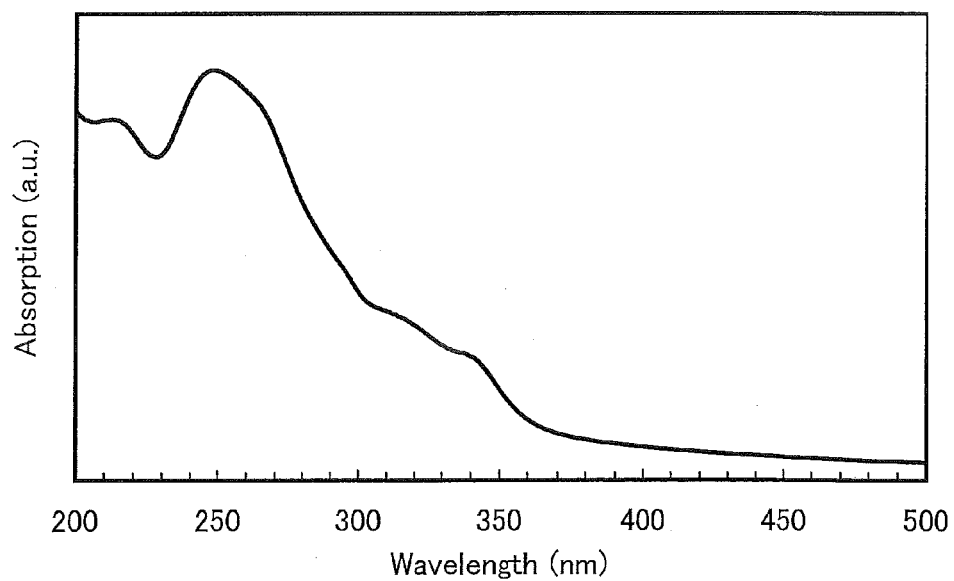
FIGS. 10A and 10B show an absorption spectrum and an emission spectrum of a thin film of DBTPPn-II.
Figure 10B:
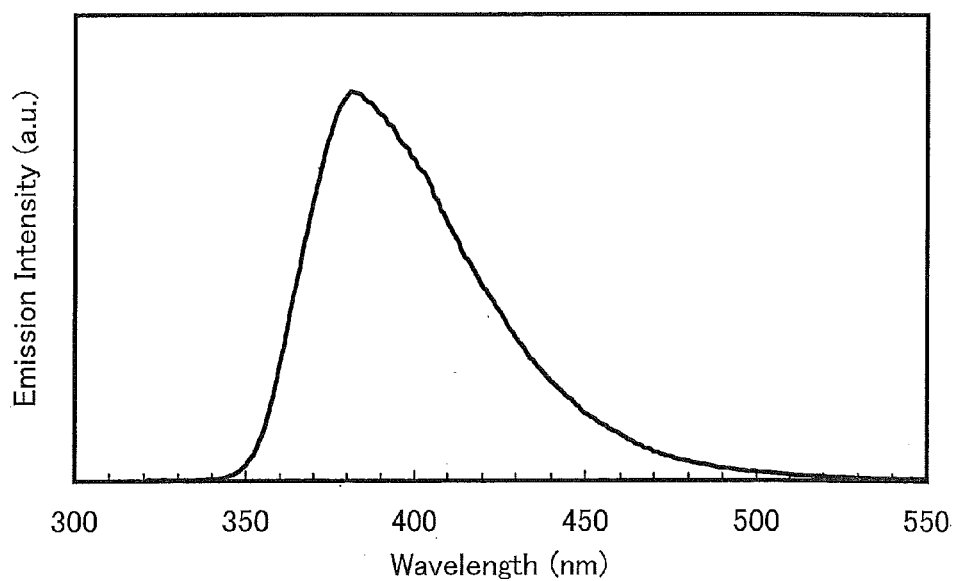

FIG. 9A shows an absorption spectrum of a toluene solution of DBTPPn-II, and FIG. 9B shows an emission spectrum thereof. FIG. 10A shows an absorption spectrum of a thin film of DBTPPn-II, and FIG. 10B shows an emission spectrum thereof. The absorption spectrum was measured with an ultraviolet-visible spectrophotometer (V550, produced by JASCO Corporation). The measurements were performed with samples prepared in such a manner that the solution was put in a quartz cell while the thin film was obtained by evaporation onto a quartz substrate. The absorption spectrum of the toluene solution of DBTPPn-II was obtained by subtracting the absorption spectra of the quartz cell and toluene from a raw data, and the absorption spectrum of the thin film of DBTPPn-II was obtained by subtracting the absorption spectrum of the quartz substrate from a raw data. In each of FIG. 9A and FIG. 10A, the horizontal axis represents wavelength (nm) and the vertical axis represents absorption intensity (arbitrary unit). In each of FIG. 9B and FIG. 10B, the horizontal axis represents wavelength (nm) and the vertical axis represents emission intensity (arbitrary unit). In the case of the toluene solution, an absorption peak was observed at 284 nm, shoulders were observed at 303 nm and 331 nm, and emission wavelength peaks were observed at 361 nm and 375 nm (excitation wavelength: 306 nm). In the case of the thin film, an absorption peak and a shoulder were observed at 248 nm and 338 nm, respectively, and an emission wavelength peak was observed at 382 nm (excitation wavelength: 305 nm).

The HOMO level and the LUMO level of the thin film of DBTPPn-II were measured. The value of the HOMO level was obtained by conversion of a value of the ionization potential measured with a photoelectron spectrometer (AC-2, manufactured by Riken Keiki Co., Ltd.) in the air into a negative value. The value of the LUMO level was obtained in such a manner that the absorption edge, which was obtained from Tauc plot with an assumption of direct transition using data on the absorption spectrum of the thin film of DBTPPn-II shown in FIG. 10B, was regarded as an optical energy gap and was added to the value of the HOMO level. According to the results, the HOMO level of DBTPPn-II was −5.86 eV, the energy gap was 3.45 eV, and the LUMO level was −2.41 eV.

EXAMPLE 2

In this example, a manufacturing method of a light-emitting element of one embodiment of the present invention and measurement results of element characteristics of the light-emitting element will be described with reference to drawings.

Figure 11:
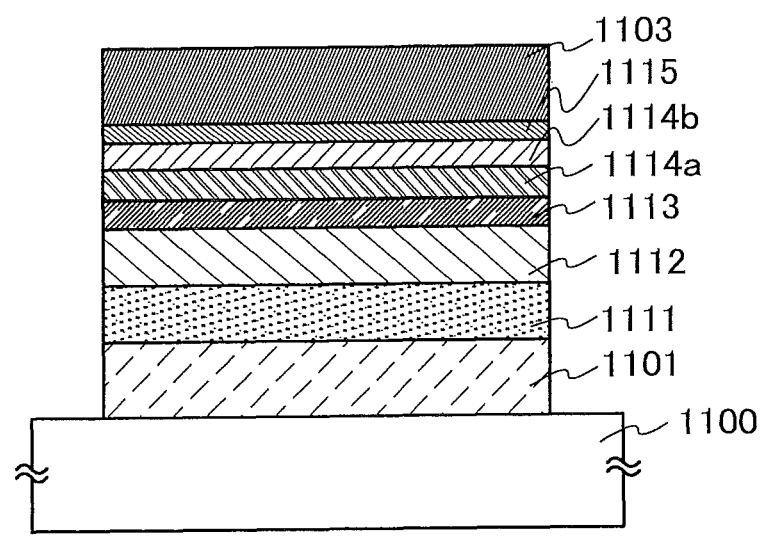
FIG. 11 illustrates a light-emitting element in Example 2.

A manufacturing method of a light-emitting element 1 of this example will be described with reference to FIG. 11. In addition, structural formulae of organic compounds used in this example are shown below.

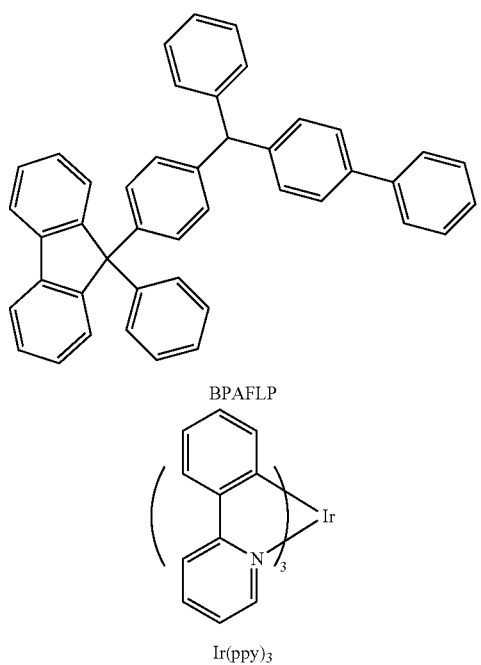

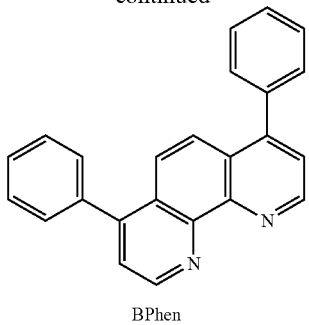

BPhen

Furthermore, a lithium fluoride (LiF) film was formed to a thickness of 1 nm on the second electron-transport layer 1114b by evaporation, whereby an electron-injection layer 1115 was formed.

Lastly, a 200-nm-thick film of aluminum was formed by evaporation, whereby a second electrode 1103 functioning as a cathode was formed. Thus, the light-emitting element 1 of this example was manufactured.

Note that a resistance heating method was used in all of the above evaporation steps.

Table 1 shows an element structure of the light-emitting element 1 obtained as described above.

TABLE 1

| | First electrode 1101 | Hole-injection layer 1111 | Hole-transport layer 1112 | Light-emitting layer 1113 | Electron-transport layer | | Electron-injection layer 1115 | Second electrode 1103 |
| --- | --- | --- | --- | --- | --- | --- | --- | --- |
| | | | | | 1114a | 1114b | | |
| Light-emitting element 1 | ITSO 110 nm | BPAFLP:MoOx (=4:2) 50 nm | BPAFLP 10 nm | DBTPPn-II:Ir(ppy)$_3$ (=1:0.08) 40 nm | DBTPPn-II 15 nm | BPhen 15 nm | LiF 1 nm | Al 200 nm |

*The mixture ratios are represented in weight ratios.

(Light-Emitting Element 1)

First, indium tin oxide containing silicon oxide (ITSO) was deposited on a glass substrate 1100 by a sputtering method, whereby a first electrode 1101 was formed. Note that the thickness was 110 nm and the electrode area was 2 mm×2 mm. In this example, the first electrode 1101 was used as an anode.

Next, the glass substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. After that, 4-phenyl-4'-(9-phenylfluoren-9-yl)triphenylamine (abbreviation: BPAFLP) and molybdenum(VI) oxide were co-evaporated, whereby a hole-injection layer 1111 was formed on the first electrode 1101. The thickness of the hole-injection layer 1111 was 50 nm. The weight ratio of BPAFLP to molybdenum oxide was adjusted to be 4:2 (=BPAFLP: molybdenum oxide). Note that the co-evaporation method refers to an evaporation method in which evaporation is carried out from a plurality of evaporation sources at the same time in one treatment chamber.

Next, BPAFLP was deposited to a thickness of 10 nm on the hole-injection layer 1111, whereby a hole-transport layer 1112 was formed.

Further, 4-[4-(9-phenanthryl)phenyl]dibenzothiophene (abbreviation: DBTPPn-II) synthesized in Example 1 and tris(2-phenylpyridinato-N,$C^{2'}$)iridium(III) (abbreviation: Ir(ppy)$_3$) were co-evaporated, whereby a light-emitting layer 1113 was formed on the hole-transport layer 1112. Here, the weight ratio of DBTPPn-II to Ir(ppy)$_3$ was adjusted to be 1:0.08 (=DBTPPn-II:Ir(ppy)$_3$). The thickness of the light-emitting layer 1113 was 40 nm.

Next, DBTPPn-II was deposited to a thickness of 15 nm on the light-emitting layer 1113, whereby a first electron-transport layer 1114a was formed.

After that, bathophenanthroline (abbreviation: BPhen) was deposited to a thickness of 15 nm on the first electron-transport layer 1114a, whereby a second electron-transport layer 1114b was formed.

In a glove box containing a nitrogen atmosphere, the light-emitting element 1 was sealed so as not to be exposed to the air. Then, operation characteristics of the light-emitting element were measured. Note that the measurement was carried out at room temperature (in an atmosphere kept at 25° C.).

Figure 12:
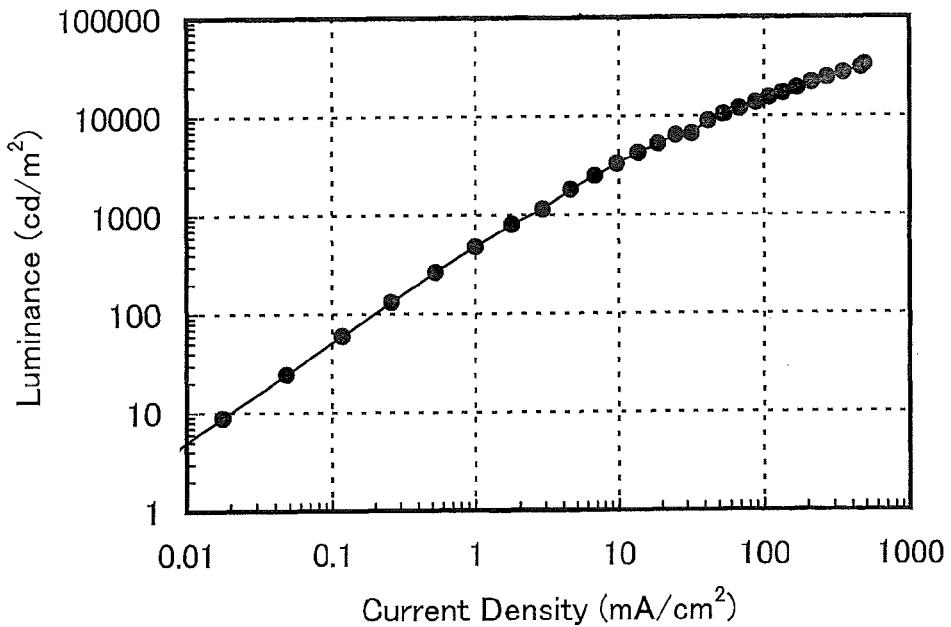
FIG. 12 shows current density-luminance characteristics of the light emitting element in Example 2.
Figure 13:
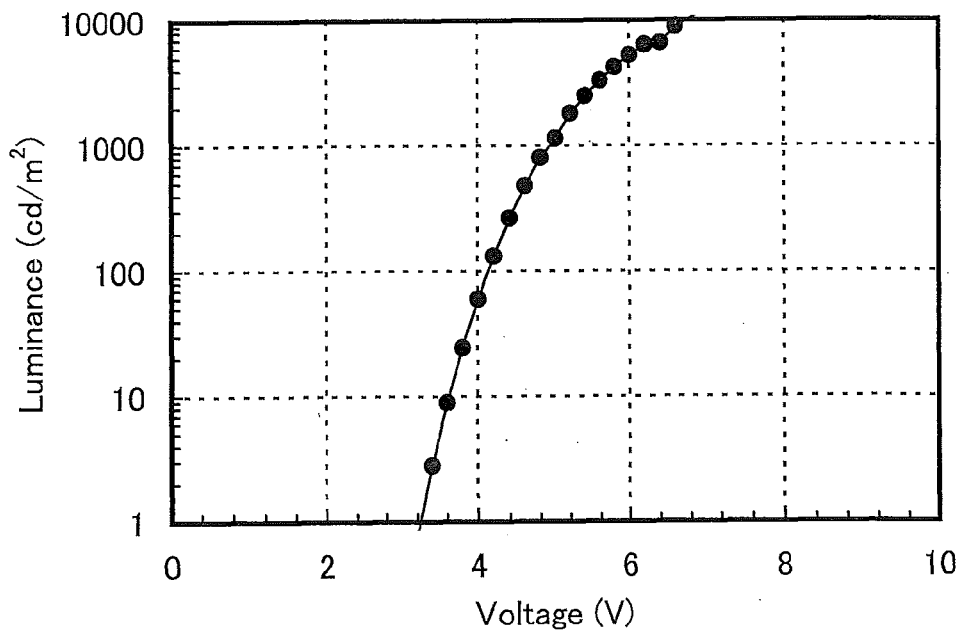
FIG. 13 shows voltage-luminance characteristics of the light-emitting element in Example 2.
Figure 14:
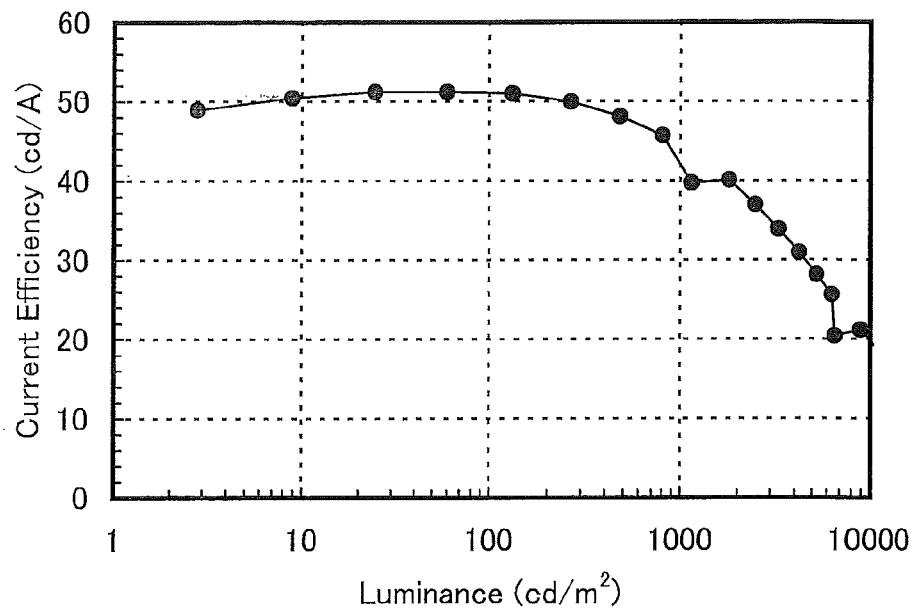
FIG. 14 shows luminance-current efficiency characteristics of the light-emitting element in Example 2.
Figure 15:
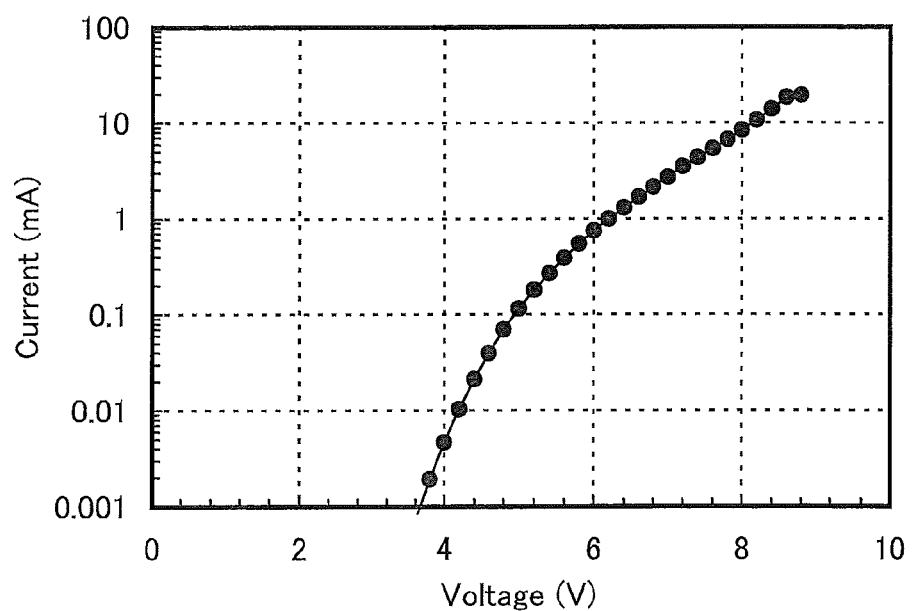
FIG. 15 shows voltage-current characteristics of the light-emitting element in Example 2.
Figure 16:
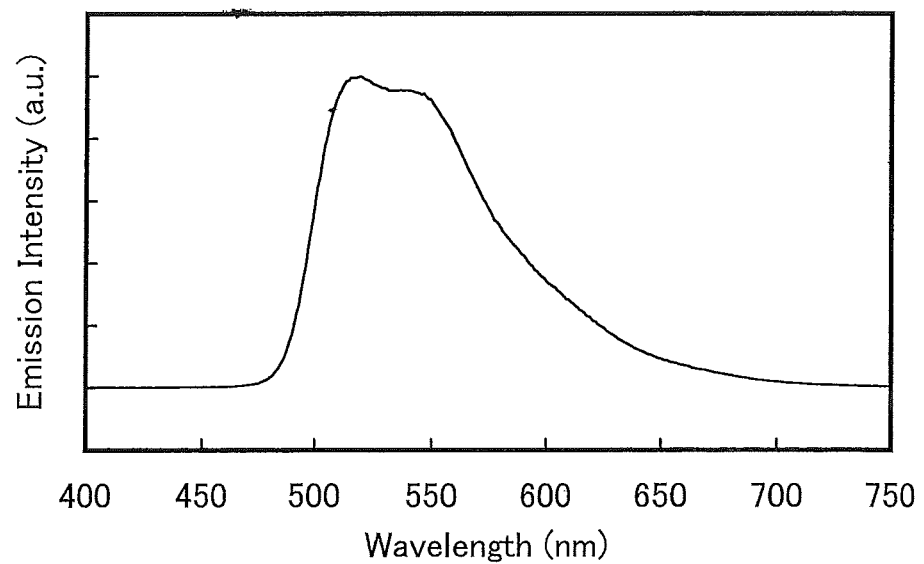
FIG. 16 shows an emission spectrum of the light-emitting element in Example 2.

FIG. 12 shows current density-luminance characteristics of the light-emitting element 1. FIG. 13 shows voltage-luminance characteristics thereof. FIG. 14 shows luminance-current efficiency characteristics thereof. FIG. 15 shows voltage-current characteristics thereof. In FIG. 12, the horizontal axis represents current density (mA/cm$^2$) and the vertical axis represents luminance (cd/m$^2$). In FIG. 13, the horizontal axis represents voltage (V) and the vertical axis represents luminance (cd/m$^2$). In FIG. 14, the horizontal axis represents luminance (cd/m$^2$) and the vertical axis represents current efficiency (cd/A). In FIG. 15, the horizontal axis represents voltage (V) and the vertical axis represents current (mA). FIG. 16 shows an emission spectrum of the light-emitting element 1. In FIG. 16, the horizontal axis represents wavelength (nm) and the vertical axis represents emission intensity (arbitrary unit).

In the light-emitting element 1, the voltage necessary for a luminance of 800 cd/m$^2$ was 4.8 V, and the current flowed at that time was 0.070 mA (current density was 1.76 mA/cm$^2$). The current efficiency at that time was 45.7 cd/A.

FIG. 12, FIG. 13, FIG. 14, FIG. 15, and FIG. 16 confirm that the light-emitting element of this example has characteristics as a light-emitting element and functions well.

According to FIG. 16, the emission spectrum of the light-emitting element 1 has a peak at around 520 nm, and green emission originating from Ir(ppy)$_3$ that is a guest material was observed. This shows that the phenanthrene compound described in Embodiment 1 (DBTPPn-II in this example) functions as a bipolar host material in the light-emitting layer of the light-emitting element.

Thus, the phenanthrene compound of one embodiment of the present invention is used in the light-emitting layer and the electron-transport layer, whereby the light-emitting element can have excellent characteristics. Further, the phenanthrene compound according to one embodiment of the present invention is used as a host material for a green phosphorescent compound in the light-emitting element of this example, and the T1 level of the phenanthrene compound according to one embodiment of the present invention was confirmed to be sufficiently high (higher than the T1 level of at least a green light-emitting material.)

EXAMPLE 3

In this example, an example of synthesizing 4-[3'-(9-phenanthryl)biphenyl-3-yl]dibenzothiophene (abbreviation: mDBTBPPn-II) represented by Structural Formula (109) in Embodiment 1 will be described.

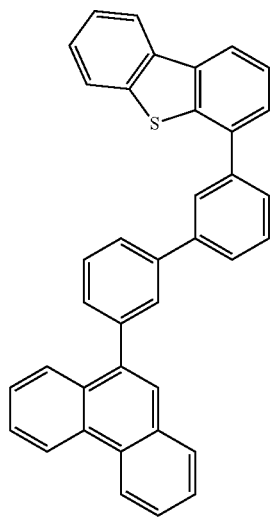

(109)

In a 50-mL three-neck flask were put 1.1 g (2.9 mmol) of 3-[3-(dibenzothiophen-4-yl)phenyl]phenylboronic acid, 0.75 g (2.9 mmol) of 9-bromophenanthrene, and 45 mg (0.15 mmol) of tris(2-methylphenyl)phosphine. The air in the flask was replaced with nitrogen. To the mixture were added 2.9 mL of a 2M aqueous potassium carbonate solution, 12 mL of toluene, and 3.5 mL of ethanol. The mixture was degassed by being stirred under reduced pressure. Then, 6.6 mg (0.029 mmol) of palladium(II) acetate was added to this mixture, and the mixture was stirred at 90° C. for 6 hours under a nitrogen stream. After a certain period of time, the aqueous layer of this mixture was extracted with toluene.

The obtained extract solution combined with the organic layer was washed with water and saturated saline, followed by drying with magnesium sulfate. This mixture was separated by gravity filtration, and the filtrate was concentrated to give an oily light brown substance. This oily substance was purified by silica gel column chromatography (developing solvent: toluene). The obtained fractions were concentrated to give an oily colorless substance. To this oily substance was added a mixed solvent of toluene and hexane to allow precipitation of a crystal, giving 1.2 g of a white solid that was the substance to be produced, in a yield of 80%.

By a train sublimation method, 1.2 g of the obtained white solid was purified. In the purification, the white solid was heated at 250° C. under a pressure of 3.6 Pa with a flow rate of argon gas of 5.0 mL/min. After the purification, 1.0 g of a white solid was obtained in a yield of 83%. The synthesis scheme of the above is shown in (F1) below.

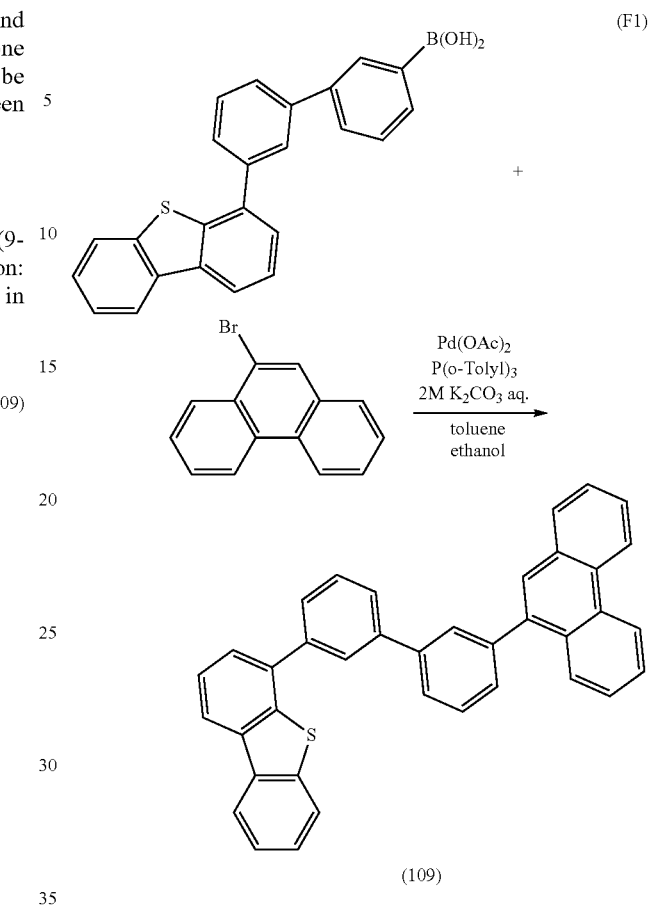

(F1)

(109)

A nuclear magnetic resonance (NMR) method identified this compound as 4-[3'-(9-phenanthryl)biphenyl-3-yl]dibenzothiophene (abbreviation: mDBTBPPn-II) that was the substance to be produced.

$^1$H NMR data of the obtained compound is as follows: $^1$H NMR (CDCl$_3$, 300 MHz): δ (ppm)=7.44-7.48 (m, 2H), 7.52-7.84 (m, 14H), 7.89-7.92 (m, 2H), 8.01 (dd, 1H), 8.07-8.08 (m, 1H), 8.14-8.21 (m, 2H), 8.74 (d, 1H), 8.79 (d, 1H).

Figure 17A:
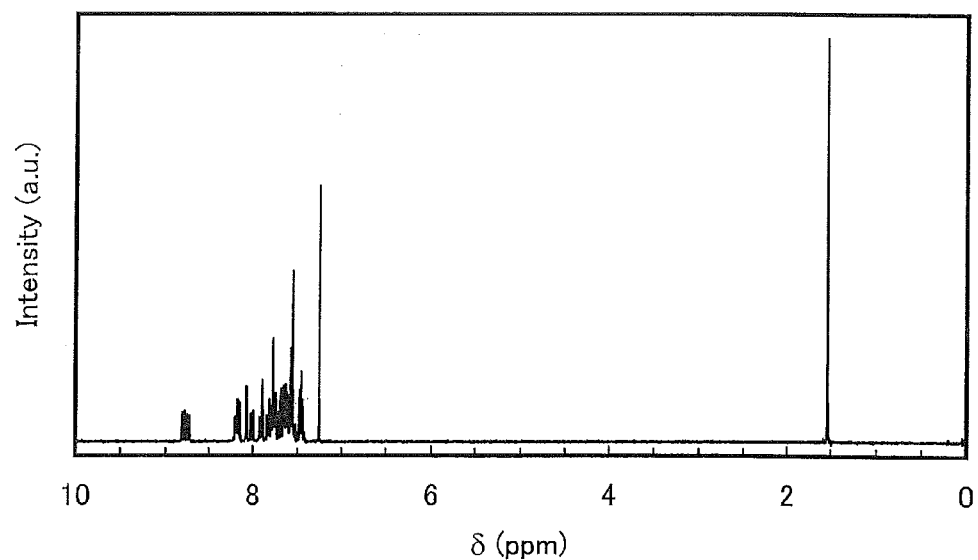
FIGS. 17A and 17B are NMR charts of mDBTBPPn-II.
Figure 17B:
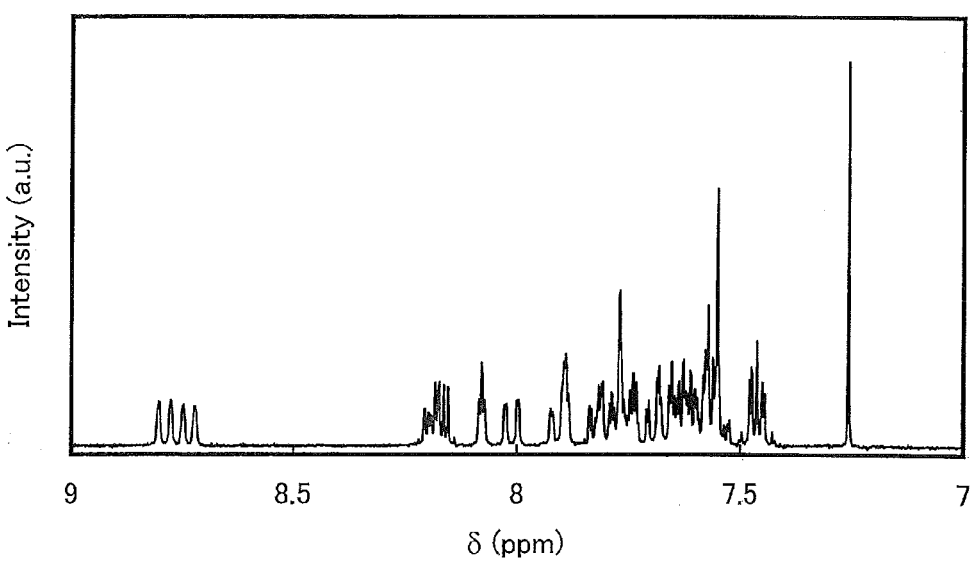

FIGS. 17A and 17B are $^1$H NMR charts. Note that FIG. 17B is a chart showing an enlarged part of FIG. 17A in the range of 7.0 ppm to 9.0 ppm.

Figure 18A:
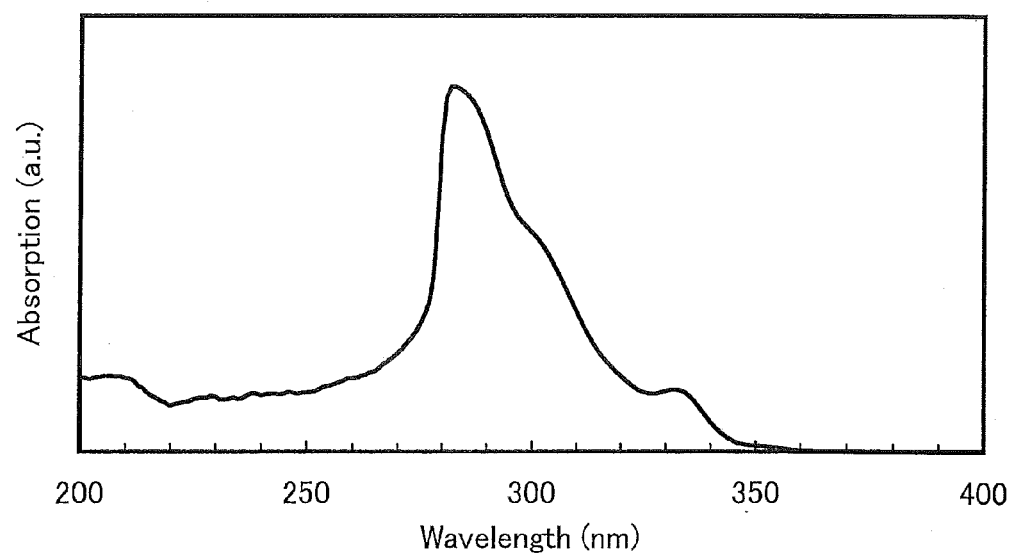
FIGS. 18A and 18B show an absorption spectrum and an emission spectrum of a toluene solution of mDBTBPPn-II.
Figure 18B:
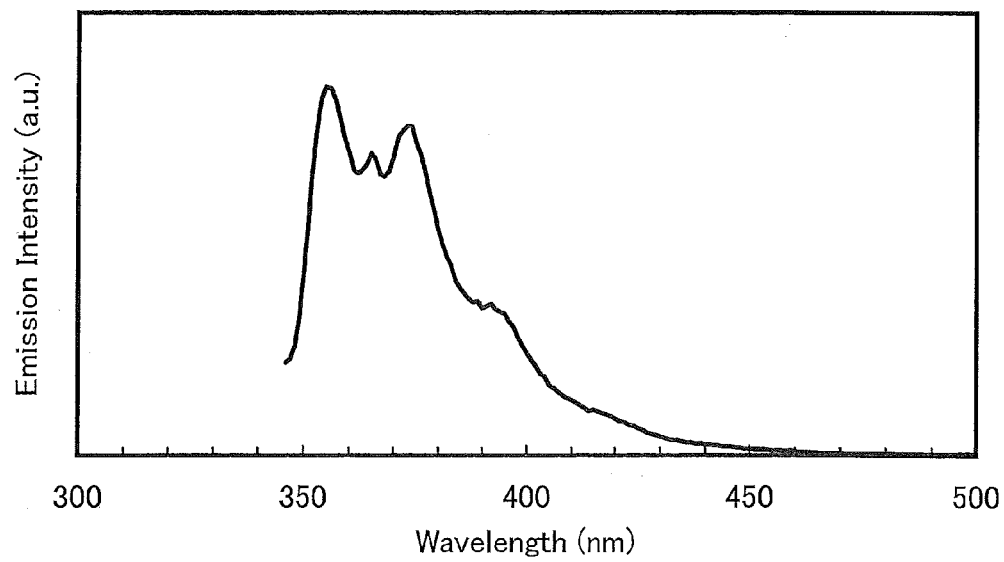
Figure 19A:
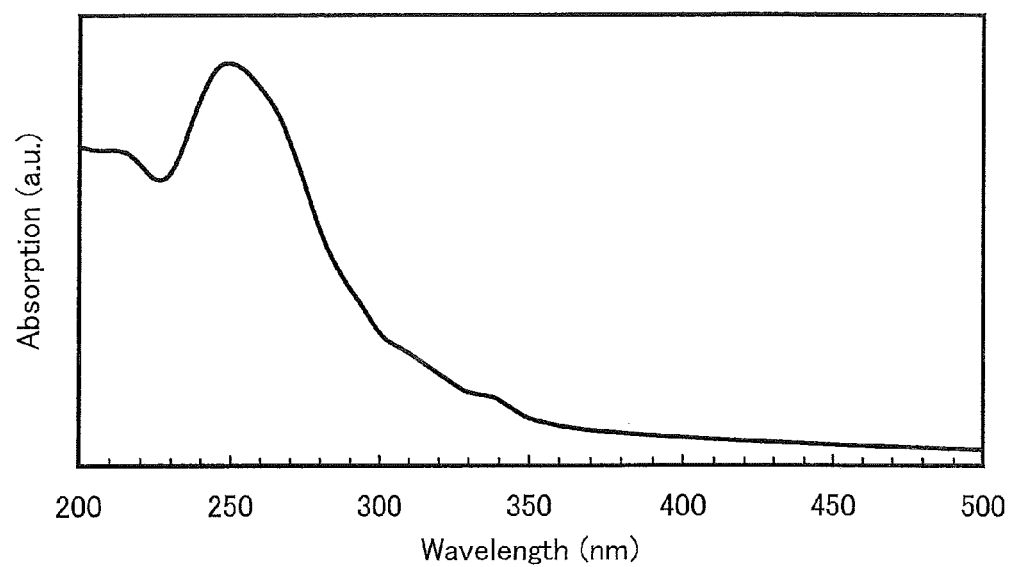
FIGS. 19A and 19B show an absorption spectrum and an emission spectrum of a thin film of mDBTBPPn-II.
Figure 19B:
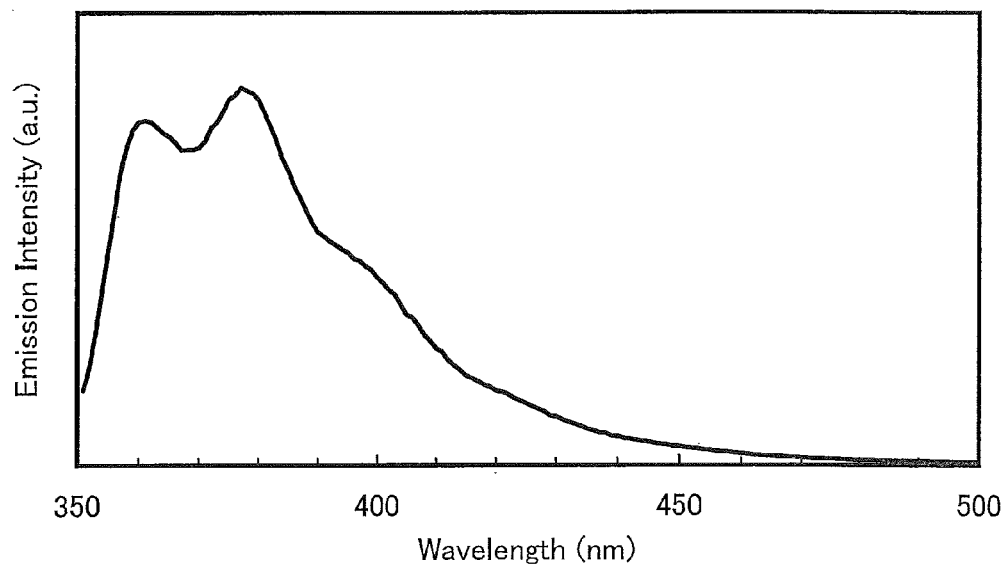

FIG. 18A shows an absorption spectrum of a toluene solution of mDBTBPPn-II, and FIG. 18B shows an emission spectrum thereof. FIG. 19A shows an absorption spectrum of a thin film of mDBTBPPn-II, and FIG. 19B shows an emission spectrum thereof. The absorption spectrum was measured with an ultraviolet-visible spectrophotometer (V550, produced by JASCO Corporation). The measurements were performed with samples prepared in such a manner that the solution was put in a quartz cell while the thin film was obtained by evaporation onto a quartz substrate. The absorption spectrum of the toluene solution of mDBTBPPn-II was obtained by subtracting the absorption spectra of the quartz cell and toluene from a raw data, and the absorption spectrum of the thin film of mDBTBPPn-II was obtained by subtracting the absorption spectrum of the quartz substrate from a raw data. In each of FIG. 18A and FIG. 19A, the horizontal axis represents wavelength (nm) and the vertical axis represents absorption intensity (arbitrary unit). In each of FIG. 18B and FIG. 19B, the horizontal axis represents wavelength (nm) and the vertical axis represents emission intensity (arbitrary unit).

In the case of the toluene solution, absorption peaks were observed at 282 nm and 331 nm, an absorption shoulder is observed at 298 nm, and emission wavelength peaks were observed at 356 nm, 365 nm, 374 nm, and 393 nm (excitation wavelength: 330 nm). In the case of the thin film, absorption peaks were observed at around 212 nm, 249 nm, and 334 nm, absorption shoulders are observed at 261 nm, 287 nm, and 305 nm, and emission wavelength peaks were observed at 361 nm and 377 nm, with a shoulder at 395 nm (excitation wavelength: 335 nm).

Further, the HOMO level and the LUMO level of the thin film of mDBTBPPn-II were measured. The value of the HOMO level was obtained by conversion of a value of the ionization potential measured with a photoelectron spectrometer (AC-2, manufactured by Riken Keiki Co., Ltd.) in the air into a negative value. The value of the LUMO level was obtained in such a manner that the absorption edge, which was obtained from Tauc plot with an assumption of direct transition using data on the absorption spectrum of the thin film of mDBTBPPn-II shown in FIG. 19B, was regarded as an optical energy gap and was added to the value of the HOMO level. According to the results, the HOMO level of mDBTBPPn-II was −5.90 eV, the energy gap was 3.47 eV, and the LUMO level was −2.43 eV.

EXAMPLE 4

In this example, manufacturing methods of light-emitting elements of one embodiment of the present invention and measurement results of element characteristics of the light-emitting elements will be described with reference to drawings.

Figure 20:
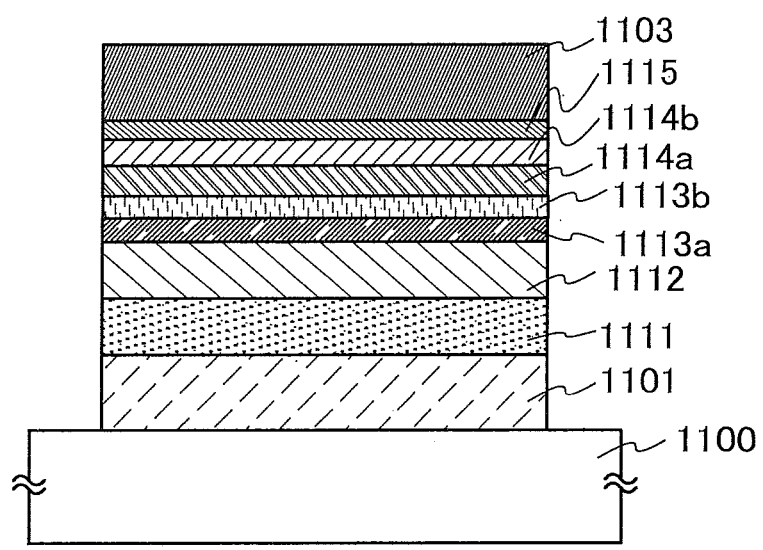
FIG. 20 illustrates light emitting elements in Example 4.

Manufacturing methods of a light-emitting element 2 and a light-emitting element 3 of this example will be described with reference to FIG. 20. An organic compound used in this example is shown below. Note that description of organic compounds the same as those described in Example 2 is omitted.

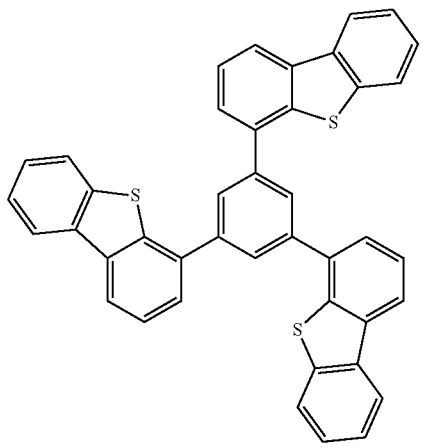

DBT3P-II (Light-Emitting Element 2)

First, indium tin oxide containing silicon oxide (ITSO) was deposited on a glass substrate 1100 by a sputtering method, whereby a first electrode 1101 was formed. Note that the thickness was 110 nm and the electrode area was 2 mm×2 mm. In this example, the first electrode 1101 was used as an anode.

Next, the glass substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. After that, 1,3,5-tri(dibenzothiophen-4-yl)-benzene (abbreviation: DBT3P-II) and molybdenum(VI) oxide were co-evaporated, whereby a hole-injection layer 1111 was formed on the first electrode 1101. The thickness of the hole-injection layer 1111 was 40 nm. The weight ratio of DBT3P-II to molybdenum oxide was adjusted to be 4:2 (=DBT3P-II:molybdenum oxide). Note that the co-evaporation method refers to an evaporation method in which evaporation is carried out from a plurality of evaporation sources at the same time in one treatment chamber.

Next, BPAFLP was deposited to a thickness of 20 nm on the hole-injection layer 1111, whereby a hole-transport layer 1112 was formed.

Further, 4-[4-(9-phenanthryl)phenyl]dibenzothiophene (abbreviation: DBTPPn-II) synthesized in Example 1 and tris(2-phenylpyridinato-N,C$^{2'}$)iridium(III) (abbreviation: Ir(ppy)$_3$) were co-evaporated, whereby a light-emitting layer was formed on the hole-transport layer 1112. The light-emitting layer here had a stacked structure of a first light-emitting layer 1113a with a thickness of 10 nm and a second light-emitting layer 1113b with a thickness of 20 nm. The first light-emitting layer 1113a was formed in such a manner that the weight ratio of DBTPPn-II to Ir(ppy)$_3$ was adjusted to be 1:0.08 (=DBTPPn-II:Ir(ppy)$_3$). The second light-emitting layer 1113b was formed in such a manner that the weight ratio of DBTPPn-II to Ir(ppy)$_3$ was adjusted to be 1:0.04 (=DBTPPn-II:Ir(ppy)$_3$).

Next, DBTPPn-II was deposited to a thickness of 10 nm on the second light-emitting layer 1113b, whereby a first electron-transport layer 1114a was formed.

Then, bathophenanthroline (abbreviation: BPhen) was deposited to a thickness of 20 nm on the first electron-transport layer 1114a, whereby a second electron-transport layer 1114b was formed.

Furthermore, a lithium fluoride (LiF) film was formed to a thickness of 1 nm on the second electron-transport layer 1114b by evaporation, whereby an electron-injection layer 1115 was formed.

Lastly, a 200-nm-thick film of aluminum was formed by evaporation, whereby a second electrode 1103 functioning as a cathode was formed. Thus, the light-emitting element 2 of this example was manufactured.

Note that a resistance heating method was used in all of the above evaporation steps.

Next, a manufacturing method of the light-emitting element 3 will be described.

(Light-Emitting Element 3)

The light-emitting element 3 was manufactured in a manner similar to that of the light-emitting element 2 by using the same substrate and using 4-[3'-(9-phenanthryl)biphenyl-3-yl]dibenzothiophene (abbreviation: mDBTBPPn-II) described in Example 3 instead of DBTPPn-II in a light-emitting layer. In other words, the light-emitting layer of the light-emitting element 3 was formed by co-evaporation of mDBTBPPn-II and tris(2-phenylpyridinato-N,C$^{2'}$)iridium(III) (abbreviation: Ir(ppy)$_3$). The light-emitting layer here had a stacked structure of a first light-emitting layer 1113a with a thickness of 10 nm and a second light-emitting layer 1113b with a thickness of 20 nm. The first light-emitting layer 1113a was formed in such a manner that the weight ratio of mDBTBPPn-II to Ir(ppy)$_3$ was adjusted to be 1:0.08 (=mDBTBPPn-II:Ir(ppy)$_3$). The second light-emitting layer 1113b was formed in such a manner that the weight ratio of mDBTBPPn-II to Ir(ppy)$_3$ was adjusted to be 1:0.04 (=mDBTBPPn-II:Ir(ppy)$_3$).

Next, mDBTBPPn-II was deposited to a thickness of 10 nm on the second light-emitting layer 1113b, whereby a first electron-transport layer 1114a was formed.

Note that the light-emitting element 3 was formed in a manner similar to that of the light-emitting element 2 except for the light-emitting layer and the first electron-transport layer 1114a.

Table 2 shows element structures of the light-emitting element 2 and the light-emitting element 3.

Ir(ppy)$_3$ that is a guest material was observed therefrom. The above means that the phenanthrene compounds described in Embodiment 1 (DBTPPn-II and mDBTBPPn-II in this example) function as bipolar host materials in the light-emitting layers of the light-emitting elements.

Figure 26:
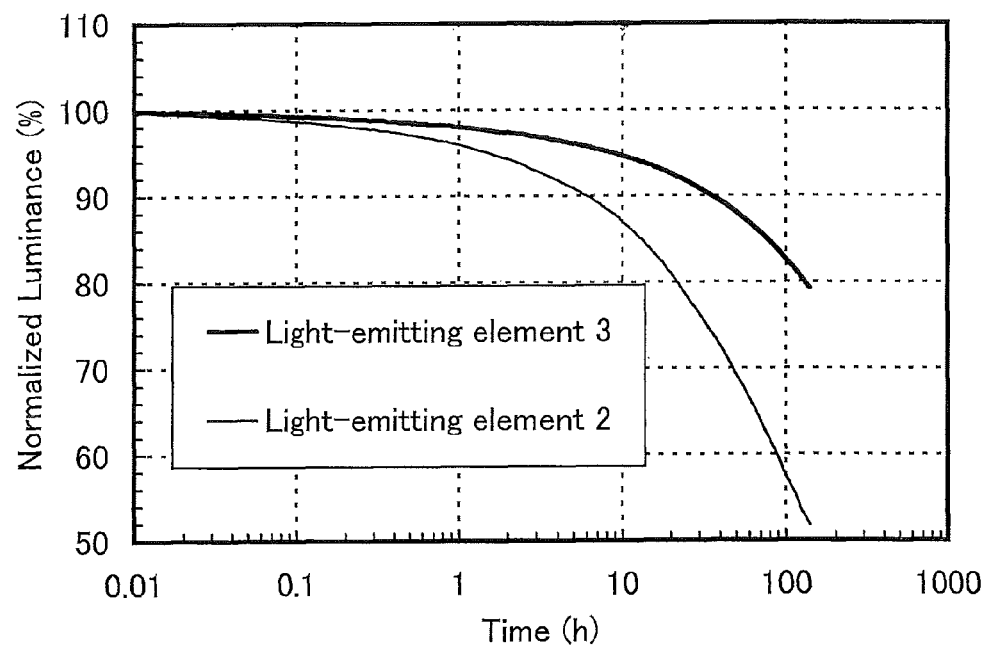
FIG. 26 shows results of a reliability test of the light-emitting elements in Example 4.

Next, the light-emitting element 2 and the light-emitting element 3 were subjected to a reliability test. In the reliability test, the initial luminance was set at 5000 cd/m$^2$, the light-emitting element 2 and the light-emitting element 3 of this example were driven at a constant current density, and the luminance was measured at regular intervals. FIG. 26 shows results of the reliability test. In FIG. 26, the vertical axis

TABLE 2

| | First electrode | Hole-injection | Hole-transport layer | Light-emitting layer | | Electron-transport layer | | Electron-injection layer | Second electrode |
|---|---|---|---|---|---|---|---|---|---|
| | 1101 | layer 1111 | 1112 | 1113a | 1113b | 1114a | 1114b | 1115 | 1103 |
| Light-emitting element 2 | ITSO 110 nm | DBT3P-II:MoOx (=4:2) 40 nm | BPAFLP 20 nm | DBTPPn-II:Ir(ppy)$_3$ (=1:0.08) 10 nm | DBTPPn-II:Ir(ppy)$_3$ (=1:0.04) 20 nm | DBTPPn-II 10 nm | BPhen 20 nm | LiF 1 nm | Al 200 nm |
| Light-emitting element 3 | ITSO 110 nm | DBT3P-II:MoOx (=4:2) 40 nm | BPAFLP 20 nm | mDBTBPPn-II:Ir(ppy)$_3$ (=1:0.08) 10 nm | mDBTBPPn-II:Ir(ppy)$_3$ (=1:0.04) 20 nm | DBTPPn-II 10 nm | BPhen 20 nm | LiF 1 nm | Al 200 nm |

*The mixture ratios are represented in weight ratios.

In a glove box containing a nitrogen atmosphere, the thus obtained light-emitting element 2 and light-emitting element 3 were sealed so as not to be exposed to the air. Then, operation characteristics of each of the light-emitting elements were measured. Note that the measurement was carried out at room temperature (in an atmosphere kept at 25° C.).

Figure 21:
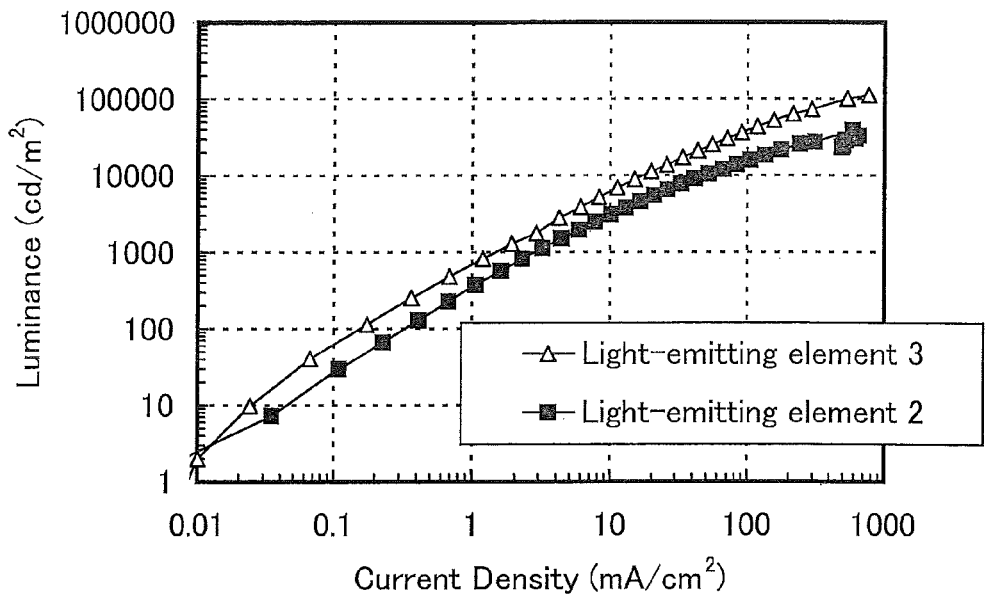
FIG. 21 shows current density-luminance characteristics of the light-emitting elements in Example 4.
Figure 22:
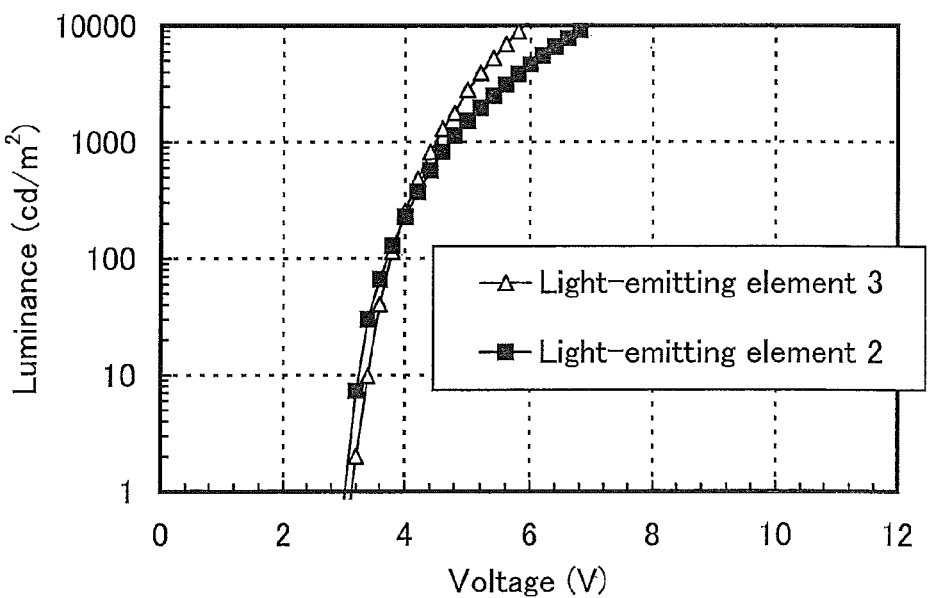
FIG. 22 shows voltage-luminance characteristics of the light-emitting elements in Example 4.
Figure 23:
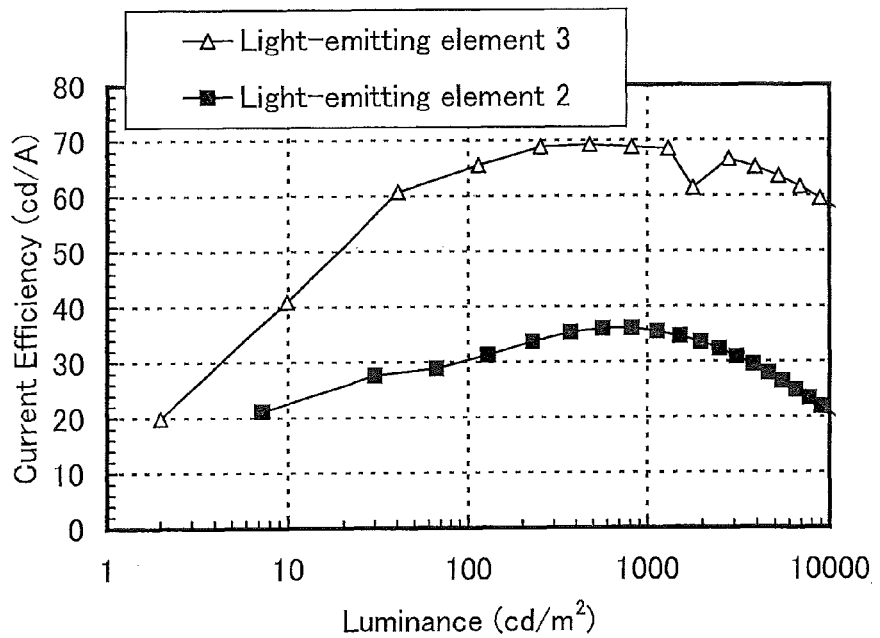
FIG. 23 shows luminance-current efficiency characteristics of the light-emitting elements in Example 4.
Figure 24:
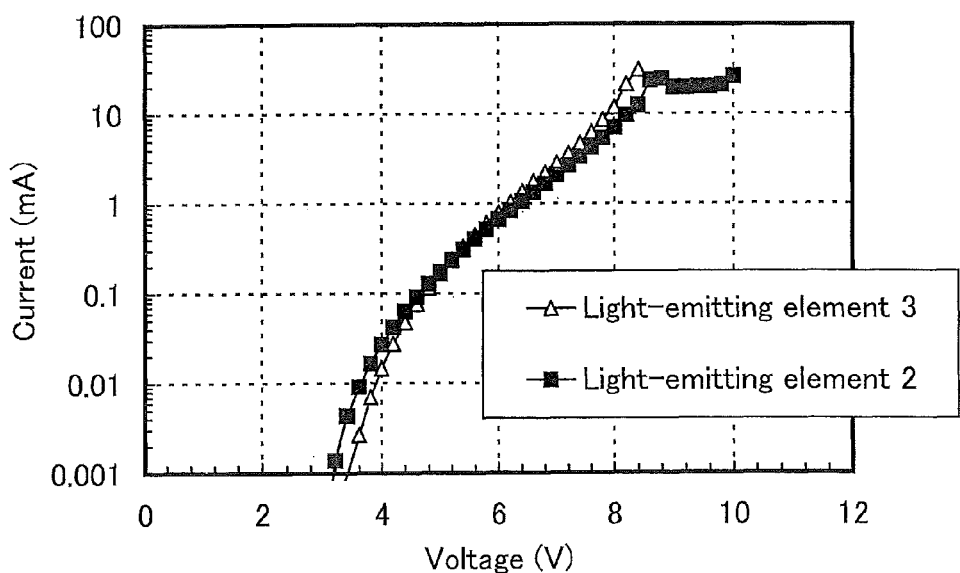
FIG. 24 shows voltage-current characteristics of the light-emitting elements in Example 4.
Figure 25:
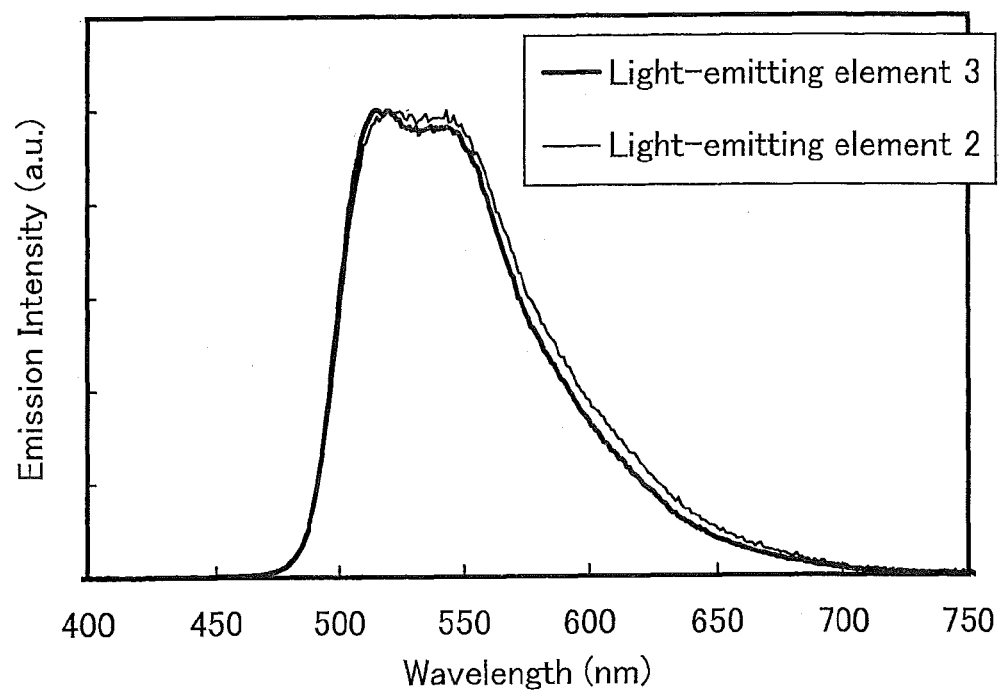
FIG. 25 shows an emission spectrum of the light-emitting elements in Example 4.

FIG. 21 shows current density-luminance characteristics of the light-emitting element 2 and the light-emitting element 3. FIG. 22 shows voltage-luminance characteristics thereof. FIG. 23 shows luminance-current efficiency characteristics thereof. FIG. 24 shows voltage-current characteristics thereof. In FIG. 21, the horizontal axis represents current density (mA/cm$^2$) and the vertical axis represents luminance (cd/m$^2$). In FIG. 22, the horizontal axis represents voltage (V) and the vertical axis represents luminance (cd/m$^2$). In FIG. 23, the horizontal axis represents luminance (cd/m$^2$) and the vertical axis represents current efficiency (cd/A). In FIG. 24, the horizontal axis represents voltage (V) and the vertical axis represents current (mA). FIG. 25 shows emission spectra of the light-emitting element 2 and the light-emitting element 3. In FIG. 25, the horizontal axis represents wavelength (nm) and the vertical axis represents emission intensity (arbitrary unit).

According to FIG. 21, FIG. 22, FIG. 23, and FIG. 24, the luminance of the light-emitting element 2 at an applied voltage of 4.8 V was 1130 cd/m$^2$, and the current flowed at that time was 0.13 mA (the current density was 3.2 mA/cm$^2$). The current efficiency at that time was 35.5 cd/A. These results showed that light emission was able to be obtained efficiently from the light-emitting element 2.

In contrast, the luminance of the light-emitting element 3 at an applied voltage of 4.4 V was 820 cd/m$^2$, and the current flowed at that time was 0.05 mA (the current density was 1.2 mA/cm$^2$). The current efficiency at that time was 68.8 cd/A. These results showed that light emission was able to be obtained from the light-emitting element 3 more efficiently.

According to FIG. 25, the emission spectra of the light-emitting element 2 and the light-emitting element 3 gave peaks at 515 to 520 nm, and green emission originating from represents the percentage of luminance at each time point on the assumption that the initial luminance is 100%, that is, normalized luminance (%), and the horizontal axis represents driving time (h) of the elements.

According to FIG. 26, the light-emitting element 2 and the light-emitting element 3 respectively maintained 52% and 79% of the initial luminance even after being driven for 140 hours. The results show that the light-emitting element in which mDBTBPPn-II is used has long lifetime. Therefore, the light-emitting element in which the phenanthrene compound of the present invention is used has a long lifetime.

REFERENCE EXAMPLE

In this reference example, an example of synthesizing 4-phenyl-4'-(9-phenylfluoren-9-yl)triphenylamine (abbreviation: BPAFLP) that was used as a material of the light-emitting element 1, the light-emitting element 2, and the light-emitting element 3 will be described.

Step 1: Synthesis Method of 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that bubble release and heat generation were confirmed. After 12 g (50 mmol) of 2-bromobiphenyl dissolved in 10 mL of dehydrated diethyl ether was slowly added into this mixture, the mixture was stirred and heated under reflux for 2.5 hours, whereby a Grignard reagent was prepared.

In a 500-mL three-neck flask were put 10 g (40 mmol) of 4-bromobenzophenone and 100 mL of dehydrated diethyl ether. After the Grignard reagent synthesized in advance was slowly added into this mixture, the mixture was heated and stirred under reflux for 9 hours.

After reaction, the mixture was filtered to give a residue. The residue was dissolved in 150 mL of ethyl acetate, and 1N hydrochloric acid was added to acidify the solution which was then stirred for 2 hours. The organic layer of this solution was washed with water. Then, magnesium sulfate was added to remove moisture. This suspension was filtered, and the resulting filtrate was concentrated to give an oily substance. In a 500-mL recovery flask were put this oily substance, 50 mL of glacial acetic acid, and 1.0 mL of hydrochloric acid. The mixture was reacted by heating at 130° C. for 1.5 hours under a nitrogen atmosphere with stirring.

After reaction, this reaction mixture was filtered to give a residue. The obtained residue was washed with water, a sodium hydroxide aqueous solution, water, and methanol in this order, and then dried to give 11 g of white powder that was the substance to be produced, in a yield of 69%. The synthesis scheme of Step 1 is shown in (J-1) below.

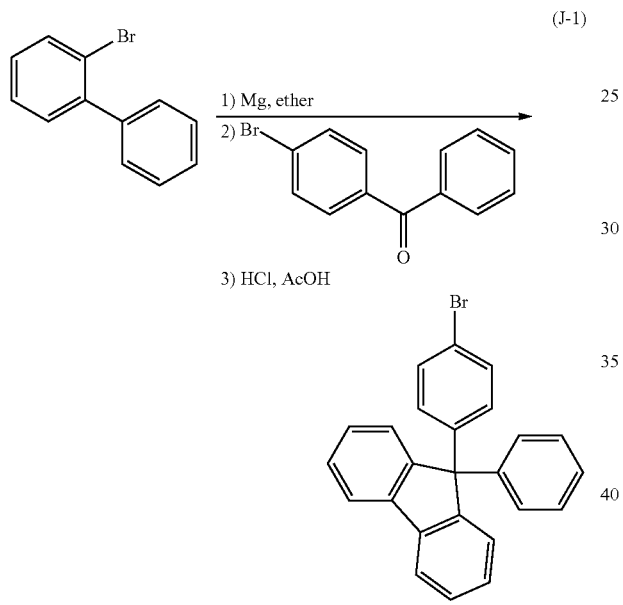

Step 2: Synthesis Method of 4-phenyl-4'-(9-phenylfluoren-9-yl)triphenylamine (Abbreviation: BPAFLP)

In a 100-mL three-neck flask were put 3.2 g (8.0 mmol) of 9-(4-bromophenyl)-9-phenylfluorene, 2.0 g (8.0 mmol) of 4-phenyldiphenylamine, 1.0 g (10 mmol) of sodium tert-butoxide, and 23 mg (0.04 mmol) of bis(dibenzylideneacetone)palladium(0). The atmosphere in the flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was allowed to be reacted by heating at 110° C. for 2 hours under a nitrogen atmosphere with stirring.

After reaction, 200 mL of toluene was added to the reaction mixture, and the resulting suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (with a developing solvent containing toluene and hexane in a 1:4 ratio). The obtained fractions were concentrated, and acetone and methanol were added thereto. The mixture was irradiated with ultrasonic waves and allowed a crystal to precipitate, giving 4.1 g of white powder that was the substance to be produced, in a yield of 92%. The synthesis scheme of Step 2 is shown in (J-2)

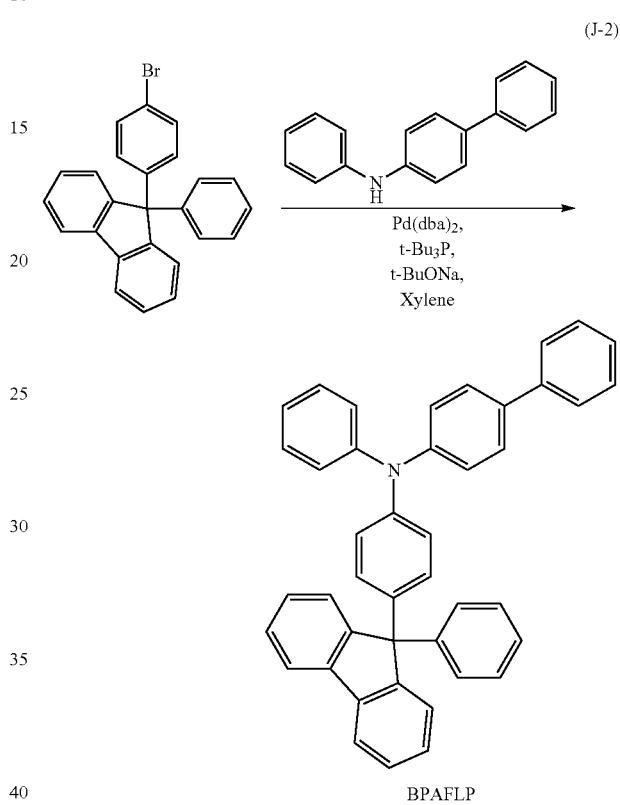

The Rf values of the substance to be produced, 9-(4-bromophenyl)-9-phenylfluorene, and 4-phenyl-diphenylamine were respectively 0.41, 0.51, and 0.27, which were obtained by silica gel thin layer chromatography (TLC) (with a developing solvent containing ethyl acetate and hexane in a 1:10 ratio).

A nuclear magnetic resonance (NMR) method identified this compound as 4-phenyl-4'-(9-phenylfluoren-9-yl)triphenylamine (abbreviation: BPAFLP) that was the substance to be produced.

$^1$H NMR data of the obtained compound is as follows: $^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

This application is based on Japanese Patent Application serial no. 2010-243323 filed with Japan Patent Office on Oct. 29, 2010, the entire contents of which are hereby incorporated by reference.

What is claimed is:
1. A light-emitting element comprising:
a pair of electrodes;
an electroluminescence layer between the pair of electrodes, the electroluminescence layer comprising a first light-emitting layer;

wherein the first light-emitting layer comprises a first phenanthrene compound and a light-emitting substance, and wherein the first phenanthrene compound is represented by Formula (109):

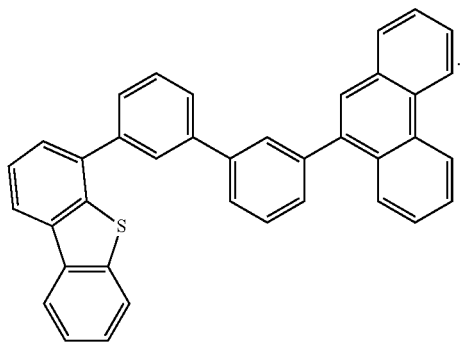

(109)

2. The light-emitting element according to claim 1, wherein the light-emitting substance comprises tris(2-phenylpyridinato-N,C')iridium(III).

3. The light-emitting element according to claim 1 further comprising:
a second light-emitting layer,
wherein the second light-emitting layer comprises a second phenanthrene compound.

4. The light-emitting element according to claim 3, wherein the second phenanthrene compound is represented by Formula (109).

5. A display device comprising the light-emitting element according to claim 1.

6. An electronic device comprising the light-emitting element according to claim 1.

7. A lighting device comprising the light-emitting element according to claim 1.

8. The lighting device according to claim 7, wherein the lighting device is capable of emitting white light.

9. A light-emitting element comprising:
a pair of electrodes;
an electroluminescence layer between the pair of electrodes, the electroluminescence layer comprising a first light-emitting layer and a second light-emitting layer;
wherein the first light-emitting layer comprises a phenanthrene compound and a light-emitting substance,
wherein the phenanthrene compound is represented by Formula (G1):

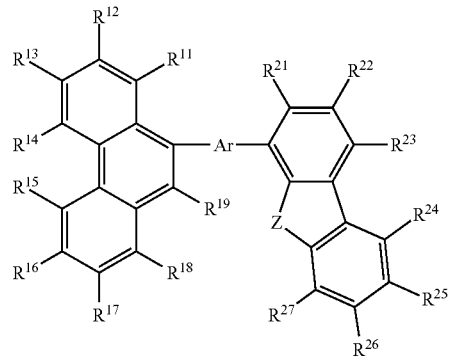

(G1)

wherein $R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms,
wherein Ar represents a substituted or unsubstituted biphenyldiyl group, and
wherein Z represents a sulfur atom or an oxygen atom.

10. The light-emitting element according to claim 9, wherein the light-emitting substance comprises tris(2-phenylpyridinato-N,C')iridium(III).

11. A display device comprising the light-emitting element according to claim 9.

12. An electronic device comprising the light-emitting element according to claim 9.

13. A lighting device comprising the light-emitting element according to claim 9.

14. The lighting device according to claim 13, wherein the lighting device is capable of emitting white light.

* * * * *